(12) United States Patent
Lee et al.

(10) Patent No.: US 8,193,168 B2
(45) Date of Patent: Jun. 5, 2012

(54) USE OF A TRPM5 INHIBITOR TO REGULATE INSULIN AND GLP-1 RELEASE

(75) Inventors: S. Paul Lee, Newtown, PA (US); Peihong Zhou, East Brunswick, NJ (US); M. N. Tulu Buber, Newtown, PA (US); Rok Cerne, Lawrenceville, NJ (US); Robert Bryant, Princeton, NJ (US); F. Raymond Salemme, Yardley, PA (US); Gillian Morgan, Philadelphia, PA (US)

(73) Assignee: Redpoint Bio Corporation, Ewing, NJ (US)

(*) Notice: Subject to any disclaimer, the term of this patent is extended or adjusted under 35 U.S.C. 154(b) by 0 days.

(21) Appl. No.: 12/025,488

(22) Filed: Feb. 4, 2008

(65) Prior Publication Data

US 2008/0306030 A1 Dec. 11, 2008

Related U.S. Application Data

(60) Provisional application No. 61/016,394, filed on Dec. 21, 2007, provisional application No. 60/887,996, filed on Feb. 2, 2007.

(51) Int. Cl.
*A61K 31/655* (2006.01)
*A61K 31/415* (2006.01)
(52) U.S. Cl. .................. 514/150; 514/407; 514/866
(58) Field of Classification Search .............. 514/183, 514/150, 407, 866
See application file for complete search history.

(56) References Cited

U.S. PATENT DOCUMENTS

| | | | |
|---|---|---|---|
| 3,746,703 A | 7/1973 | Bruce |
| 3,859,281 A | 1/1975 | Bruce |
| 4,684,534 A | 8/1987 | Valentine |
| 5,011,678 A | 4/1991 | Wang et al. |
| 5,072,042 A | 12/1991 | Janssen et al. |
| 6,060,078 A | 5/2000 | Lee |
| 6,187,332 B1 | 2/2001 | Gern et al. |
| 6,316,029 B1 | 11/2001 | Jain et al. |
| 6,368,625 B1 | 4/2002 | Siebert et al. |
| 6,403,142 B1 | 6/2002 | McDaniel, III et al. |
| 6,485,709 B2 | 11/2002 | Banerjee et al. |
| 6,540,978 B1 | 4/2003 | Margolskee et al. |
| 6,583,118 B1 | 6/2003 | Watanabe et al. |
| 6,613,942 B1 | 9/2003 | Ling et al. |
| 6,649,186 B1 | 11/2003 | Robinson et al. |
| 6,773,716 B2 | 8/2004 | Ream et al. |
| 6,916,798 B2 | 7/2005 | Green et al. |
| 7,087,394 B2 | 8/2006 | Johnson et al. |
| 7,211,557 B2 | 5/2007 | DiMarchi et al. |
| 2003/0187007 A1 | 10/2003 | Cao et al. |
| 2004/0171073 A1 | 9/2004 | Neiland et al. |
| 2004/0259160 A1 | 12/2004 | Johnson et al. |
| 2005/0019830 A1 | 1/2005 | Penner et al. |
| 2005/0182011 A1 | 8/2005 | Olson et al. |
| 2005/0244810 A1 | 11/2005 | Egan et al. |
| 2006/0040947 A1 | 2/2006 | Blurton et al. |
| 2007/0111264 A1 | 5/2007 | Bryant et al. |
| 2007/0161052 A1 | 7/2007 | Servant et al. |
| 2007/0207093 A1 | 9/2007 | Bryant et al. |

FOREIGN PATENT DOCUMENTS

| | | |
|---|---|---|
| EP | 0 294 258 A1 | 12/1988 |
| WO | WO 92/19236 A1 | 11/1992 |
| WO | WO 99/01423 A1 | 1/1999 |
| WO | WO 9940062 A1 * | 8/1999 |
| WO | WO 01/30412 A1 | 5/2001 |
| WO | WO 01/66541 A1 | 9/2001 |
| WO | WO 03/049698 A2 | 6/2003 |
| WO | WO 2004/028464 A2 | 4/2004 |
| WO | WO 2004/032716 A2 | 4/2004 |
| WO | WO 2004/072183 A1 | 8/2004 |
| WO | WO 2004/083312 A2 | 9/2004 |
| WO | WO 2004/105488 A1 | 12/2004 |
| WO | WO 2007/101710 A1 | 9/2007 |

OTHER PUBLICATIONS

Amer, A.M., et al., "On the Chemistry of Cinnoline I. Synthesis and Reactions of (4-Amino-cinnolin-3-yl)-p-tolyl-methanones," *Monatshefte für Chemie 130*:1409-1418, Springer-Verlag (1999).

Atallah, R.H. and Nazer, M.Z., "Oxides of 3-Methyl-1,2,4-Benzotriazine," *Tetrahedron 38*:1793-1796, Elsevier Science Ltd. (1982).

Avenet, P. and Lindemann, B., "Perspectives of Taste Reception," *J. Membrane Biol. 112*:1-8, Springer-Verlag (1989).

Bundgaard, H., in *Design of Prodrugs*, Bundgaard, H., eds., Elsevier Science Publishers B.V., Amsterdam, The Netherlands, pp. 7-24 (1985).

De Heer, J. and Holst, J.J., "Sulfonylurea Compounds Uncouple the Glucose Dependence of the Insulinotropic Effect of Glucagon-Like Peptide 1," *Diabetes 56*:438-443, American Diabetes Association (Feb. 2007).

Deacon, C.F., "What do we know about the secretion and degradation of incretin hormones?" *Regulatory Peptides 128*:117-124, Elsevier Science Ltd. (2005).

Doty, R.L., et al., "Influences of antihypertensive and antihyperlipidemic drugs on the senses of taste and smell: A review," *Journal of Hypertension 21*:1805-1813, Lippincott Williams & Wilkins (2003).

Elderfield, R.C. and Wood, J.R., "Synthesis of Potential Anticancer Agents. XV. Nirogen Mustards from Indole Derivatives," *J. Org. Chem. 27*:2463-2465, American Chemical Society (1962).

Elmegeed, G.A., et al., "Synthesis and Antimicrobial Evaluation of Some Novel Cholestane Heterocyclic Derivatives," *Arch. Pharm. Pharm. Med. Chem. 337*:140-147, John Wiley & Sons, Inc. (2004).

Geelhoed-Duijvestijn, P.H.L.M., "Incretins: A new treatment option for type 2 diabetes?," *Neth J Med 65*:60-64, Van Zuiden Communications (Feb. 2007).

(Continued)

*Primary Examiner* — Kevin Weddington
(74) *Attorney, Agent, or Firm* — Sterne, Kessler, Goldstein & Fox PLLC

(57) ABSTRACT

The present invention is directed to methods of enhancing insulin release, GLP-1 release, and insulin sensitivity, methods of increasing insulin gene expression, methods of decreasing gastric secretion and emptying and glucagons secretion, and methods of inhibiting food intake, and methods of treating diabetes mellitus, insulin resistance syndrome, hyperglycemia, and obesity comprising administering to a subject an effective amount of a TRPM5 inhibitor.

22 Claims, 20 Drawing Sheets

OTHER PUBLICATIONS

Gent, J.F., et al., "Taste Confusions Following Chlorhexidine Treatment," *Chem. Senses* 27:73-80, Oxford university Press (2002).

"Glucagon-Like-Peptide-1 ELISA using GLUTag cells" (Oct. 2007).

Hofmann, T., et al., "TRPM5 is a Voltage-Modulated and Ca2+-Activated Monovalent Selective Cation Channel," *Current Biology* 13:1153-1158, Elsevier Science Ltd. (2003).

Huang, C.-L., "The Transient Receptor Potential Superfamily of Ion Channels," *J Am Soc Nephrol* 15:1690-1699, American Society of Nephrology (2004).

Jang, H.-J., et al., "Gut-expressed gustducin and taste receptors regulate secretion of glucagon-like peptide-1," *PNAS* 104:15069-15074, National Academy of Sciences (Sep. 2007).

Katritzky, A.R., et al., "Synthesis of Formazans Under Phase-Transfer Conditions," *Synthesis* 1995:577-581, Thieme Medical Publishers, Inc. (1995).

Kidwai, M., et al., "Synthesis and Antifertility Activity of 1,5-Diary1-3-(3' -indolyl)formazans," *Chem. Pharm. Bull.* 42:2363-2364, Pharmaceutical-Society of Japan (1994).

Kinnamon, S.C., "Taste transduction: A diversity of mechanisms," *TINS* 11:491-496, Elsevier Publications (1988).

Knudsen, L.B., et al., "Small-molecule agonists for the glucagon-like peptide 1 receptor," *PNAS* 104:937-942, National Academy of Sciences (Jan. 2007).

Kokrashvili, Z. et al., AChemS XXIXth Annual Meeting: Abstract 246, Sarasota, Florida (Apr. 25-29, 2007).

Kreymann, B., et al., "Glucagon-like Peptide-1 7-36: A Physiological Incretin in Man," *Lancet* 2:1300-1304, Elsevier Science Ltd. (1987).

Latham, D.W.S., et al., "Reaction of Benzofurazan N-Oxide with Secondary Aliphatic Amines; Preparation of NN-Dialkyl-N'-(o-nitrophenyl)hydrazines," *J.C. S. Perkin I* 1976:2216-2221, Royal Society of Chemistry (1976).

Linco Research, "Glucagon-Like Peptide-1 (Active) Elisa Kit 96-Well Plate (Cat. # EGLP-35K)," St. Charles, Missouri (Dec. 5, 2005).

Liu, D. and Liman, E.R., "Intracellular Ca2+ and the phospholipid PIP2 regulate the taste transduction ion channel TRPM5," *PNAS* 100:15160-15165, National Academy of Sciences (2003).

Margolskee, R.F., "Molecular Mechanisms of Bitter and Sweet Taste Transduction," *The Journal of Biological Chemistry* 277:1-4, The American Society for Biochemistry and Molecular Biology, Inc. (2002).

Margolskee, R.F., et al., "T1R3 and gustducin in gut sense sugars to regulate expression of Na+-glucose cotransporter 1," *PNAS* 104:15075-15080, National Academy of Sciences (Sep. 2007).

Muzychenko, G.F., et al., "Investigations in the Series of Substituted Butanolides and Butenolides," *J. Org. Chem. USSR* 17:404-408, Plenum Publishing Corporation (1981).

Pérez, C.A., et al., "A transient receptor potential channel expressed in taste receptor cells," *Nature Neuroscience* 5:1169-1176, Nature Publishing group (2002).

Prawitt, D., et al., "TRPM5 is a transient Ca2+-activated cation channel responding to rapid changes in [Ca2+]i," *PNAS* 100:15166-15171, National Academy of Sciences (2003).

Reinmann, F., et al., "Signaling Mechanisms Underlying the Release of Glucagon-Like Peptide 1," *Diabetes* 55:S78-S85, American Diabetes Association (Dec. 2006).

Rodighiero, P., et al., "Pyrrolocoumarin Derivatives as Potential Photoreagents Toward DNA," *J. Heterocyclic Chemistry* 24:1041-1043, Journal of Heterocyclic Chemistry (1987).

Sadrieh, N., et al., "Stability, Dose Uniformity, and Palatability of Three Counterterrorism Drugs-Human Subject and Electronic Tongue Studies," *Pharm Res* 22:1747-1756, Springer (Oct. 2005).

Schiffman, S.S., "Taste and Smell Losses in Normal Aging and Disease," *JAMA* 278:1357-1362, American Medical Association (1997).

Shirazi-Beechev, S., "Glucose sensing and regulation of intestinal glucose absorption," Abstract 245, Sarasota, Florida (Apr. 25-29, 2007).

Sørensen, L.B., et al., "Effect of sensory perception of foods on appetite and food intake: A review of studies on human," *International Journal of Obesity* 27:1152-1166, Nature Publishing Group (2003).

Talavera, K., et al., "Heat activation of TRPM5 underlies thermal sensitivity of sweet taste," *Nature* 438:1022-1025, Nature Publishing Group (2005).

Tschantz, M.A., et al.," 4-Ketoundecanoic Acid," *Organic Syntheses, Coll.* 9:530-533, Organic Syntheses, Inc. (1998).

Turton, M.D., et al., "A role for glucagon-like peptide-1 in the central regulation of feeding," *Nature* 379:69-72, Nature Publishing Group (1996).

UK Prospective Diabetes Study (UKPDS) Group, Intensive blood-glucose control with sulphonylureas or insulin compared with conventional treatment and risk of complications in patients with type 2 diabetes (UKPDDS 33), *Lancet* 352:837-853, Elsevier Science Ltd. (1998).

Ullrich, N. D., et al., "Comparison of functional properties of the Ca2+-activated cation channels TRPM4 and TRPM5 from mice," *Cell Calcium* 37:267-278, Elsevier Science Ltd. (2005).

Vissink, A., et al., Prevention and Treatment of the Consequences of Head and Neck Radiotherapy, *Crit. Rev. Oral Biol. Med.* 14:213-225, International Association for Dental Research (2003).

Vissink, A., et al., Oral Sequelae of Head and Neck Radiotherapy, *Crit Rev Oral Biol Med* 14:199-212, International & American Associations for Dental Research. (2003).

Wang, Z., et al., "Glucagon-like Peptide-1 is a Physiological Incretin in Rat," *J. Clin. Invest.* 95:417-421, The American Society for Clinical Investigation, Inc. (1995).

Wyrzykiewicz, E. and Prukala, D., "New Isomeric N-Substituted Hydrazones of ortho, meta and para Hydroxybenzaldehydes," *Polish J. Chem.* 72:694-702, Panstwowe Wydawnictwo Naukowe (1998).

Yamaguchi, S. and Ninomiya, K., "The Use and Utility of Glutamates as Flavoring Agents in Food," *J. Nutr.* 130:921S-926S, American Society for Nutritional Sciences (2000).

Zhang, Y., et al., "Coding of Sweet, Bitter, and Umami Tastes: Different Receptor Cells Sharing Similar Signaling Pathways," *Cell* 112:293-301, Cell Press (2003).

International Search Report for International Application No. PCT/US08/01445, mailed on Sep. 15, 2008, ISA/US, Alexandria, VA, U.S.A.

Office Action mailed Oct. 5, 2009, in U.S. Appl. No. 11/592,228, inventors Bryant et al., filed Nov. 3, 2006.

Damak, S., et al., "Trpm5 null mice respond to bitter, sweet, and umami compounds," *Chem. Senses.* 31(3): 253-264, Oxford University Press, England (Mar. 2006; Epub Jan. 2006).

International Preliminary Report on Patentability for International Application No. PCT/US06/42988, issued on Sep. 2, 2008, The International Bureau of WIPO, Geneva, Switzerland.

International Search Report for International Application No. PCT/US06/42988, mailed on Aug. 5, 2008, ISA/USA, Virginia, U.S.A.

Liu, D., et al., "Extracellular Acid Block and Acid-enhanced Inactivation of the $Ca^{2+}$ -activated Cation Channel TRPM5 Involve Residues in the S3-S4 and S5-S6 Extracellular Domains," *J Biol Chem* 280: 20691-20699, The American Society for Biochemistry and Molecular Biology, Inc. (May 2005).

Supplementary European Search Report for European Patent Application No. 06 82 7464, The Hague, Netherlands, search completed on Jun. 23, 2009.

Written Opinion of the International Searching Authority for International Application No. PCT/US06/42988, mailed on Aug. 5, 2008, ISA/USA, Virginia, U.S.A.

English language Abstract for European Patent Publication No. EP 0 294 258 Al, European Patent Office, espacenet database—Worldwide, (1988).

Office Action mailed Oct. 7, 2010, in U.S. Appl. No. 11/592,228, inventors Bryant et al., filed Nov. 3, 2006.

\* cited by examiner

Example 4 Increases Insulin in a Glucose Dependent Manner in Contrast to Tolbutamide Both compounds at near maximum levels of insulin stimulation The TRPM5 Ion Channel Inhibitor, Example 4, Blocks Ca++ Activated Current in Beta TC6 Cells

USE OF A TRPM5 INHIBITOR TO REGULATE INSULIN AND GLP-1 RELEASE

CROSS-REFERENCE TO RELATED APPLICATIONS

This application claims the benefit under 35 U.S.C. §119(e) of U.S. Provisional Application No. 60/887,996, filed Feb. 2, 2007, and U.S. Provisional Application No. 61/016,394, filed Dec. 21, 2007; the entireties of which are incorporated by reference.

BACKGROUND OF THE INVENTION

1. Field of the Invention

The present invention relates to methods of enhancing insulin release, enhancing GLP-1 release, increasing insulin sensitivity, increasing insulin gene expression, decreasing gastric secretion, decreasing gastric emptying, and decreasing glucagon secretion by administering to a subject an effective amount of a TRPM5 inhibitor, such as a compound according to Formula I as defined herein. The present invention also relates to methods of treating diabetes mellitus, insulin resistance syndrome, hyperglycemia, and obesity by administering to a subject an effective amount of a TRPM5 inhibitor, such as a compound according to Formula I as defined herein. This invention further relates to methods of using such TRPM5 inhibitors in the treatment of the above diseases in an animal, preferably a human or other mammal in need thereof, and to pharmaceutical compositions useful thereof. These and additional aspects of the present invention are described in further detail herein.

2. Background Art

Diabetes mellitus is a syndrome characterized by abnormal insulin production, increased urinary output and elevated blood glucose levels. There are two major subclasses which can be described based on the level of insulin production by a person's pancreatic beta cells. One is insulin-dependent diabetes mellitus (IDDM, or Type 1), formerly referred to as juvenile onset diabetes since it was evident early in life. In Type 1 Diabetes, little or no insulin is produced as the pancreatic beta cells have been destroyed by the body's own immune system. Between 5-10% of all diabetics have IDDM (American Diabetes Association. Diabetes 1996 Vital Statistics. Rockville, Md.: American Diabetes Association, 1996.) The other type is non-insulin dependent diabetes mellitus (NIDDM, or Type 2), often referred to as maturity-onset diabetes. In Type 2 Diabetes, pancreatic beta cells produce insulin but not in sufficient quantities to maintain healthy blood glucose levels. Type 2 Diabetes results from the deterioration in the molecular machinery that mediates the effectiveness of insulin function on cells (e.g., insulin resistance and inadequate insulin release). Between 90-95% of all diabetics are NIDDM (Harris, M. I., Cowie, C. C., Stem, M. P. eds. *Diabetes in America,* 2nd. ed. National Institutes of Health. National Institute of Diabetes and Digestive and Kidney Diseases. NIH Publication No. 95-1468, 1995).

Type 2 diabetes is a significant healthcare problem, and its incidence is on the rise. Between 1990 and 1998, the prevalence of NIDDM in the United States increased by 33 percent, to about 13 million persons. An additional 5 million persons are presumed to have undiagnosed NIDDM, while another 14 million persons have impaired glucose tolerance. Direct medical costs associated with diabetes were $44 billion in 1997, due mainly to hyperglycemia-related diabetic complications, including diabetic angiopathy, atherosclerosis, diabetic nephropathy, diabetic neuropathy, and diabetic ocular complications such as retinopathy, cataract formation, and glaucoma.

Resistance to the metabolic actions of insulin is one of the key features of non-insulin dependent diabetes. Insulin resistance is characterized by impaired uptake and utilization of glucose in insulin-sensitive target organs, for example, adipocytes and skeletal muscle, and by impaired inhibition of hepatic glucose output. The functional insulin deficiency and the failure of insulin to suppress hepatic glucose output result in fasting hyperglycemia. Pancreatic beta-cells compensate for the insulin resistance by secreting increased levels of insulin. However, the beta-cells are unable to maintain this high output of insulin, and, eventually, the glucose-induced insulin release falls, leading to the deterioration of glucose homeostasis and to the subsequent development of overt diabetes.

Other metabolic disorders associated with impaired glucose utilization and insulin resistance include insulin resistance syndrome (hereinafter "IRS"), which refers to the cluster of manifestations that include insulin resistance; hyperinsulinemia; non insulin dependent diabetes mellitus (NIDDM); arterial hypertension; central (visceral) obesity; and dyslipidemia.

The primary goal of insulin resistance therapy and thus diabetes therapy is to lower blood glucose levels so as to prevent acute and long-term disease complications. For some persons, modified diet and increased exercise may be successful therapeutic options for achieving the goal of glucose control. When modified diet and increased exercise are not successful, drug therapy using oral antidiabetic agents is initiated.

Control of insulin release is very important, as there are many living diabetes patients whose pancreas is not operating correctly. In some types of diabetes, the total level of insulin is reduced below that required to maintain normal blood glucose levels. In others, the required insulin is generated but only at an unacceptable delay after the increase in blood glucose levels. In others, the body is, for some reason, resistant to the effects of insulin. If the diabetes is poorly controlled, it can lead to diabetic complications. Diabetic complications are common in Type 2 patients with approximately 50% suffering from one or more complications at the time of diagnosis (Clark, C. M., Vinicor, F. *Introduction: Risks and benefits of intensive management in non-insulin-dependent diabetes mellitus.* The Fifth Regensrief Conference. Ann Intern Med, 124(1, pt 2), 81-85, 1996.).

Exogenous insulin by injection is used clinically to control diabetes but suffers from several drawbacks. Insulin is a protein and thus cannot be taken orally due to digestion and degradation but must be injected. It is not always possible to attain good control of blood sugar levels by insulin administration. Insulin resistance sometimes occurs, requiring much higher doses of insulin than normal. Another shortcoming of insulin is that, while it may control hormonal abnormalities, it does not always prevent the occurrence of complications such as neuropathy, retinopathy, glomerulosclerosis, and cardiovascular disorders. Insulin regulates glucose homeostasis mainly by acting on two targets tissues: liver and muscle. Liver is the only site of glucose production, and skeletal muscle is the main site of insulin mediated glucose uptake.

There are several classes of drugs that are useful for treatment of Type 2 Diabetes: 1) insulin releasers, which directly stimulate insulin release, carrying the risk of hypoglycemia; 2) prandial insulin releasers, which potentiate glucose-induced insulin release and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; and 5) insulin injections, which are often necessary in the later stages of Type 2 Diabetes when the islets have failed under chronic hyperstimulation. The effectiveness of current oral antidiabetic therapies is limited, in part, because of poor or limited glycemic control, or poor patient compliance due to unacceptable side effects. These side effects include edema weight gain, hypoglycemia, and even more serious complications.

Insulin secretagogues are standard therapy for Type 2 diabetics who have mild to moderate fasting hyperglycemia. Insulin secretors include sulfonylureas (SFUs) and the non-sulfonylureas, nateglinide and pepaglinide. The sulfonylureas are subdivided into two subcategories: the first generation agents, e.g., tolbutamide, chlorpropamide, tolazamide, acetohexamide, and the second generation agents, e.g., glyburide (glibenclamide), glipizide and gliclazide.

The insulin secretagogues have limitations that include a potential for inducing hypoglycemia, weight gain, and high primary and secondary failure rates. Approximately 10 to 20% of initially treated patients fail to show a significant treatment effect (primary failure). Secondary failure is demonstrated by an additional 20-30% loss of treatment effect after six months of treatment with insulin secretagogues. Insulin treatment is required in 50% of the insulin secretagogues responders after 5-7 years of therapy (Scheen et al., *Diabetes Res. Clin. Pract.* 6:533 543, 1989). Nateglinide and pepaglinide are short-acting drugs that need to be taken three times a day. They are used only for the control of postprandial glucose and not for control of fasting glucose.

Treatment with sulfonylureas increases the risk of hypoglycemia (or insulin shock), which occurs if blood glucose levels fall below normal (UKPDS Group. UK Prospective Diabetes Study 33: Intensive blood-glucose control with sulphonylureas or insulin compared with conventional treatment and risk of complications in patients with type 2 diabetes. *Lancet,* 352, 837-853 (1998).

Treatment with a gastrointestinal protein hormone is potentially another way to treat diabetes mellitus. Gastrointestinal protein hormones, including, but not limited to, glucose-dependent insulinotropic polypeptide (GIP) and glucagon-like peptide-1 (GLP-1), stimulate insulin synthesis and secretion from the beta cells of the islets of Langerhans after food intake, thereby lowering blood glucose levels. Further, oral administration of glucose has long been known to increase insulin secretion more than intravenous glucose administration dose, despite similar plasma glucose concentration. Scow et al., *Am J. Physiol.,* 179(3):435-438 (1954). Such an effect, called the incretin effect, provides the basis for regulating glucose disposal and treatment of diabetes and its related disease.

The most potent gastrointestinal protein hormone is GLP-1, which is initially a 37-amino acid peptide and a product of proglucagon. A subsequent endogenous cleavage between the sixth and seventh position produces the biologically active GLP-1 (7-37) peptide. GLP-1 is secreted from the L-type enteroendocrine cells in the luminal surface of the gut upon glucose intake. GLP-1 acts through a G-protein-coupled cell-surface receptor (GLP-1R) and is regulated by T1R taste receptors and gustducin. See Kokrashvili et al. AChemS XXIX Abstract, 246 (2007). Studies have shown that α-gustducin couples sweet receptor T1R3 in sugar- and sweetener-stimulated secretion of GLP-1 from the L-type enteroendocrine cells. See Jang et al. *Proc. Natl. Acad. Sci. USA,* 104(38): 15069-15074; Margolskee, et al., Proc. Natl. Acad. Sci. USA 104(38):15075-15080 (2007). GLP-1 possesses several physiological functions; for example, 1) it stimulates insulin synthesis from the pancreatic islet cells in a glucose-dependent manner, thereby lowering blood glucose levels; 2) it decreases glucagon secretion from the pancreas; 3) it increases beta cell mass and insulin gene expression; 4) it inhibits gastric secretion and emptying; 5) it dose-dependently inhibits food intake by increasing satiety; and 6) it promotes weight loss. Several roles for GLP-1 are described by U.S. Pat. No. 6,583,118, U.S. Pat. No. 7,211,557, U.S. Patent Appl. Pub. No. 2005/0244810, Deacon, *Regulatory Peptides* 128: 117-124 (2005); and Turton et al., *Nature,* 379, 69-72 (1996).

SUMMARY OF THE INVENTION

Accordingly, an antidiabetic agent which can be used to either directly stimulate insulin secretion or indirectly stimulate insulin by increasing the level of GLP-1 secretion would be desirable for the treatment of diabetes and its related illnesses.

The invention is directed to the use of a TRPM5 inhibitor for enhancing the secretion of insulin. Additionally, according to the invention, a TRPM5 inhibitor can be used to treat conditions, such as diabetes mellitus and others, that respond positively to an increase in insulin.

In one embodiment, methods are disclosed for treating diabetes mellitus comprising administering to a subject a compound according to Formula I as defined herein.

Also provided is a method of treating, preventing or controlling hyperglycemia and/or insulin resistance in a mammal comprising administering to a subject in need thereof an effective amount of a TRPM5 inhibitor, such as a compound of Formula I.

In one aspect of this embodiment, the diabetes mellitus is Type 2 diabetes mellitus, or maturity onset diabetes of the young. In another aspect, a TRPM5 inhibitor enhances insulin release, such as insulin release stimulated by glucose. In other aspects, the compounds enhance insulin release stimulated by a supraphysiological glucose concentration, and do not enhance insulin release in the presence of a physiological glucose concentration.

Also provided are pharmaceutical compositions for treating diabetes mellitus, insulin resistance syndrome and hyperglycemia comprising a TRPM5 inhibitor, such as a compound of Formula I. These and other aspects of the invention are described in more detail herein.

The present invention is also directed to a method of enhancing GLP-1 release from a cell, comprising contacting said cell with an effective amount of one or more TRPM5 inhibitors. In certain embodiments, the TRPM5 inhibitor is a compound of Formula I.

The present invention is further directed to a method of decreasing gastric secretion and emptying, a method of inhibiting food intake, a method of decreasing glucagon secretion, a method of enhancing insulin sensitivity, increasing insulin gene expression, and a method of treating obesity in a mammal, comprising administering to said mammal in need thereof an effective amount of one or more TRPM5 inhibitors. In certain embodiments, the TRPM5 inhibitor is a compound of Formula I.

BRIEF DESCRIPTION OF THE DRAWINGS/FIGURES

FIG. 1A shows the stimulation of insulin synthesis and release by β-TC6 cells under varying conditions (A-H). The conditions (A-H) are as follows: A) KRBB buffer; B) KRBB and DMSO (vehicle); C) KRBB, DMSO, and LG Compound A, a compound known to enhance TRPM5 (100 µM); D) KRBB, DMSO, and Example 4 (100 µM); E) KRBB and 2 mM glucose; F) KRBB, 2 mM glucose, and DMSO; G) KRBB, DMSO, 2 mM glucose, and LG Compound A (100 µM); H) KRBB, DMSO, 2 mM glucose, and Example 4. FIG. 1B illustrates the same results subtracted for KRBB (buffer) response.

FIG. 2 provides a dose-response curve for the stimulation of insulin secretion by β-TC6 cells by the compound of Example 4 in the presence of glucose (2 mM).

FIG. 3 compares the effect of glucose concentration on the stimulation of insulin release for the compound of Example 3 and tolbutamide. As FIG. 3 illustrates, the compound of Example 3 increases insulin secretion in a glucose-dependent manner in contrast to tolbutamide, which is not sensitive to glucose levels.

Figure 1A:
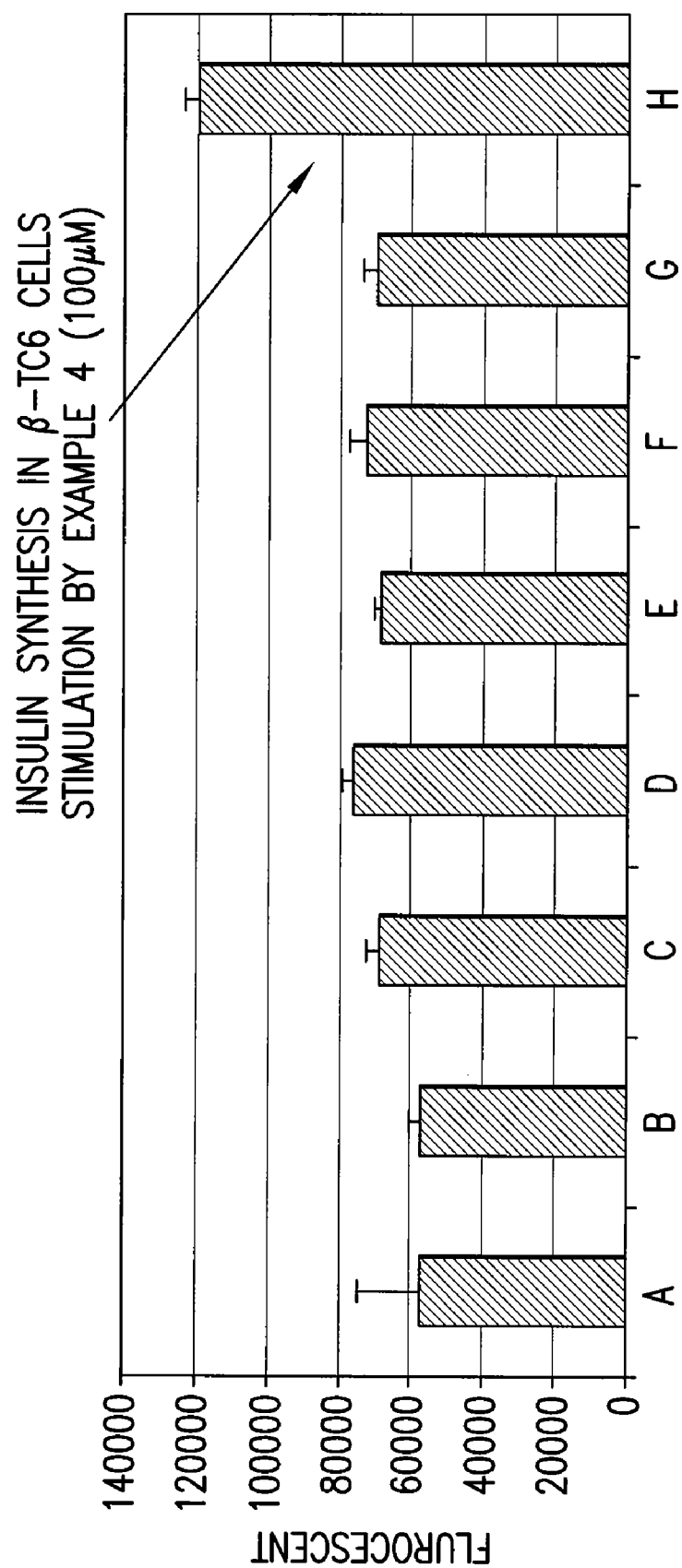
Figure 1B:
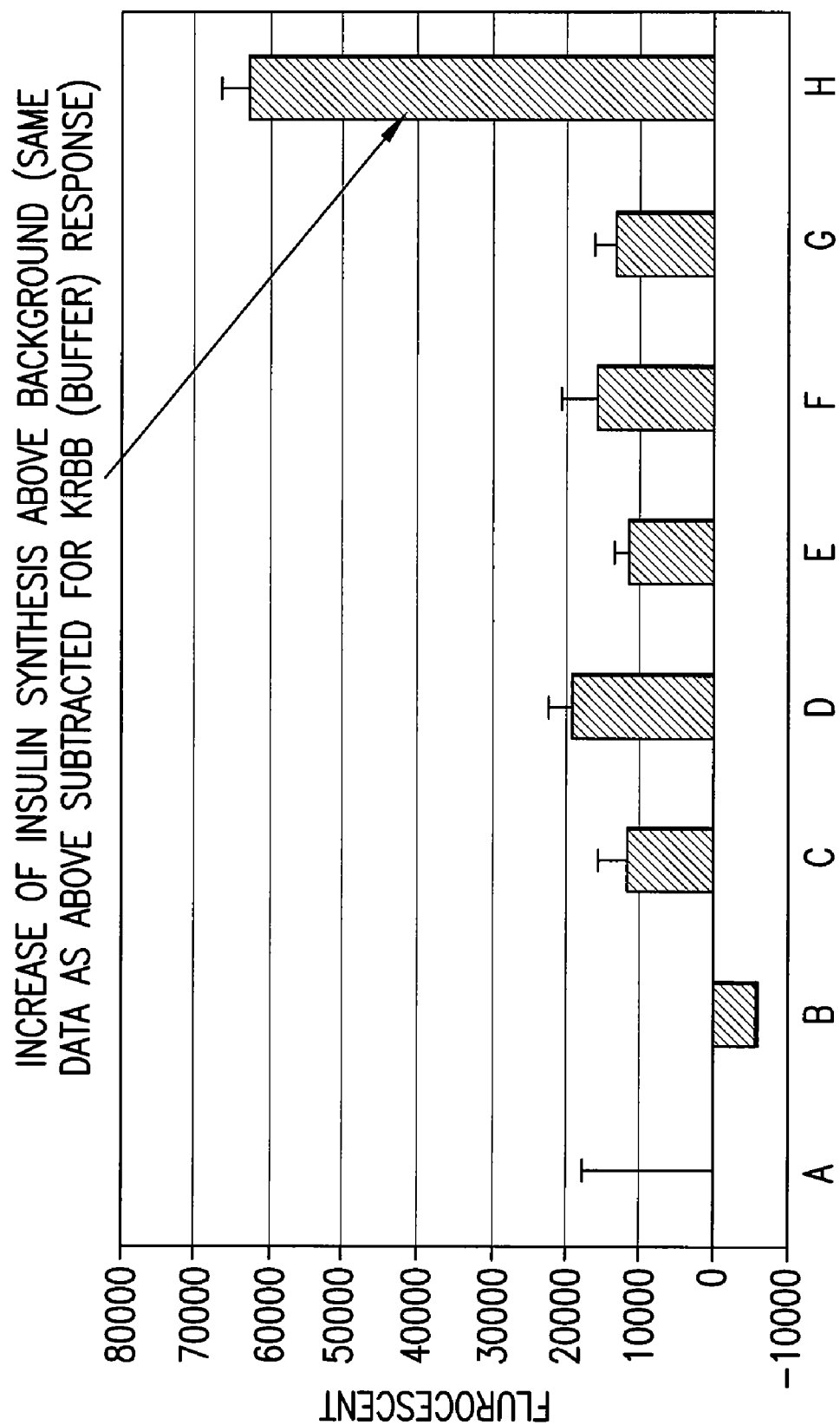
Figure 2:
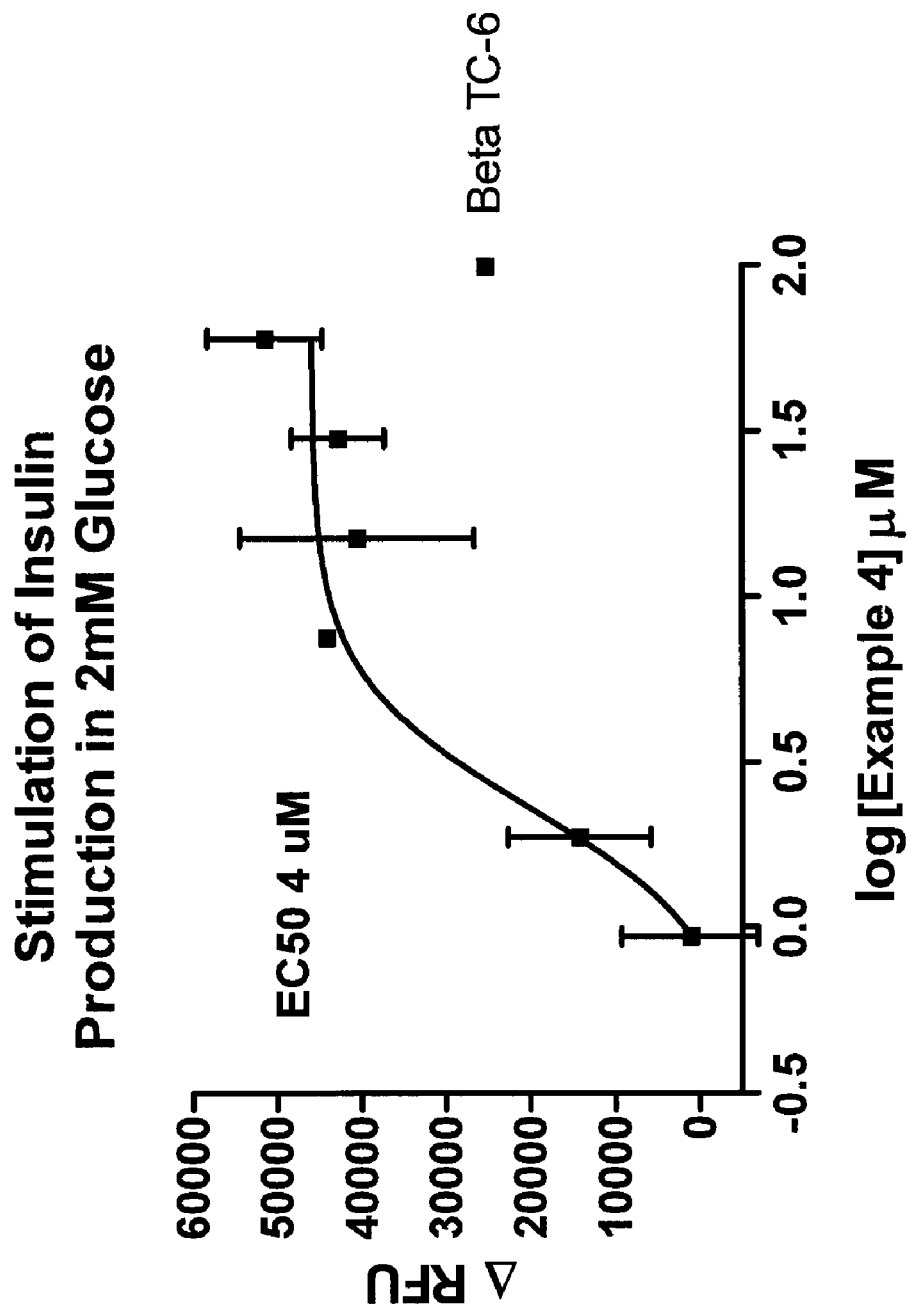
Figure 3:
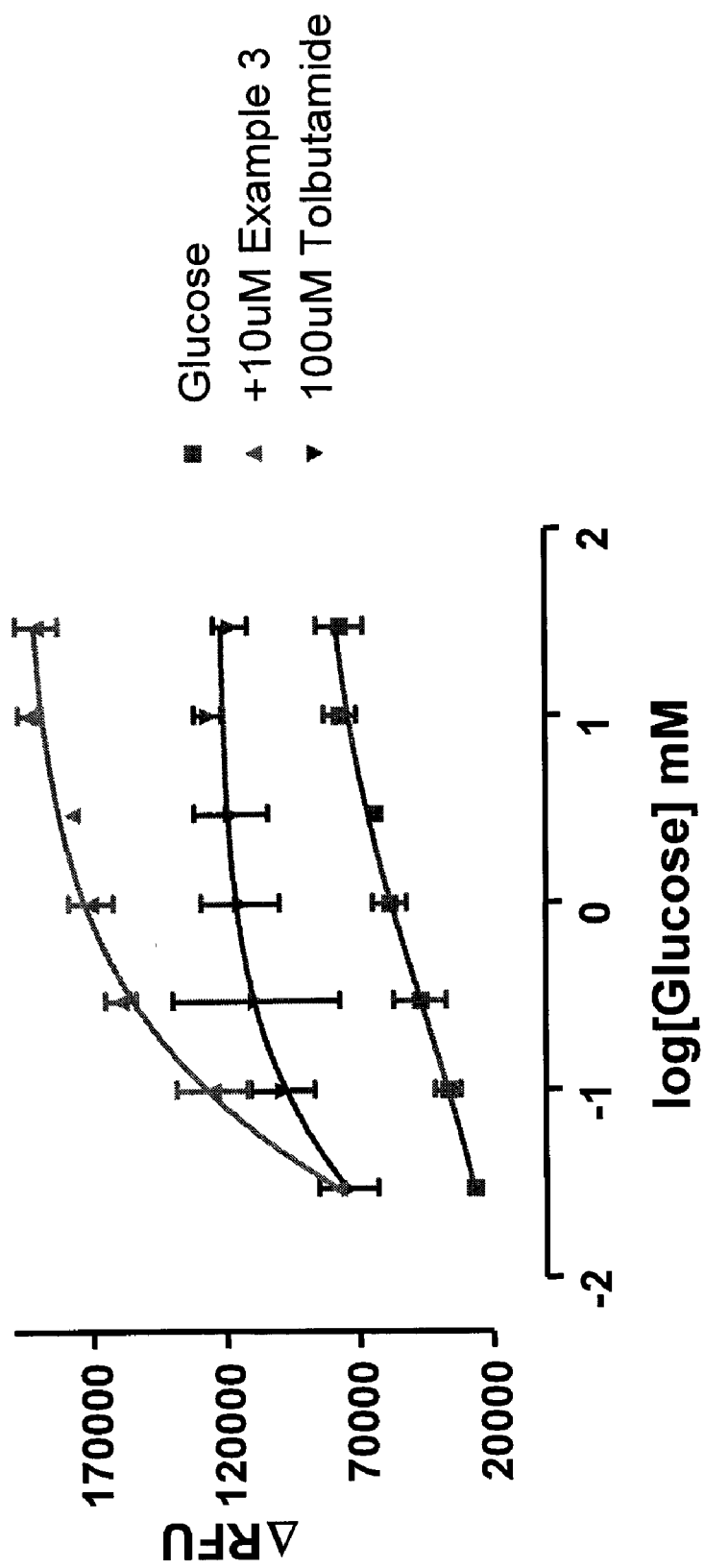
Figure 4:
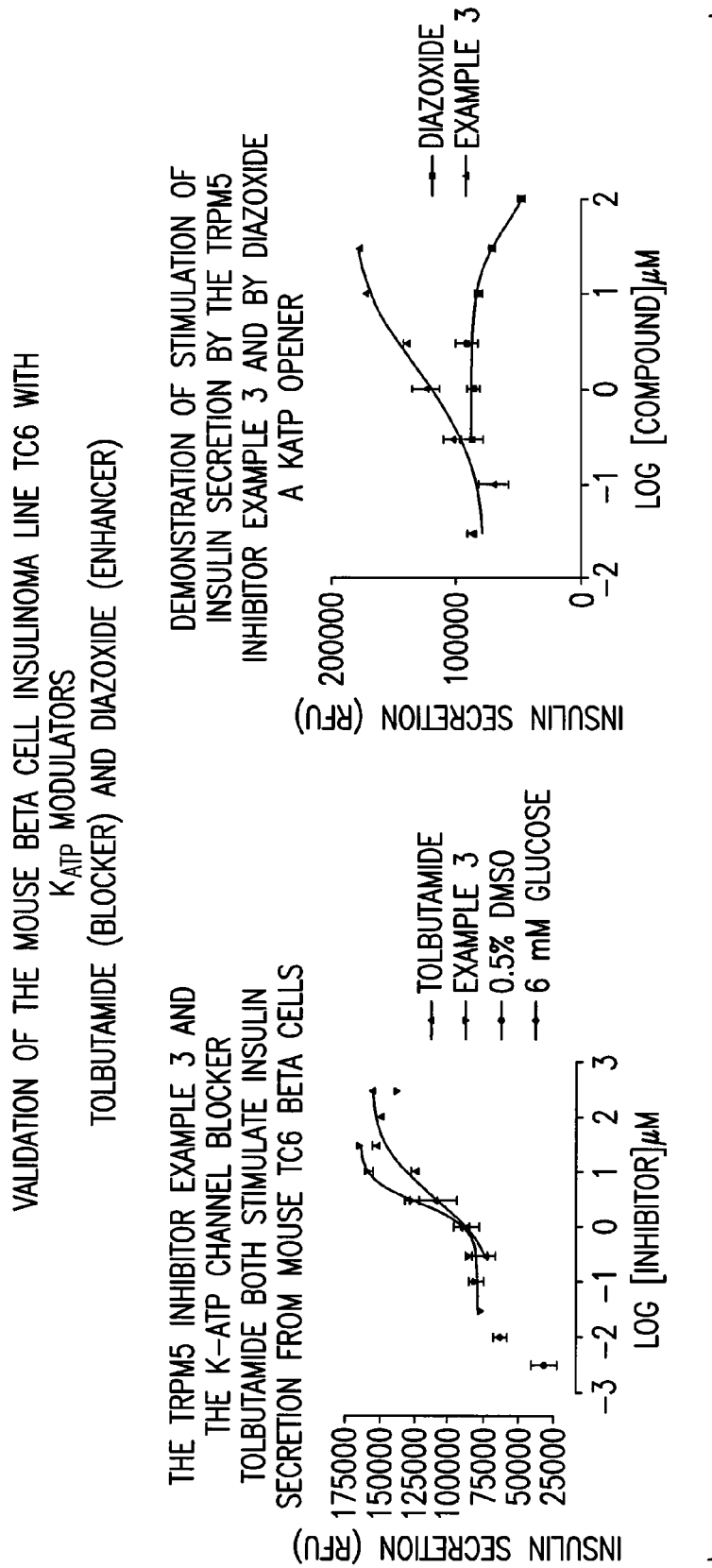
FIG. 4 shows the effects of the compound of Example 3, tolbutamide, and diazoxide on insulin secretion by the mouse beta cell insulinoma line TC6.
Figure 5:
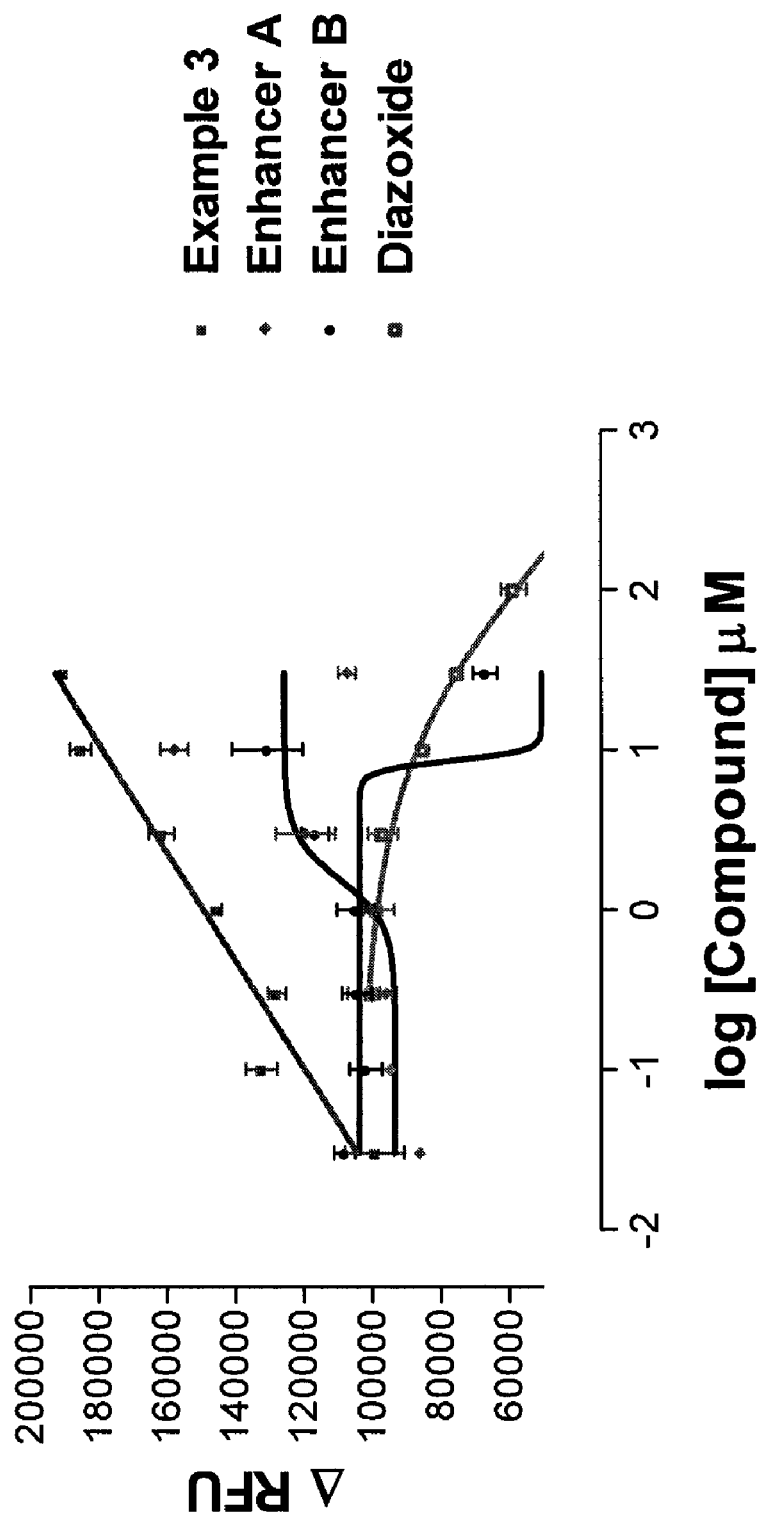
FIG. 5 illustrates that certain TRPM5 enhancers are ineffective at stimulating insulin secretion and also illustrates that the compound of Example 3 increases insulin secretion.
Figure 6:
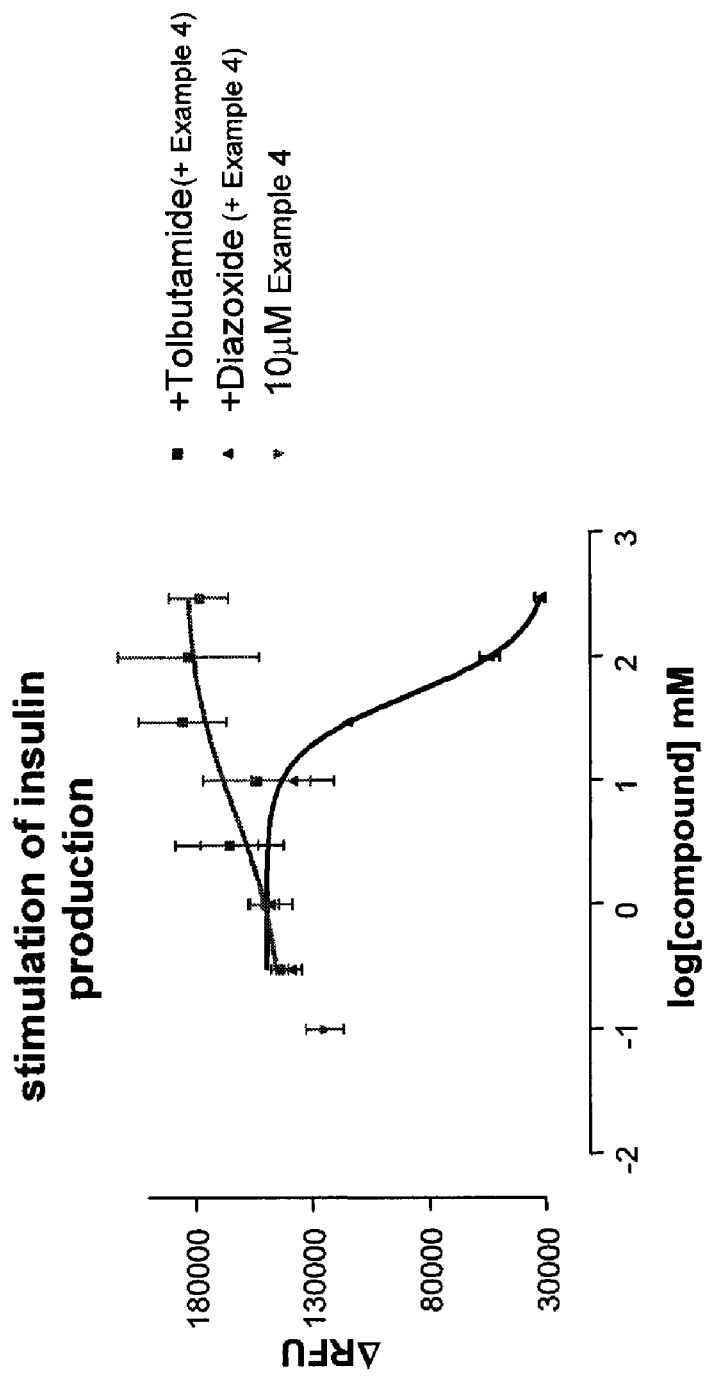
FIG. 6 illustrates the additive effects of Example 4 and tolbutamide on insulin secretion.
Figure 7:
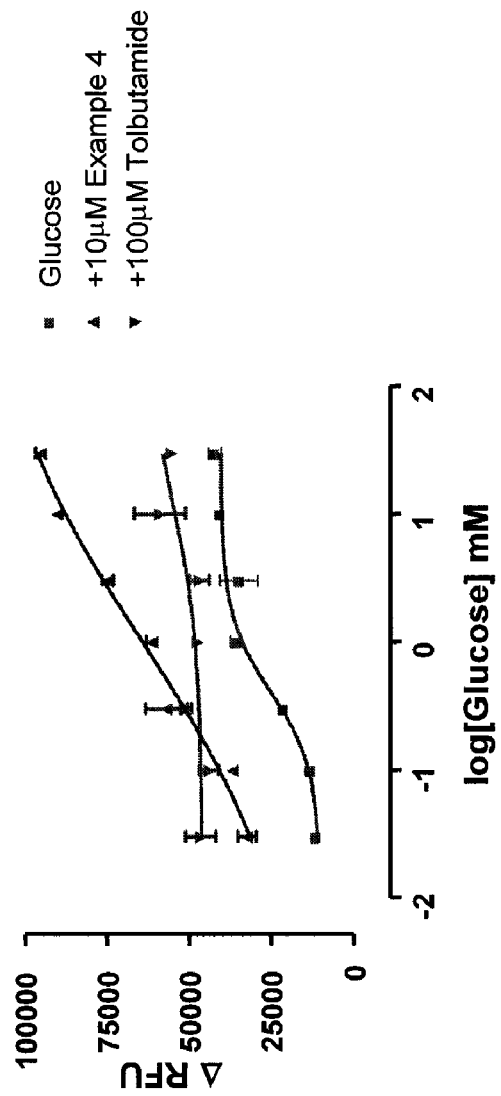

FIG. 7 demonstrates that the compound of Example 4 increases insulin secretion in a glucose-dependent manner in contrast to tolbutamide.

Figure 8:
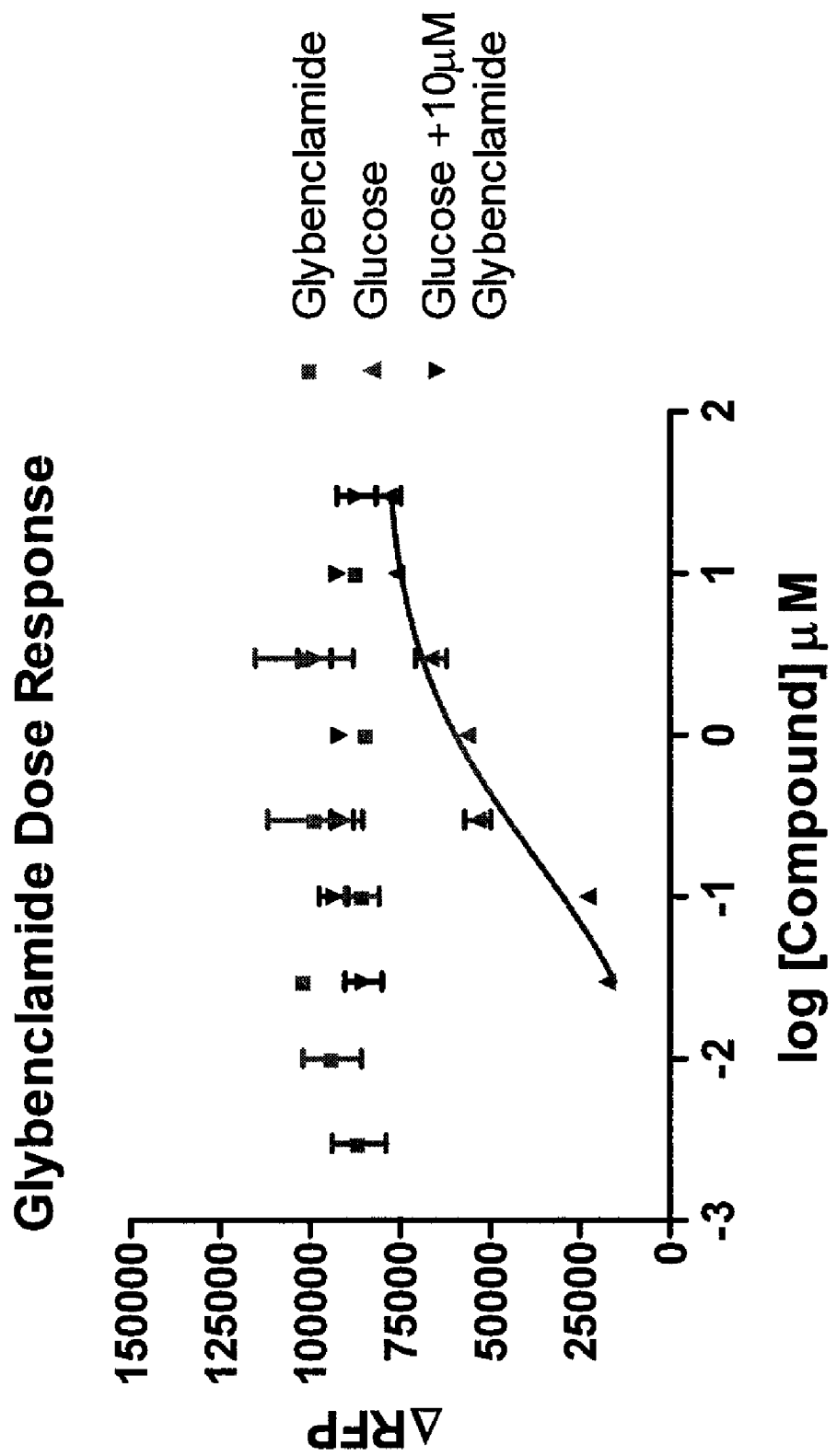

FIG. 8 illustrates the dose-response of glybenclamide for insulin secretion.

Figure 9:
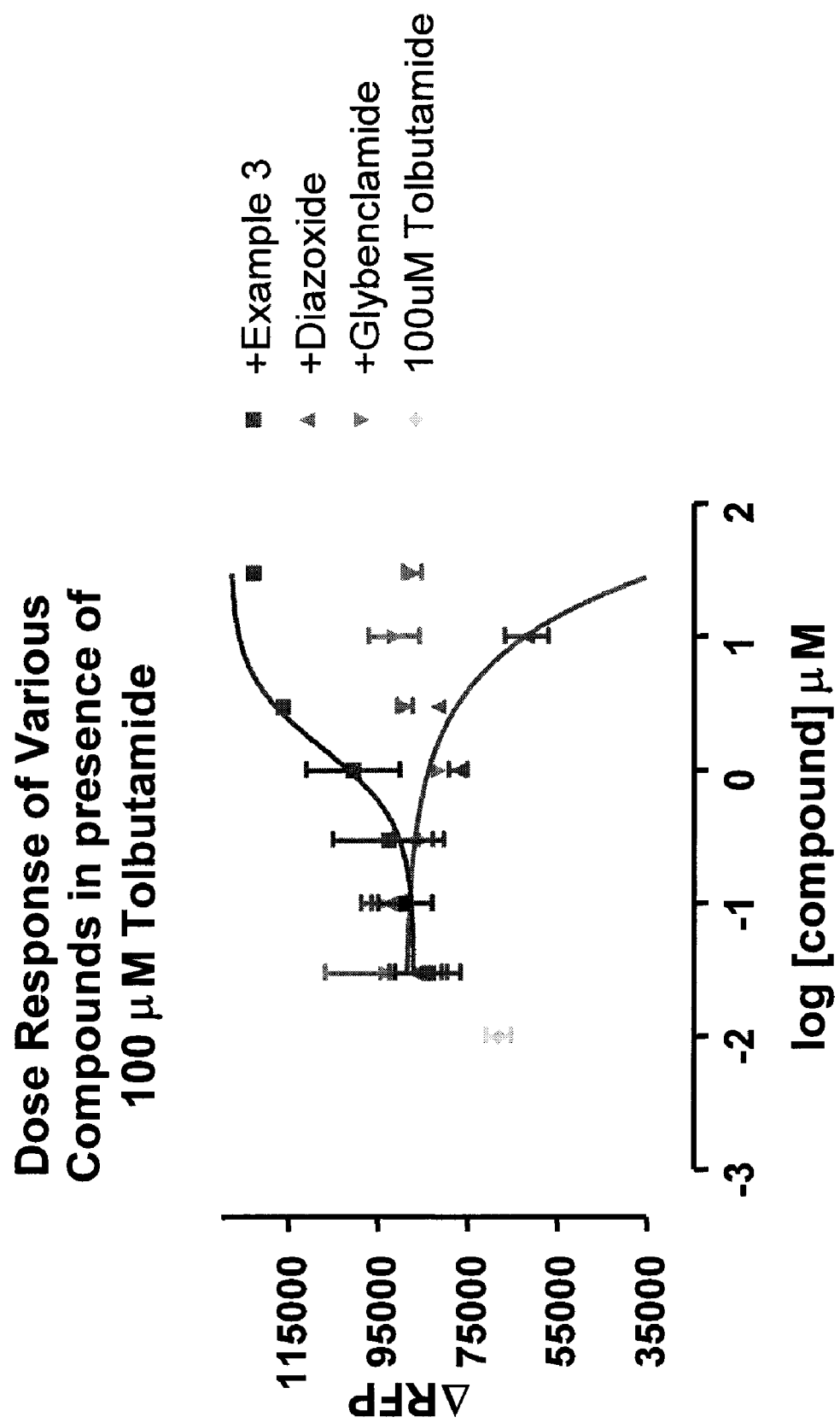

FIG. 9 illustrates the dose response of various compounds in the presence of 100 µM tolbutamide.

Figure 10:
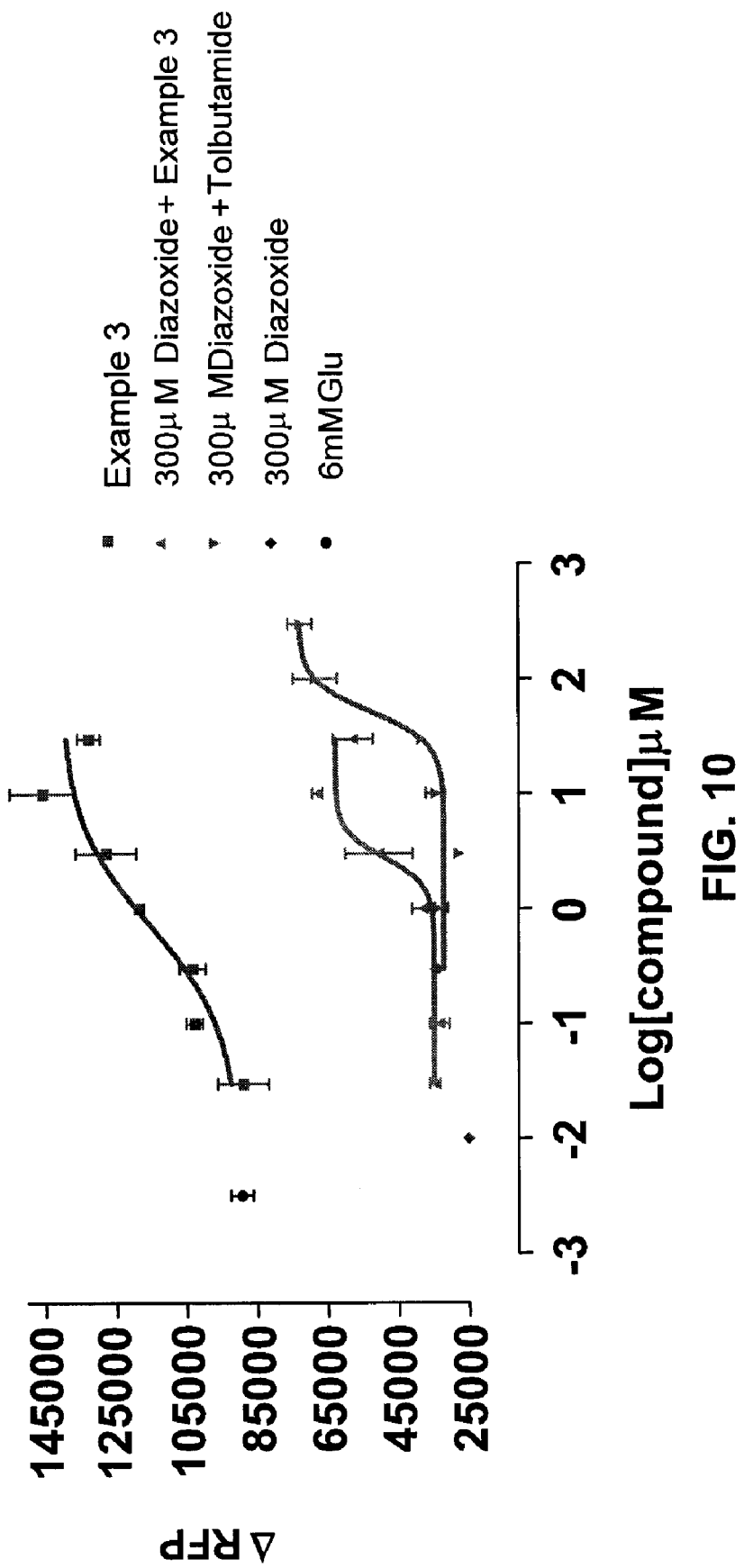

FIG. 10 provides the dose response of various compounds in the presence of 300 µM diazoxide.

Figure 11:
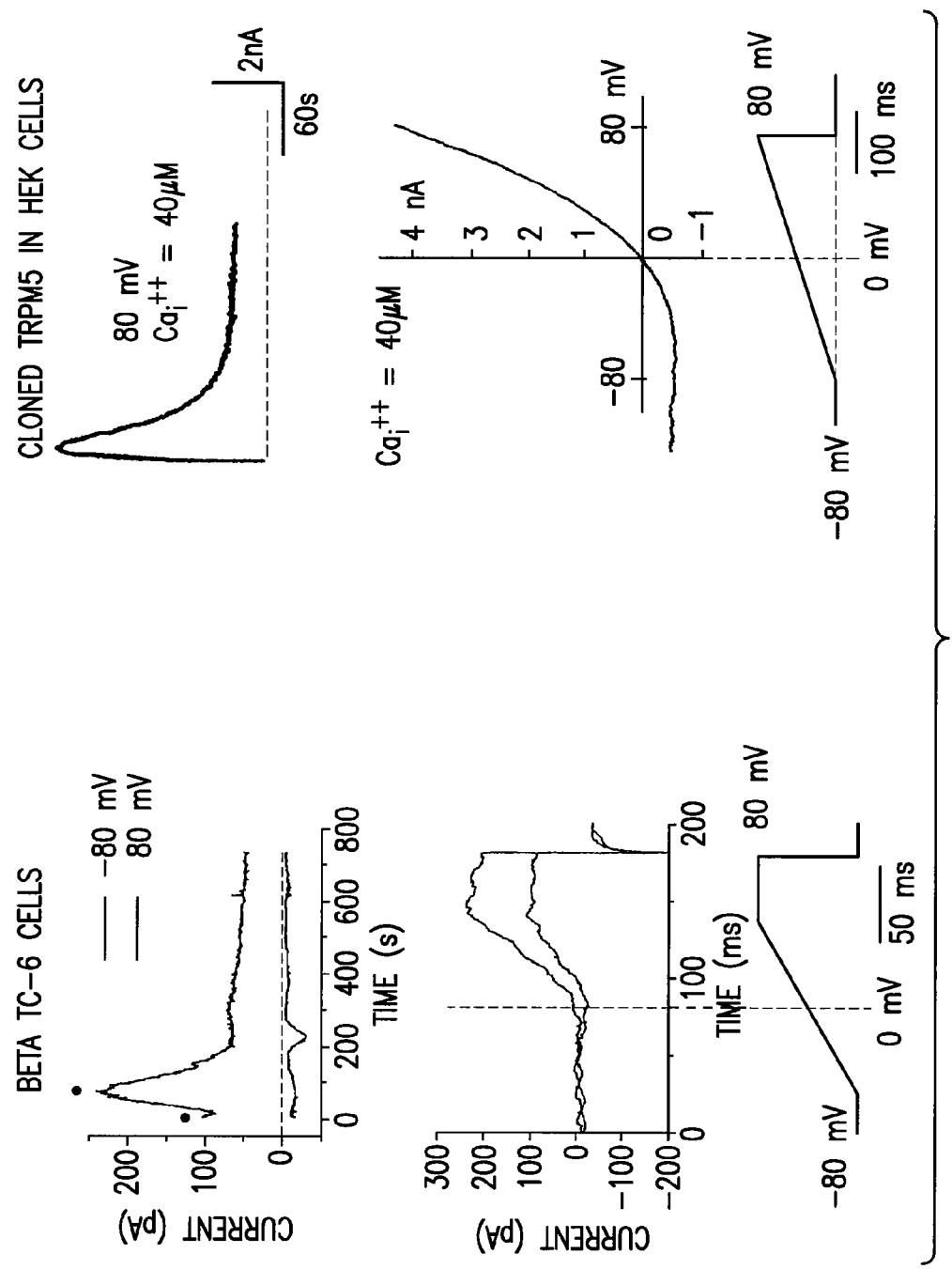

FIG. 11 provides the graphical results of experiments that show the similarity between the calcium-activated ion channel current in Beta TC-6 cells and HEK cells cloned with TRPM5.

Figure 12:
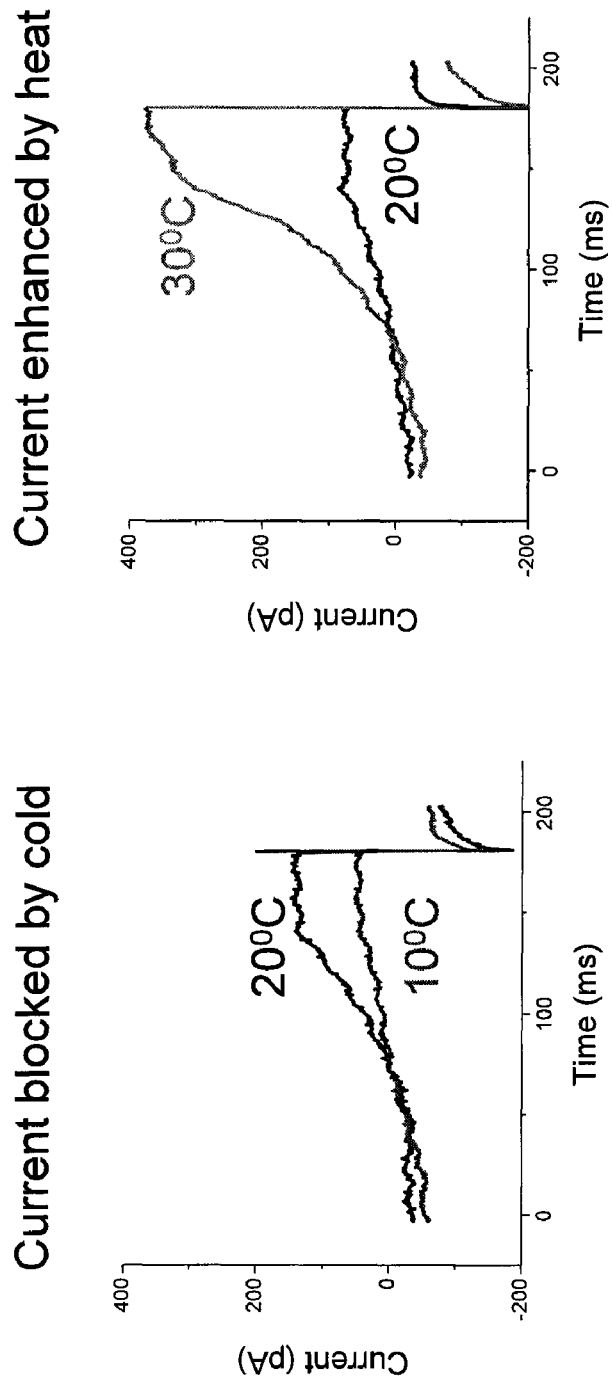

FIG. 12 illustrates the similarity in the temperature dependence between the calcium-activated current in Beta TC-6 cells and TRPM5 channels, as reported by Talavera, et al., *Nature* 438:1022-1025 (2005).

Figure 13:
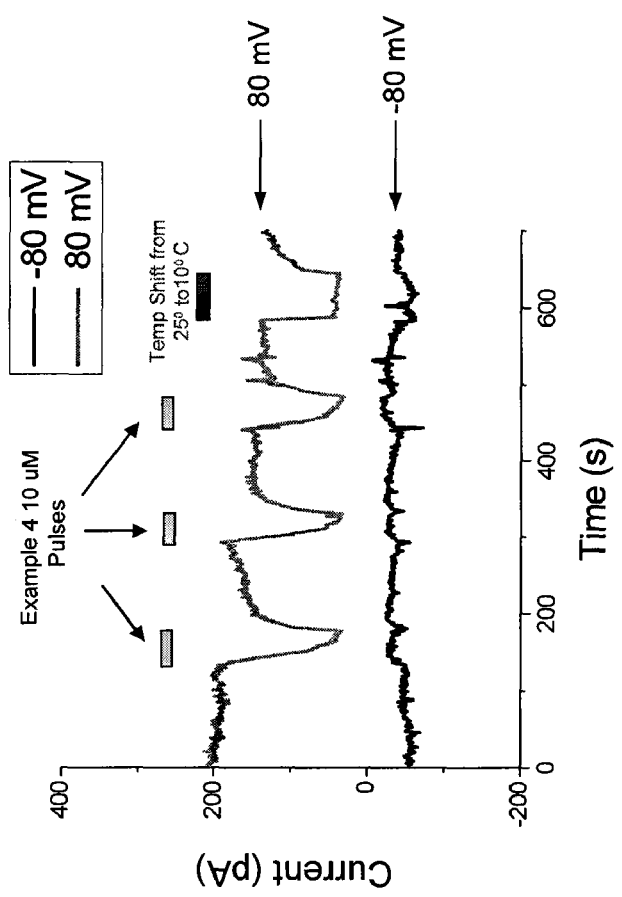

FIG. 13 provides a graph of the current versus time for a calcium-activated current in Beta TC6 cells and shows the inhibition of the current due to pulsed doses of the compound of Example 4.

Figure 14:
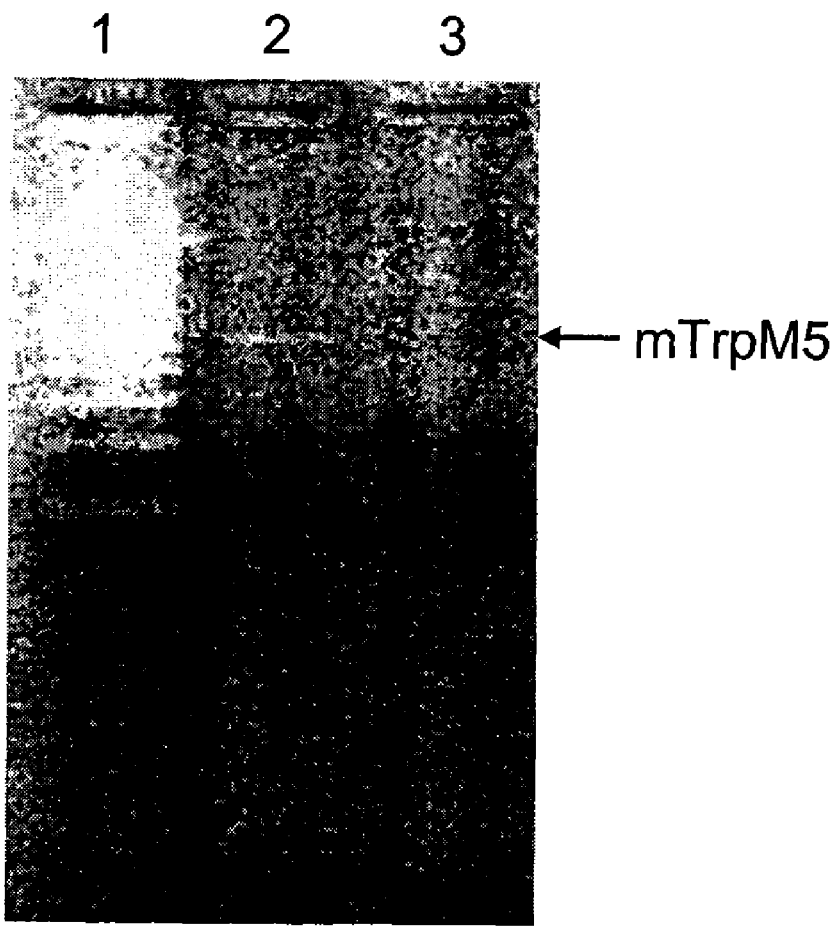

FIG. 14 provides a copy of a gel electrophoresis that shows the presence of mTRPM5 in mouse Beta TC-6 cells, as determined by RT-PCR analysis.

Figure 15:
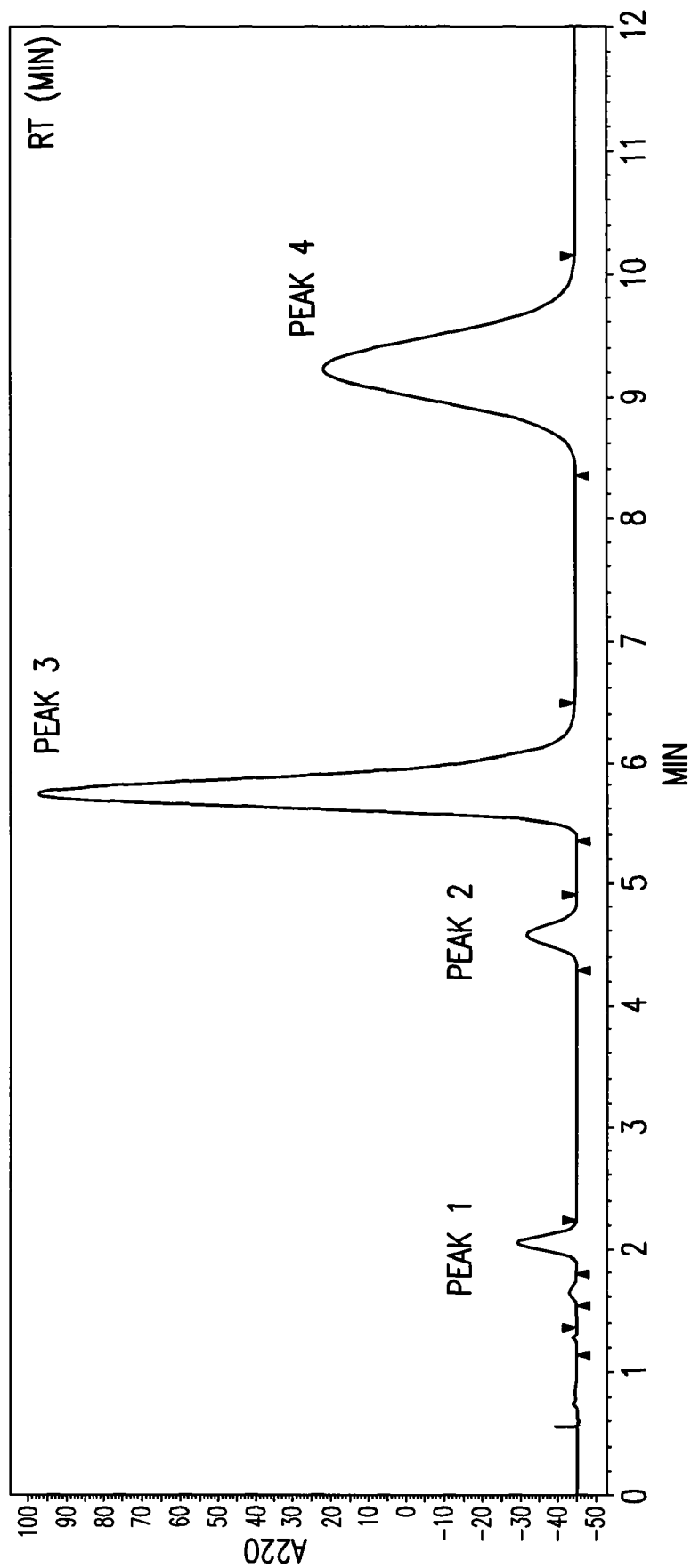

FIG. 15 provides the results of the HPLC separation of the enantiomers of the compound of Example 4.

Figure 16:
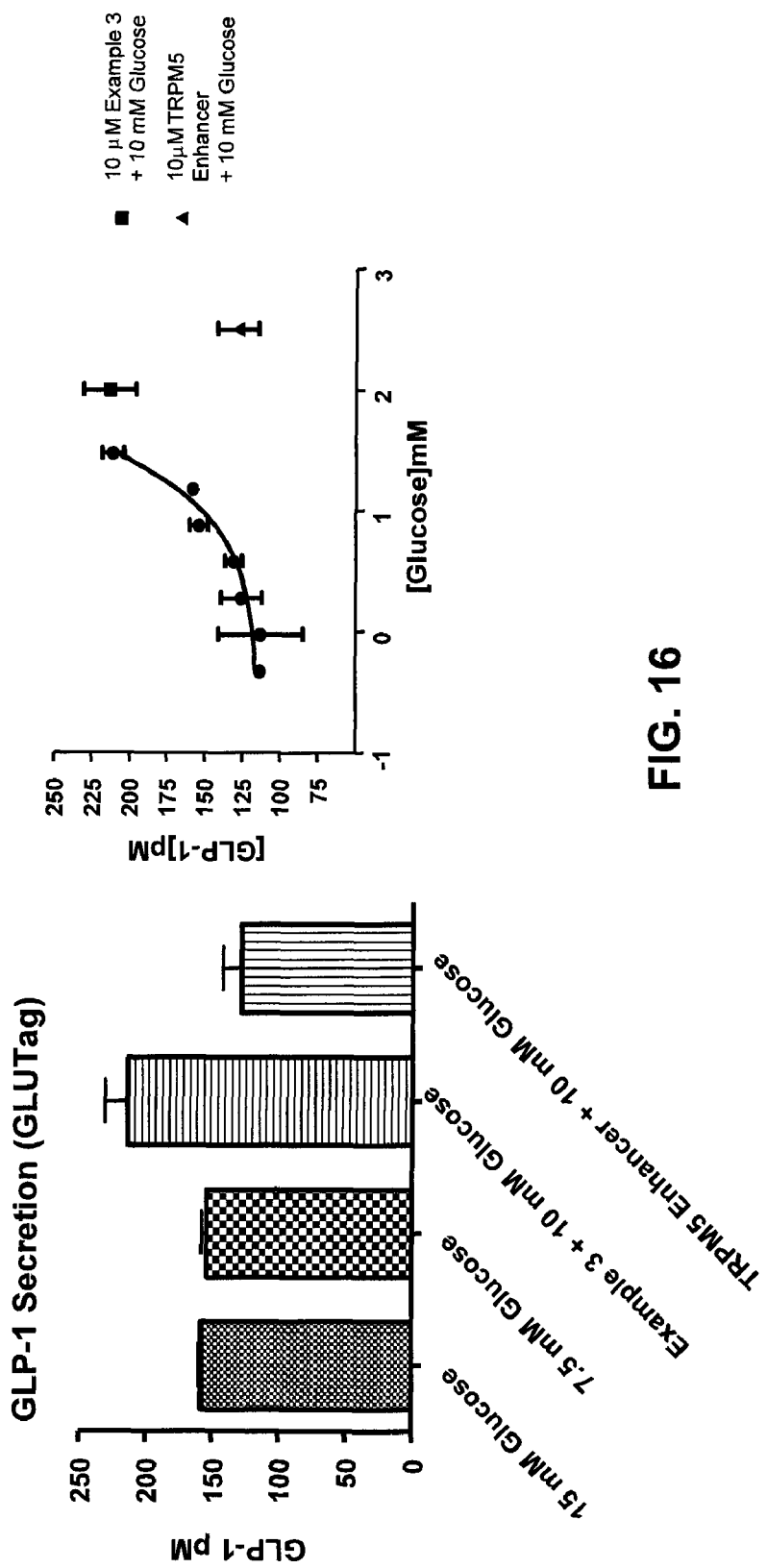

FIG. 16 shows that a TRPM5 inhibitor (the compound of Example 3) enhances GLP-1 secretion in the presence of 10 mM glucose in GLUTag cells, whereas a TRPM5 enhancer decreases GLP-1 secretion in the presence of 10 mM glucose in GLUTag cells.

Figure 17:
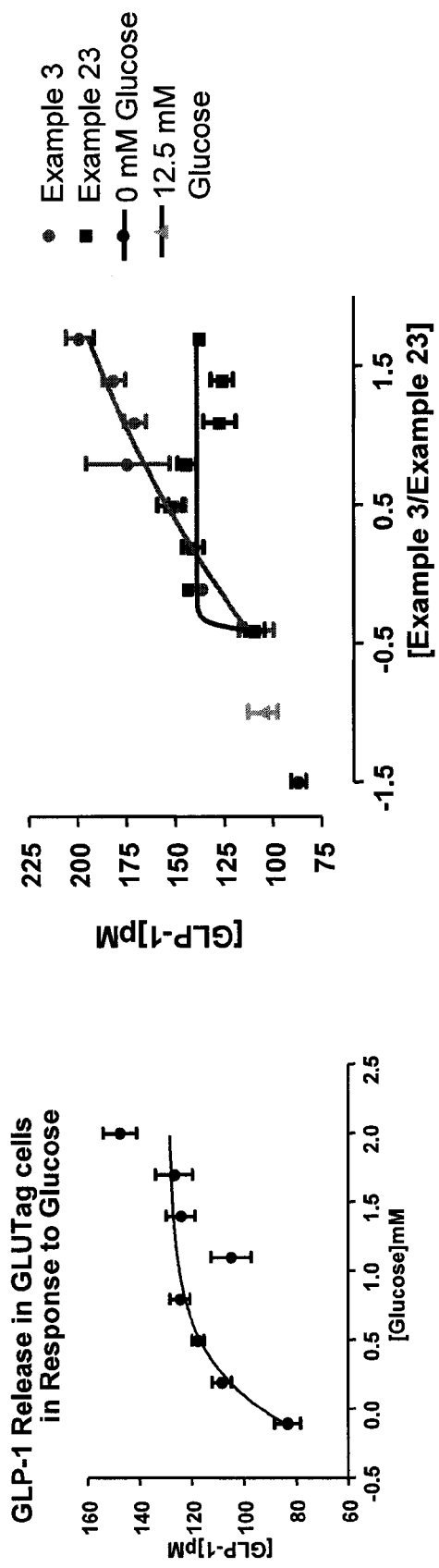

FIG. 17 shows that the compounds of Example 3 and Example 23 increase GLP-1 secretion in the presence of 12.5 mM glucose in GLUTag cells. The compound of Example 3 increases the efficacy of GLP-1 secretion, whereas the compound of Example 23 is more potent than the compound of Example 3. A standard curve of glucose for GLP-1 release is shown in comparison.

Figure 18:
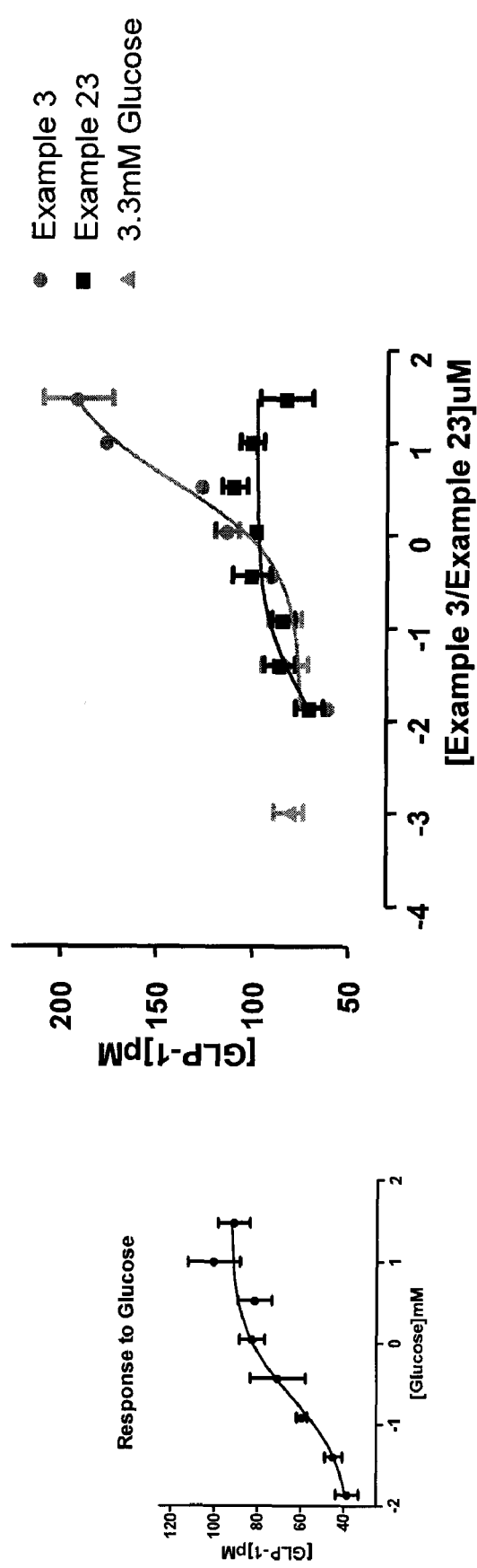

FIG. 18 shows that the compounds of Example 3 and Example 23 increase GLP-1 release in the presence of a moderately high concentration of glucose (3.3 mM) in GLUTag cells.

Figure 19:
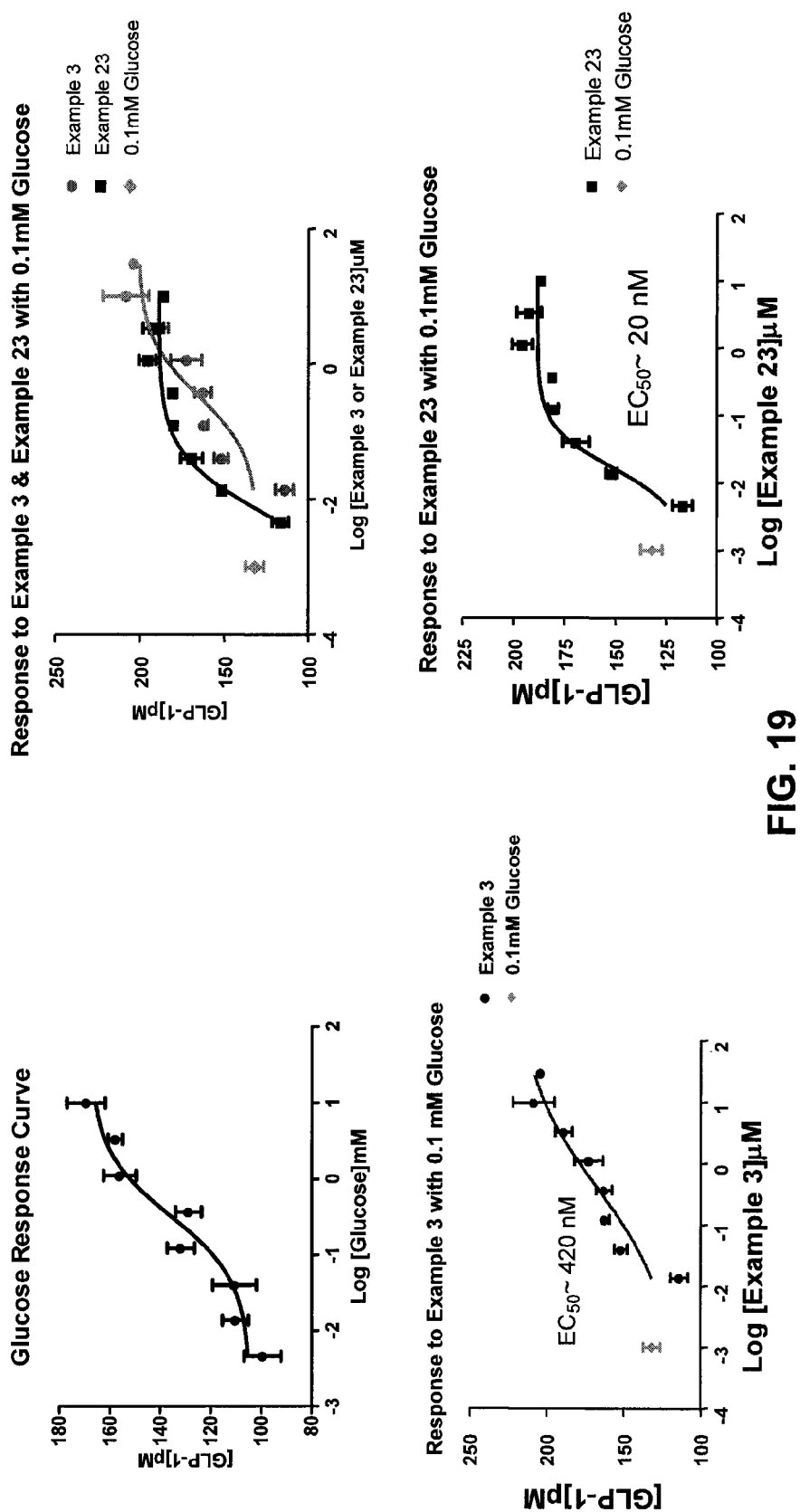

FIG. 19 shows that compounds of Example 3 and Example 23 increase GLP-1 release in the presence of low glucose (0.1 mM) in GLUTag cells. The $IC_{50}$'s of these two examples (600 nM and 111 nM, respectively) were similar to those obtained in the FLIPR Membrane Potential Assay.

DETAILED DESCRIPTION OF THE INVENTION

The present invention provides methods and compositions that are useful for increasing insulin release, GLP-1 release, insulin sensitivity, and insulin gene expression, among other uses. Other aspects of the present invention are described in detail herein.

Methods of Use

A first aspect of the present invention is directed to a method for enhancing insulin secretion, comprising administering an effective amount of a compound that is a TRPM5 inhibitor. The compound can be administered to a cell or to a whole organism in order to obtain the enhanced insulin secretion. Additionally, the TRPM5 inhibitor can be administered by itself or together with an agent known to cause the release of insulin secretion, such as glucose. By way of example, the TRPM5 used in the invention can be a TRPM5 inhibitor that has an $IC_{50}$ of 1 micromolar or less, preferably of 100 nanomolar or less. In another embodiment, the TRPM5 inhibitor used in the method inhibits the TRPM5 receptor by at least 75%, preferably 90%, at a concentration of 5 micromolar or less.

TRPM5 inhibitors can be identified using the assays and methods disclosed herein. Additionally, the assay disclosed in U.S. patent application Ser. No. 11/592,180, filed Nov. 3, 2006, hereby incorporated by reference in its entirety, can be used to identify compounds that are inhibitors of TRPM5. Also, the assay disclosed in U.S. Patent Application Publication No. 20050019830, hereby incorporated by reference in its entirety, can be used to identify compounds that are inhibitors of TRPM5.

In certain embodiments, the TRPM5 inhibitor may be a protein, a peptide, a small molecule, or a natural product. In a preferred instance, a small molecule TRPM5 inhibitor is used to inhibit a taste in the method of the invention. For example, a TRPM5 inhibitor may be a small molecule compound with a molecular weight of less than or equal to approximately 500 mass units. In another embodiment, a TRPM5 inhibitor may be a small molecule with a molecular weight of about 50 to about 500 mass units. Alternatively, a TRPM5 inhibitor may be a small molecule having a molecular weight of about 100, 200, 300, or 400 mass units. Such compounds can be selected from any of the specific compounds or groups described herein.

A TRPM5 inhibitor useful in the present invention may include any number of chemical functional groups. In certain embodiments of the method, a preferred TRPM5 inhibitor will include one or more functional groups selected from a preferred group. By way of example, in a preferred instance, a TRPM5 inhibitor used in the method will contain about 5 or fewer hydrogen bond donors (e.g., OH and NH groups). In another embodiment, a TRPM5 inhibitor used in the method will contain about 10 or fewer hydrogen bond acceptors (e.g., N and O). Such compounds can be selected from any of the specific compounds or groups described herein. In a preferred embodiment, the TRPM5 inhibitor used in the present methods will contain 1 to 5 hydrogen bond donors and 1 to 5 hydrogen bond acceptors.

A TRPM5 inhibitor may include, by way of nonlimiting examples, one or more of the following functional groups in its structure: pyridinyl, homopyridinyl, aminopiperidinylcarbamate, phenylcarbamate, cyclohexyl, cyclopentyl, piperidinyl, piperazinyl, pyrrolyl, furanyl thienyl, pyrazolyl, imidazolyl, thiazolyl, isothiazolyl, oxazolyl, isoxazolyl, oxadiazolyl, triazolyl, tetrazolyl, pyridyl, pyrimdyl, benzimidazolyl, naphthyl, indolyl, isoindolyl, benzofuranyl, isobenzofuranyl, benzo[b]thiophenyl, benz[d]isoxazoly, quinolinyl, isoquinolinyl, cinnolinyl, quinazolinyl, and quinoxalinyl groups. In another embodiment, a TRPM5 inhibitor may include, but is not limited to, the following functional groups in its chemical structure: pyridinyl, homopyridinyl, aminopiperidinylcarbamate, phenylcarbamate, cyclohexyl, cyclopentyl, piperidinyl, piperazinyl, pyrrolyl, furanyl thienyl, pyrazolyl, imidazolyl, thiazolyl, isothiazolyl, oxazolyl, isoxazolyl, oxadiazolyl, triazolyl, tetrazolyl, pyridyl, pyrimdyl, benzimidazolyl, naphthyl, indolyl, isoindolyl, benzofuranyl, isobenzofuranyl, benzo[b]thiophenyl, benz[d]isoxazoly, quinolinyl, isoquinolinyl, cinnolinyl, quinazolinyl, and quinoxalinyl groups optionally substituted with benzene, halide, amine, hydroxyl and/or alkyl groups. Such compounds can be selected from any of the specific compounds or groups described herein.

In other embodiments, the TRPM5 inhibitor used in the present method will contain a partition coefficient (log P) of about 0 to about 5, preferably from about 1 to about 5, or from about 2 to about 4. Such compounds can be selected from any of the specific compounds or groups described herein.

In yet another embodiment, a suitable TRPM5 inhibitor is a TRPM5 inhibitor with a molecular weight of 100 to 500 mass units and which contains one or more, preferably one to three, of the following functional groups in its chemical structure: pyridinyl, homopyridinyl, aminopiperidinylcarbamate, phenylcarbamate, cyclohexyl, cyclopentyl, piperidinyl, piperazinyl, pyrrolyl, furanyl thienyl, pyrazolyl, imidazolyl, thiazolyl, isothiazolyl, oxazolyl, isoxazolyl, oxadiazolyl, triazolyl, tetrazolyl, pyridyl, pyrimdyl, benzimidazolyl, naphthyl, indolyl, isoindolyl, benzofuranyl, isobenzofuranyl, benzo[b]thiophenyl, benz[d]isoxazoly, quinolinyl, isoquinolinyl, cinnolinyl, quinazolinyl, and quinoxalinyl groups optionally substituted with benzene, halide, amine, hydroxyl and/or alkyl groups. Such compounds can be selected from any of the specific compounds or groups described herein.

In one embodiment, the method comprises administering to a subject in need of increased insulin release a compound of Formula I:

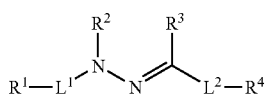

I or a physiologically acceptable salt thereof, wherein
$R^1$ is $C_{6-14}$ aryl, 5-14 membered heteroaryl, $C_{3-14}$ cycloalkyl, $C_{3-14}$ cycloalkenyl, 3-14 membered cycloheteroalkyl, 3-14 membered cycloheteroalkenyl, and $C_{1-6}$ alkyl, each of which is optionally substituted;
$R^2$ is H, $C_{1-6}$ alkyl, $C_{6-10}$ aryl, or $C_{6-10}$ aryl($C_{1-6}$)alkyl;
$R^3$ is H, $C_{1-6}$ alkyl, $C_{6-10}$ aryl, or cyano;
$R^4$ is $C_{1-6}$ alkyl, $C_{6-14}$ aryl, 5-14 membered heteroaryl, $C_{3-14}$ cycloalkyl, $C_{3-14}$ cycloalkenyl, 3-14 membered cycloheteroalkyl, or 3-14 membered cycloheteroalkenyl, each of which is optionally substituted, or is cyano;
$L^1$ is absent, or is a linker containing 1-10 carbon and/or heteroatoms and which is optionally substituted;
$L^2$ is absent, or is a linker containing 1-10 carbon and/or heteroatoms and which is optionally substituted; or
$R^3$, $R^4$, and $L^2$, together with the carbon atom to which $L^2$ and $R^3$ are attached, form a group selected from $C_{6-14}$ aryl, 5-14 membered heteroaryl, $C_{3-14}$ cycloalkyl, $C_{3-14}$ cycloalkenyl, 3-14 membered cycloheteroalkyl, 3-14 membered cycloheteroalkenyl, each of which is optionally substituted.

In one embodiment, $R^1$ is optionally substituted $C_{6-10}$ aryl, such as phenyl or naphthyl. In another embodiment, $R^1$ is optionally substituted 5-10 membered, or preferably 5-7 membered, heteroaryl, such as but not limited to pyridyl, pyrimidinyl, imidazolyl, tetrazolyl, furanyl, thienyl, indolyl, azaindolyl, quinolinyl, pyrrolyl, benzimidazolyl, and benzothiazolyl, each of which is optionally substituted. In other instances, the heteroaryl group is a nitrogen containing heteroaryl or an oxygen containing heteroaryl.

In another embodiment, $R^1$ is an optionally substituted 10-14 membered heteroaryl group, such as a carbazolyl group, for example 9-carbazolyl, or a quinolinyl group, e.g., a 2-quinolinyl group.

Another subset of $R^1$ includes a substituted aryl or heteroaryl group having 1-3 substituents independently selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy($C_{2-6}$)alkoxy, $C_{2-6}$ carboxyalkoxy, and $C_{2-6}$ carboxyalkyl. A suitable $R^1$ group includes a 4,8-dimethylquinolin-2-yl group.

In another embodiment, $R^1$ is optionally substituted $C_{3-10}$ cycloalkyl, or optionally substituted $C_{3-10}$ cycloalkenyl. In another embodiment, $R^1$ is optionally substituted 3-10 membered cycloheteroalkyl or optionally substituted 3-10 membered cycloheteroalkenyl. Suitable $R^1$ groups include, but are not limited to, cyclopropyl, cyclopentyl, cyclohexyl, cyclopentenyl, cyclohexenyl, and the like. Cycloalkyl groups also include bicycloalkyl and polycycloalkyl groups, preferably having 7-10 carbon atoms, such as bicyclo[4.1.0]heptanyl and adamantyl.

Another subset of $R^1$ includes a substituted $C_{3-10}$ cycloalkyl or $C_{3-10}$ cycloalkenyl having 1-3 substituents independently selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy($C_{2-6}$)alkoxy, $C_{2-6}$ carboxyalkoxy, and $C_{2-6}$ carboxyalkyl.

In yet a further embodiment, $R^1$ is optionally substituted $C_{1-6}$ alkyl, such as methyl, ethyl and propyl. $R^1$ may be a straight-chain or branched alkyl group. Suitable substituted alkyls include haloalkyl, hydroxyalkyl, aminoalkyl, and the like.

In another embodiment, $R^2$ is H. Alternatively, $R^2$ is $C_{1-6}$ alkyl, such as methyl, ethyl, or propyl. $R^2$ may be a straight-chain or branched alkyl group. In other embodiments, $R^2$ is a $C_{6-10}$ aryl($C_{1-6}$)alkyl, such as benzyl, phenethyl, or phenylpropyl groups. Preferably, $R^2$ is a $C_{6-10}$ aryl($C_{1-4}$)alkyl.

In a further embodiment, $R^3$ is H. Alternatively, $R^3$ is $C_{1-6}$ alkyl, such as methyl, ethyl, or propyl. $R^3$ may be a straight-chain or branched alkyl group. In yet another embodiment, $R^3$ is cyano (—CN).

In another embodiment, $R^4$ is optionally substituted $C_{6-10}$ aryl, such as phenyl or naphthyl. In another embodiment, $R^4$ is optionally substituted 5-10 membered, or preferably 5-7 membered, heteroaryl, such as but not limited to pyridyl, pyrimidinyl, imidazolyl, tetrazolyl, furanyl, thienyl, indolyl, azaindolyl, quinolinyl, pyrrolyl, benzimidazolyl, and benzothiazolyl, each of which is optionally substituted. In other instances, the heteroaryl group is a nitrogen containing heteroaryl. In other instances, the heteroaryl group is an oxygen containing heteroaryl.

Another subset of $R^4$ includes a substituted aryl or heteroaryl group having 1-3 substituents independently selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, $C_{2-6}$ carboxyalkoxy, and $C_{2-6}$ carboxyalkyl. A suitable $R^4$ group includes a 3,4-dimethoxyphenyl group.

In another embodiment, $R^4$ is optionally substituted $C_{3-10}$ cycloalkyl, or optionally substituted $C_{3-10}$ cycloalkenyl. In another embodiment, $R^4$ is optionally substituted 3-10 membered cycloheteroalkyl or optionally substituted 3-10 membered cycloheteroalkenyl. Suitable $R^4$ groups include, but are not limited to, cyclopropyl, cyclopentyl, cyclohexyl, cyclopentenyl, cyclohexenyl, and the like. Cycloalkyl groups also include bicycloalkyl groups, such as bicyclo[4.1.0]heptanyl.

In yet a further embodiment, $R^4$ is optionally substituted $C_{1-6}$ alkyl, such as methyl, ethyl, and propyl. $R^4$ may be a straight-chain or branched alkyl group. Suitable substituted alkyls include haloalkyl, hydroxyalkyl, aminoalkyl, and the like.

In one embodiment, $L^1$ is absent. Thus, according to this embodiment, $R^1$ is bonded directly to the nitrogen atom by a single bond.

In another embodiment, $L^1$ is a linker containing 1-10, preferably 1-7, carbon and/or heteroatoms and which is optionally substituted. The linker is a divalent moiety that connects $R^1$ to the nitrogen. The linker can be any suitable divalent moiety that contains 1-10 carbon and/or heteroatoms. Suitable linkers will contain, for example, 1, 2, 3, 4, 5, or 6 carbon and/or heteroatoms.

For example, the linker can be a divalent carbon linker with 1-10, preferably 1-7, carbon atoms, such as but not limited to, methylene (—$CH_2$—), ethylene (—$CH_2$—$CH_2$—), propylene (e.g., —$CH_2$—$CH_2$—$CH_2$—), butylene, and the like. Alternatively, $L^1$ can be a $C_{3-10}$ cycloalkylene linker, such as methylenecyclopropylene. A divalent carbon linker can be substituted with suitable substituents as described herein. In another subset, a preferred group of substituents includes amino, hydroxy, halogen, cyano, thiol, oxo, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, aminocarbonyl, and $C_{2-6}$ carboxyalkyl.

$L^1$ can also be a divalent linker that contains 2-10, preferably 2-6, carbon and heteroatoms. Such linkers include, by way of nonlimiting examples, alkyleneoxy, alkyleneamino, alkylenethio, alkylenedioxy. Other suitable examples include —$OCH_2$—, —$SCH_2$—, —$NHCH_2$—, —$OCH_2CH_2$—, —$NHCH_2CH_2$—, and —$OCH_2CH_2CH_2$—. It is understood that a preferred linker containing both carbon and heteroatoms will be one in which a heteroatom is not directly attached to the nitrogen atom of Formula I.

The linker $L^1$ can also be contain 1-10 heteroatoms, preferably 1, 2, or 3 heteroatoms. Suitable heteroatom linkers include —O—, —S—, —NH—, —N═N—, and the like.

In other embodiments, the linker $L^1$ is a 1-6 membered alkylene, alkenylene, or alkynylene moiety. In other embodiments, the linker $L^1$ is a 1-6 membered heteroalkylene, heteroalkenylene, or heteroalkynylene moiety.

The linker $L^1$ can be substituted as described herein. In one embodiment, linker $L^1$ is a divalent moiety containing 1-6 carbon atoms and substituted with 1, 2, or 3 substituents selected from the group consisting of amino, hydroxy, nitro, halogen, cyano, thiol, oxo, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$) alkoxy($C_{2-6}$)alkoxy, $C_{2-6}$ carboxyalkoxy, and $C_{2-6}$ carboxyalkyl.

In another embodiment, $L^1$ is a linker selected from the group consisting of

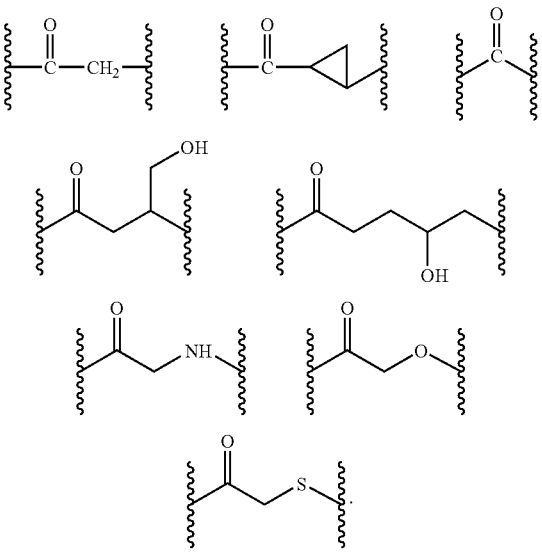

In another embodiment, $L^1$ is a linker selected from the group consisting of —(O)C$CH_2$S—.

In a further embodiment, $R^1$ and $L^1$ together form a group selected from

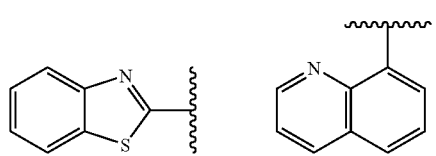

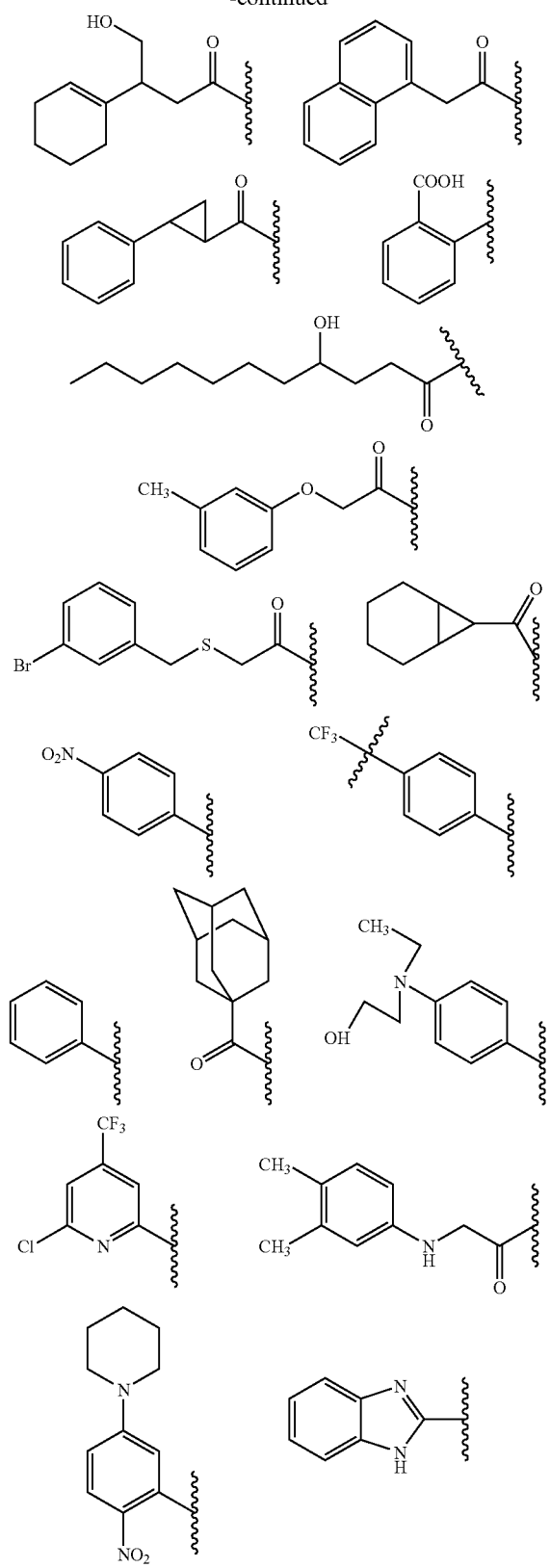

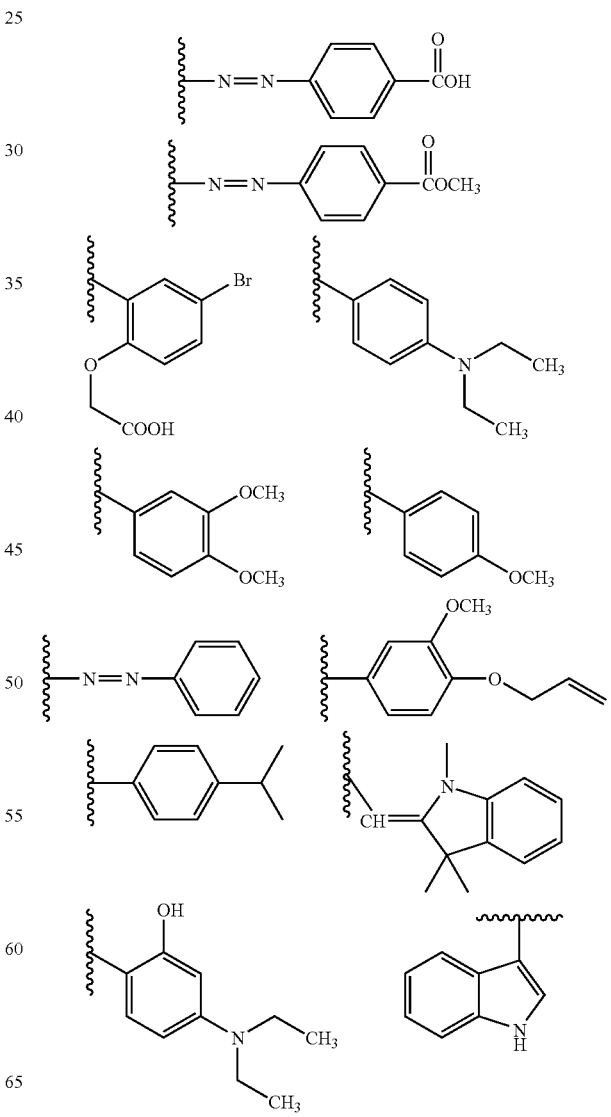

$L^2$ can also be a divalent linker that contains 2-10, preferably 2-6, carbon and heteroatoms. Such linkers include, by way of nonlimiting examples, alkyleneoxy, alkyleneamino, alkylenethio, alkylenedioxy. Other suitable examples include —OCH$_2$—, —NHCH$_2$—, —OCH$_2$CH$_2$—, —NHCH$_2$CH$_2$—, and —OCH$_2$CH$_2$CH$_2$—. It is understood that a preferred linker containing both carbon and heteroatoms will be one in which a heteroatom is not directly attached to the nitrogen atom of Formula I. In some instances, $L^2$ does not contain a ring system.

The linker $L^2$ can also be a linker having 1-10 heteroatoms, preferably 1, 2, or 3 heteroatoms. Suitable heteroatom linkers include —O—, —S—, —NH—, —N=N—, and the like.

In a further embodiment, $R^4$ and $L^2$ together form a group selected from —N=N-aryl and —N=N-heteroaryl. Suitable examples of —N=N-aryl include, but are not limited to, —N=N-phenyl, in which the phenyl is optionally substituted, and —N=N-naphthyl, in which the naphthyl is optionally substituted.

In a further embodiment, $R^4$ and $L^2$ together form a group selected from

In one embodiment, $L^2$ is absent. Thus, according to this embodiment, $R^4$ is bonded directly to the carbon atom which is bonded to the nitrogen atom by a double bond.

-continued

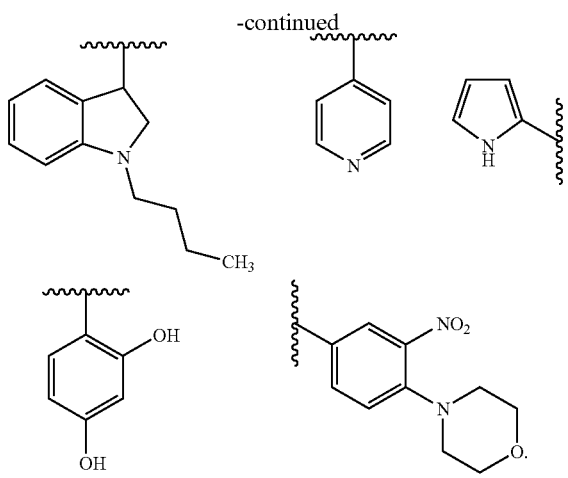

In a first subclass, the present invention is directed to a method of increasing insulin release, said method comprising administering to a subject a compound of Formula I wherein
$R^1$ is optionally substituted $C_{6-10}$ aryl;
$R^2$ is H or $C_{1-6}$ alkyl, preferably $C_{1-4}$ alkyl;
$R^3$ is H or $C_{1-6}$ alkyl, preferably $C_{1-4}$ alkyl; and
$R^4$ is optionally substituted $C_{6-10}$ aryl.

In one embodiment within this first subclass, $R^1$ is unsubstituted phenyl. In other instances, the $C_{6-10}$ aryl group, such as a phenyl group, is substituted with 1, 2, or 3 groups independently selected from the group consisting of amino, hydroxy, nitro, halogen, cyano, thiol, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkenyl, $C_{3-6}$ cycloheteroalkyl, $C_{3-6}$ cycloheteroalkenyl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy, $C_{2-10}$ mono(carboxyalkyl)amino, bis($C_{2-10}$ carboxyalkyl)amino, aminocarbonyl, $C_{2-6}$ alkynylcarbonyl, $C_{1-6}$ alkylsulfonyl, $C_{2-6}$ alkynylsulfonyl, $C_{1-6}$ alkylsulfinyl, $C_{1-6}$ alkylsulfonamido, $C_{6-10}$ arylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

In still further instances, the aryl group substituents are selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$alkylenedioxy, $C_{1-6}$ alkoxy ($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy ($C_{2-6}$)alkoxy, $C_{2-6}$ carboxyalkoxy, and $C_{2-6}$ carboxyalkyl.

In another embodiment, the substituents on $R^1$ are independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In another embodiment within this first subclass, $L^1$ is a linker containing 1-6 carbon and/or heteroatoms and which is optionally substituted.

In another embodiment within this first subclass, $L^2$ is a linker containing 1-6 carbon and/or heteroatoms and which is optionally substituted.

In another embodiment, $L^2$ does not contain a ring system.
In another embodiment within this first subclass, $R^4$ is phenyl, optionally substituted with 1 to 3 substituents selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In a second subclass, the present invention is directed to a method of increasing insulin release, said method comprising administering to a subject a compound of Formula I wherein
$R^1$ is optionally substituted 5-10 membered heteroaryl;
$R^2$ is H or $C_{1-6}$ alkyl;
$R^3$ is H or $C_{1-6}$ alkyl; and
$R^4$ is optionally substituted $C_{6-10}$ aryl.

In one embodiment within this second subclass, $R^1$ is an unsubstituted 5-10 membered heteroaryl, such as indolyl, pyridyl, benzothiazolyl, benzimidazolyl, or quinolinyl. Alternatively, $R^1$ is 5-10 membered heteroaryl substituted with one or more substituents independently selected from the group consisting of amino, hydroxy, nitro, halogen, cyano, thiol, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkenyl, $C_{3-6}$ cycloheteroalkyl, $C_{3-6}$ cycloheteroalkenyl, $C_{1-6}$ alkoxy, $C_{3-6}$ alkenyloxy, $C_{1-6}$ alkylthio, $C_{1-6}$ alkylenedioxy, $C_{1-6}$alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono ($C_{1-4}$)alkylamino($C_{2-6}$)alkoxy, di($C_{1-4}$)alkylamino($C_{2-6}$) alkoxy, $C_{2-10}$ mono(carboxyalkyl)amino, bis($C_{2-10}$ carboxyalkyl)amino, aminocarbonyl, $C_{2-6}$ alkynylcarbonyl, $C_{1-6}$ alkylsulfonyl, $C_{2-6}$ alkynylsulfonyl, $C_{1-6}$ alkylsulfinyl, $C_{1-6}$ alkylsulfonamido, $C_{6-10}$ arylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

In still further instances, the heteroaryl substituents are selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$alkylenedioxy, $C_{1-6}$ alkoxy ($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy ($C_{2-6}$)alkoxy, $C_{2-6}$ carboxyalkoxy, and $C_{2-6}$ carboxyalkyl.

In another embodiment, the substituents on $R^1$ are independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In another embodiment within this first subclass, $L^1$ is a linker containing 1-10, preferably 1-4 carbon and/or heteroatoms and which is optionally substituted.

In another embodiment within this first subclass, $L^2$ is a linker containing 1-10, preferably 1-4 carbon and/or heteroatoms and which is optionally substituted. In a further embodiment, $L^2$ does not contain a ring system.

In a third subclass, the present invention is directed to a method of increasing insulin release, said method comprising administering to a subject a compound of Formula I wherein
$R^1$ is optionally substituted $C_{6-10}$ aryl;
$R^2$ is H or $C_{1-6}$ alkyl;
$R^3$ is H or $C_{1-6}$ alkyl; and
$R^4$ is optionally substituted 5-10 membered heteroaryl;

In one embodiment within this third subclass, $R^1$ is unsubstituted phenyl. In other instances, the $C_{6-10}$ aryl group, such as a phenyl group, is substituted with 1, 2, or 3 groups independently selected from the group consisting of amino, hydroxy, nitro, halogen, cyano, thiol, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkenyl, $C_{3-6}$ cycloheteroalkyl, $C_{3-6}$ cycloheteroalkenyl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy, $C_{2-10}$ mono(carboxyalkyl)amino, bis($C_{2-10}$ carboxyalkyl)amino, aminocarbonyl, $C_{2-6}$ alkynylcarbonyl, $C_{1-6}$ alkylsulfonyl, $C_{2-6}$ alkynylsulfonyl, $C_{1-6}$ alkylsulfinyl, $C_{1-6}$ alkylsulfonamido, $C_{6-10}$ arylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

In still further instances, the aryl group substituents are selected from a group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy($C_{2-6}$)alkoxy, $C_{2-6}$ carboxyalkoxy, and $C_{2-6}$ carboxyalkyl.

In another embodiment, the substituents on $R^1$ are independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In another embodiment within this first subclass, $L^1$ is a linker containing 1-10, preferably 1-4, carbon and/or heteroatoms and which is optionally substituted.

In another embodiment within this first subclass, $L^2$ is a linker containing 1-10, preferably 1-4, carbon and/or heteroatoms and which is optionally substituted. In a further embodiment, $L^2$ does not contain a ring system.

In one embodiment within this third subclass, $R^4$ is an unsubstituted 5-10 membered heteroaryl, such as indolyl, pyridyl, benzothiazolyl, benzimidazolyl, or quinolinyl. Alternatively, $R^1$ is 5-10 membered heteroaryl substituted with one or more substituents independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In a fourth subclass, the present invention is directed to a method of increasing insulin release, said method comprising administering to a subject a compound of Formula I wherein $R^1$ is optionally substituted 5-10 membered heteroaryl;
$R^2$ is H or $C_{1-6}$ alkyl;
$R^3$ is H or $C_{1-6}$ alkyl; and
$R^4$ is optionally substituted 5-10 membered heteroaryl.

In one embodiment within this fourth subclass, $R^1$ is an unsubstituted 5-10 membered heteroaryl, such as indolyl, pyridyl, or quinolinyl. Alternatively, $R^1$ is 5-10 membered heteroaryl substituted with one or more substituents independently selected from the group consisting of amino, hydroxy, nitro, halogen, cyano, thiol, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkenyl, $C_{3-6}$ cycloheteroalkyl, $C_{3-6}$ cycloheteroalkenyl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino($C_{2-6}$)alkoxy, di($C_{1-4}$) alkylamino($C_{2-6}$)alkoxy, $C_{2-10}$ mono(carboxyalkyl)amino, bis($C_{2-10}$ carboxyalkyl)amino, aminocarbonyl, $C_{2-6}$ alkynylcarbonyl, $C_{1-6}$ alkylsulfonyl, $C_{2-6}$ alkynylsulfonyl, $C_{1-6}$ alkylsulfinyl, $C_{1-6}$ alkylsulfonamido, $C_{6-10}$ arylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

In still further instances, the heteroaryl substituents are selected from a group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy($C_{2-6}$)alkoxy, $C_{2-6}$ carboxyalkoxy, and $C_{2-6}$ carboxyalkyl.

In another embodiment, the substituents on $R^1$ are independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In one embodiment within this fourth subclass, $R^4$ is an unsubstituted 5-10 membered heteroaryl, such as indolyl, pyridyl, benzothiazolyl, benzimidazolyl or quinolinyl. Alternatively, $R^1$ is a 5-10 membered heteroaryl substituted with one or more substituents independently selected from the group consisting of amino, hydroxy, nitro, halogen, cyano, thiol, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkenyl, $C_{3-6}$ cycloheteroalkyl, $C_{3-6}$ cycloheteroalkenyl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono ($C_{1-4}$)alkylamino($C_{2-6}$)alkoxy, di($C_{1-4}$)alkylamino($C_{2-6}$) alkoxy, $C_{2-10}$ mono(carboxyalkyl)amino, bis($C_{2-10}$ carboxyalkyl)amino, aminocarbonyl, $C_{2-6}$ alkynylcarbonyl, $C_{1-6}$ alkylsulfonyl, $C_{2-6}$ alkynylsulfonyl, $C_{1-6}$ alkylsulfinyl, $C_{1-6}$ alkylsulfonamido, $C_{6-10}$ arylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

In still further instances, the heteroaryl substituents are selected from a group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy($C_{2-6}$)alkoxy, $C_{2-6}$ carboxyalkoxy, and $C_{2-6}$ carboxyalkyl.

In another embodiment, the substituents on $R^4$ are independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In a fifth subclass, the present invention is directed to a method of increasing insulin release, said method comprising administering to a subject a compound of Formula I wherein
$R^1$ is optionally substituted $C_{6-10}$ aryl;
$R^2$ is H or $C_{1-6}$ alkyl;
$R^3$ is H or $C_{1-6}$ alkyl; and
$R^4$ is optionally substituted $C_{3-10}$ cycloalkyl.

In one embodiment within this fifth subclass, $R^1$ is unsubstituted phenyl. In other instances, the $C_{6-10}$ aryl group, such as a phenyl group, is substituted with 1, 2, or 3 groups independently selected from the group consisting of amino, hydroxy, nitro, halogen, cyano, thiol, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkenyl, $C_{3-6}$ cycloheteroalkyl, $C_{3-6}$ cycloheteroalkenyl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy, $C_{2-10}$ mono(carboxyalkyl)amino, bis($C_{2-10}$ carboxyalkyl)amino, aminocarbonyl, $C_{2-6}$ alkynylcarbonyl, $C_{1-6}$ alkylsulfonyl, $C_{2-6}$ alkynylsulfonyl, $C_{1-6}$ alkylsulfinyl, $C_{1-6}$ alkylsulfonamido, $C_{6-10}$ arylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

In still further instances, the aryl substituents are selected from a group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, $C_{2-6}$ carboxyalkoxy, and $C_{2-6}$ carboxyalkyl.

In another embodiment, the substituents on $R^1$ are independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In a sixth subclass, the present invention is directed to a method of increasing insulin release, said method comprising administering to a subject a compound of Formula I wherein
$R^1$ is optionally substituted 5-10 membered heteroaryl;
$R^2$ is H or $C_{1-6}$ alkyl;
$R^3$ is H or $C_{1-6}$ alkyl; and
$R^4$ and $L^2$ together form —N═N-aryl.

In one embodiment within this sixth subclass, $R^1$ is an unsubstituted 5-10 membered heteroaryl, such as indolyl, pyridyl, or quinolinyl. Alternatively, $R^1$ is a 5-10 membered heteroaryl substituted with one or more substituents independently selected from the group consisting of amino, hydroxy, nitro, halogen, cyano, thiol, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkenyl, $C_{3-6}$ cycloheteroalkyl, $C_{3-6}$ cycloheteroalkenyl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$)alkoxy($C_{2-6}$)alkoxy, mono($C_{1-4}$)alkylamino($C_{2-6}$)alkoxy, di($C_{1-4}$)alkylamino($C_{2-6}$)alkoxy, $C_{2-10}$ mono(carboxyalkyl)amino, bis($C_{2-10}$ carboxyalkyl)amino, aminocarbonyl, $C_{2-6}$ alkynylcarbonyl, $C_{1-6}$ alkylsulfonyl, $C_{2-6}$ alkynylsulfonyl, $C_{1-6}$ alkylsulfinyl, $C_{1-6}$ alkylsulfonamido, $C_{6-10}$ arylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino. In another embodiment, the substituents on $R^1$ are independently selected from the group consisting of nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In this sixth subclass, $R^4$ and $L^2$ together form —N═N-aryl, wherein aryl is a $C_{6-10}$ optionally substituted aryl group, such as phenyl or naphthyl. Suitable substituents on the aryl group include, but are not limited to, nitro, bromo, chloro, carboxy, methoxycarbonyl, methoxy, diethylamino, hydroxymethyl, methyl, allyloxy, trifluoromethylthio, hydroxy, trifluoromethyl, morpholinyl, and pyrrolidinyl.

In a seventh subclass, the present invention is directed to a method of increasing insulin release, said method comprising administering to a subject a compound of Formula I wherein
$R^1$ is optionally substituted 5-10 membered heteroaryl, such as pyridyl, quinolinyl, benzothiazolyl, benzimidazolyl and indolyl;
$R^4$ is optionally substituted $C_{6-10}$ aryl, such as phenyl and naphthyl; and
$L^1$ and $L^2$ are absent.

In an eighth subclass, the present invention is directed to a method of increasing insulin release, said method comprising contacting administering to a subject compound of Formula I wherein
$R^1$ is $C_{6-10}$ aryl, 5-10 membered heteroaryl, $C_{3-10}$ cycloalkyl, $C_{3-10}$ cycloalkenyl, 3-10 membered cycloheteroalkyl, 3-10 membered cycloheteroalkenyl, and $C_{1-6}$ alkyl, each of which is optionally substituted;
$R^2$ is H, $C_{1-6}$ alkyl, or $C_{6-10}$ aryl($C_{1-6}$)alkyl;
$L^1$ is absent, or is a linker containing 1-10, preferably 1-6, carbon and/or heteroatoms and which is optionally substituted;
$R^3$, $R^4$, and $L^2$ together with the carbon atom form a group selected from $C_{6-10}$ aryl, 5-10 membered heteroaryl, $C_{3-10}$ cycloalkyl, $C_{3-10}$ cycloalkenyl, 3-10 membered cycloheteroalkyl, 3-10 membered cycloheteroalkenyl, each of which is optionally substituted.

In a further subclass, the invention is directed to a method of increasing insulin release, said method comprising administering to a subject a compound of Formula I wherein $R^1$ is heteroaryl; $R^2$ is H; $R^4$ is heteroaryl; $L^1$ is absent; and $L^2$ is N═N.

In an additional subclass, the invention is directed to a method of increasing insulin release wherein said method comprises administering to a subject a compound of Formula I wherein $R^1$ is an optionally substituted nitrogen-containing heteroaryl group; and $R^2$ is an optionally substituted phenyl.

In a further subclass, the invention is directed to a method of increasing insulin release said method comprising administering to a subject a compound of Formula I wherein $R^1$ is a bicycloalkyl; $R^2$ is H; $R^3$ is H; $R^4$ is aryl or heteroaryl; $L^1$ is absent; and $L^2$ is absent.

In a further subclass, the invention is directed to a method of increasing insulin release, said method comprising administering to a subject a compound of Formula I wherein $R^1$ is aryl; $R^2$ is H; $R^3$ is H; $R^4$ is aryl or heteroaryl; $L^1$ is an optionally substituted a linker containing 2-4 carbon or hetero atoms; and $L^2$ is absent.

In a further subclass, the invention is directed to a method of increasing insulin release, said method comprising administering to a subject a compound of Formula I wherein $R^1$ is cycloalkenyl; $R^2$ is H; $R^3$ is H; $R^4$ is aryl or heteroaryl; $L^1$ is an optionally substituted a linker containing 2-4 carbon or hetero atoms; and $L^2$ is absent.

In a further subclass, the invention is directed to a method of increasing insulin release, said method comprising administering to a subject a compound of Formula I wherein $R^1$ is optionally substituted aryl; $R^2$ is H; $R^3$ is H; $R^4$ is optionally substituted aryl or optionally substituted heteroaryl; $L^1$ is —(CH$_2$)$_{1-6}$—C(O)—; and $L^2$ is absent.

In a further subclass, the invention is directed to a method of increasing insulin release, said method comprising administering to a subject a compound of Formula I wherein $R^1$ is optionally substituted naphthyl; $R^2$ is H; $R^3$ is H; $R^4$ is optionally substituted aryl; $L^1$ is —(CH$_2$)—C(O)—; and $L^2$ is absent.

In a further subclass, the method of the invention comprises administering a compound of Formula I wherein $R^1$ is quinolinyl, optionally substituted with one or more $C_{1-6}$ alkyl; $L^1$ is a $C_{1-4}$ linker optionally substituted; and $R^2$ is an optionally substituted phenyl group, such as substituted with one or more $C_{1-6}$ alkoxy.

In a further subclass, the method of the invention comprises administering a compound of Formula I wherein $R^1$ is optionally substituted carbazolyl; $L^1$ is a $C_{1-6}$ linker containing one sulfur atom and further optionally substituted; and $R^2$ is an optionally substituted phenyl group, such as substituted with one or more $C_{1-6}$ alkoxy.

Examples of suitable compounds for use in the method of the present invention include:

methyl 4-((E)-((Z)-1-(2-(benzo[d]thiazol-2-yl)hydrazono)-2-methyl-propyl)diazenyl)benzoate;
(E)-2-(4-bromo-2-((2-(quinolin-8-yl)hydrazono)methyl) phenoxy)-acetic acid;
(E)-N'-(3,4-dimethoxybenzylidene)-2-(naphthalene-1-yl)-acetohydrazide;
(E)-N'-(3,4-dimethoxybenzylidene)-2-phenylcyclopropane-carbohydrazide;
(E)-3-cyclohexenyl-4-hydroxy-N'-(4-methoxybenzylidene)-butanehydrazide;
(E)-N'-(3,4-dimethoxybenzylidene)-4-hydroxyhexanehydrazide;
2-((Z)-2-(phenyl((E)-phenyldiazenyl)methylene)hydrazinyl)benzoic acid;
(E)-N'-(3,4-dimethoxybenzylidene)-2-(m-tolyloxy)acetohydrazide;
(E)-N'-(4-(allyloxy)-3-methoxybenzylidene)-2-(3-bromobenzylthio)acetohydrazide;
(E)-N'-(4-isopropylbenzylidene)bicyclo[4.1.0]heptane-7-carbo-hydrazide;
(Z)-1,3,3-trimethyl-2-((E)-2-(2-(4-nitrophenyl)hydrazono)-ethylidene)indoline;
(E)-N'-(4-(diethylamino)-2-hydroxybenzylidene)-2-phenyl-cyclopropanecarbohydrazide;
(4-(trifluoromethylthio)phenyl)carbonohydrazonoyldicyanide;
N-((E)-3-((Z)-2-(1,5-dimethyl-2-oxoindolin-3-ylidene)hydrazinyl)-3-oxo-1-phenylprop-1-en-2-yl)benzamide;
(Z)-2-(2-((1-butyl-1H-indol-3-yl)methylene)hydrazinyl) benzoic acid;
(E)-4-((2-benzyl-2-phenylhydrazono)methyl)pyridine;
(Z)-N'-((1H-pyrrol-2-yl)methylene)tricyclo[3.3.1.1$^{3,7}$]decane-3-carbohydrazide;
(Z)-1-(2-(4-(ethyl(2-hydroxyethyl)amino)phenyl)hydrazono)-naphthalen-2-(1H)-one;
(E)-4-((2-(5-chloro-3-(trifluoromethyl)pyridin-2-yl)-2-2-methyl-hydrazono)methyl)benzene-1,3-diol;
(E)-2-(3,4-dimethylphenylamino)-N'(4-morpholino-3-nitrobenzylidene)acetohydrazide;
(Z)-3-(2-nitro-5-(pyrrolidin-1-yl)phenyl)hydrazono)quinuclidine;
(E)-2-((2-(1H-benzo[c]imidazol-2-yl)hydrazono)methyl)-5-(diethylamino)phenol;
and physiologically acceptable salts thereof.

Additional suitable compounds include
3-carbazol-9-ylpropionic acid (3,4-dimethoxybenzylidene) hydrazide;
(4,8-dimethylquinolin-2-ylsulfanyl)acetic acid (3,4-dimethoxybenzylidene)hydrazide;
and physiologically acceptable salts thereof.

The methods of the present invention also include the use of a physiologically acceptable salt of a compound according to Formula I. The term physiologically acceptable salt refers to an acid- and/or base-addition salt of a compound according to Formula I. Acid-addition salts can be formed by adding an appropriate acid to the compound according to Formula I. Base-addition salts can be formed by adding an appropriate base to the compound according to Formula I. Said acid or base does not substantially degrade, decompose, or destroy said compound according to Formula I. Examples of suitable physiologically acceptable salts include hydrochloride, hydrobromide, acetate, fumarate, maleate, oxalate, and succinate salts. Other suitable salts include sodium, potassium, carbonate, and tromethamine salts.

It is also to be understood that the present invention is considered to encompass the use of stereoisomers as well as optical isomers, e.g., mixtures of enantiomers as well as individual enantiomers and diastereomers, which arise as a consequence of structural asymmetry in selected compounds of the present series. It is further understood that the present invention encompasses the use of tautomers of a compound of Formula I. Tautomers are well-known in the art and include keto-enol tautomers.

It is also understood that the compounds of Formula I include both the E and Z isomers, in varying ratios, of the hydrazone. As is known in the art, the hydrazone moiety can isomerize between the E and Z isomers, as shown in the following schematic:

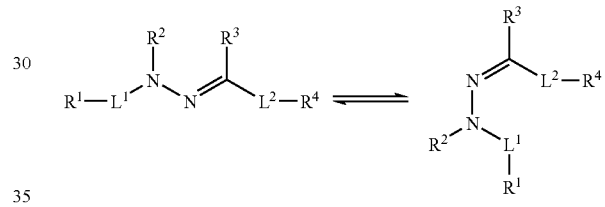

While the specific compounds listed above may indicate a particular stereochemistry of the hydrazone moiety, i.e., E or Z, the present invention explicitly includes both isomers.

The compounds of Formula I may also be solvated, including hydrated. Hydration may occur during manufacturing of the compounds or compositions comprising the compounds, or the hydration may occur over time due to the hygroscopic nature of the compounds.

Certain compounds within the scope of Formula I may be derivatives referred to as "prodrugs." The expression "prodrug" denotes a derivative of a known direct acting agent, wherein the derivative has therapeutic value that may be similar to, greater than, or less than that of the agent. Generally, the prodrug is transformed into the active agent by an enzymatic or chemical process when delivered to the subject, cell, or test media. In certain instances, prodrugs are derivatives of the compounds of the invention which have metabolically cleavable groups and become by solvolysis or under physiological conditions the compounds of the invention which are pharmaceutically active in vivo. For example, ester derivatives of compounds of this invention are often active in vivo, but not in vitro. Other derivatives of the compounds of this invention have activity in both their acid and acid derivative forms, but the acid derivative form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with an amine. Simple aliphatic or aromatic esters derived from acidic groups pendent on the compounds of this invention are preferred prodrugs. In some cases, it is desirable to prepare double ester type prodrugs such as (acyloxy) alkyl esters or ((alkoxycarbonyl)oxy)alkyl esters.

When any variable occurs more than one time in any constituent or in Formula I, its definition on each occurrence is independent of its definition at every other occurrence, unless otherwise indicated. Also, combinations of substituents and/or variables are permissible only if such combinations result in stable compounds.

The term "alkyl," as used herein by itself or as part of another group, refers to both straight and branched chain radicals of up to 10 carbons, unless the chain length is limited thereto, such as methyl, ethyl, propyl, isopropyl, butyl, 1-methylpropyl, 2-methylpropyl, pentyl, 1-methylbutyl, isobutyl, pentyl, t-amyl ($CH_3CH_2(CH_3)_2C—$), hexyl, isohexyl, heptyl, octyl, or decyl.

The term "alkenyl," as used herein by itself or as part of another group, refers to a straight or branched chain radical of 2-10 carbon atoms, unless the chain length is limited thereto, including, but not limited to, ethenyl, 1-propenyl, 2-propenyl, 2-methyl-1-propenyl, 1-butenyl, 2-butenyl, 3-butenyl, pentenyl, 1-hexenyl, and 2-hexenyl.

The term "alkynyl," as used herein by itself or as part of another group, refers to a straight or branched chain radical of 2-10 carbon atoms, unless the chain length is limited thereto, wherein there is at least one triple bond between two of the carbon atoms in the chain, including, but not limited to, ethynyl, 1-propynyl, 2-propynyl, 1-butynyl, 2-butynyl, 1-methyl-2-butynyl, 1-methyl-3-butynyl, 2-methyl-3-pentynyl, hexynyl, and heptynyl.

In instances herein where there is an alkenyl or alkynyl moiety as a substituent group, the unsaturated linkage is preferably not directly attached to a nitrogen, oxygen or sulfur moiety.

The term "cycloalkyl," as used herein by itself or as part of another group, refers to cycloalkyl groups containing 3 to 14, preferably 3 to 10, carbon atoms. Typical examples are cyclopropyl, cyclobutyl, cyclopentyl, and cyclohexyl. Cycloalkyl also includes bicycloalkyl, polycycloalkyl, and other bridged cycloalkyl groups.

The term "cycloalkenyl," as used herein by itself or as part of another group, refers to cycloalkenyl groups containing 3 to 10, carbon atoms and 1 to 3 carbon-carbon double bonds. Typical examples include cyclopropenyl, cyclobutenyl, cyclopentenyl, cyclohexenyl, cycloheptenyl, and cyclohexadienyl. Cycloalkenyl also includes bicycloalkenyl, polycycloalkenyl, and other bridged cycloalkenyl groups.

The term "cycloheteroalkyl," as employed herein by itself or as part of another group, refers to a group having 3 to 14 ring atoms containing carbon atoms and 1, 2, 3, or 4 oxygen, nitrogen, or sulfur heteroatoms. Typical examples include, but are not limited to, 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl, pyrrolidinyl, imidazolidinyl, pirazolidinyl, tetrahydrofuranyl, tetrahydropyranyl, piperidyl, piperazinyl, quinuclidinyl, and morpholinyl.

The term "cycloheteroalkenyl," as used by itself or as part of another group, refers to a group containing 3 to 14 ring atoms containing carbon atoms and 1, 2, 3, or 4 oxygen, nitrogen, or sulfur atoms and 1, 2, or 3 double bonds. Typical examples include preferably the cycloheteroalkyl groups recited above, specifically pyrrolidinyl, imidazolidinyl, pirazolidinyl, tetrahydrofuranyl, tetrahydropyranyl, piperidyl, piperazinyl, quinuclidinyl, and morpholinyl, and modified so as to contain 1 or 2 double bonds.

The term "alkylene," as used herein by itself or as a part of another group, refers to a diradical of an unbranched saturated hydrocarbon chain, having, unless otherwise indicated, from 1 to 15 carbon atoms, preferably 1 to 10 carbon atoms and more preferably 1 to 6 carbon atoms. This term is exemplified by groups such as methylene ($—CH_2—$), ethylene ($—CH_2CH_2—$), propylene ($—CH_2CH_2CH_2—$), butylene, and the like.

The term "alkenylene," as used herein by itself or part of another group, refers to a diradical of an unbranched, unsaturated hydrocarbon chain, having, unless otherwise indicated, from 2 to 15 carbon atoms, preferably 1 to 10 carbon atoms, more preferably 1 to 6 carbon atoms, and having at least 1 and preferably from 1 to 6 sites of vinyl unsaturation. This term is exemplified by groups such as ethenylene ($—CH=CH—$), propenylene ($—CH_2CH=CH—$, $—CH=CHCH_2—$), and the like.

The term "alkynylene," as used herein by itself or part of another group, refers to a diradical of an unbranched, unsaturated hydrocarbon having, unless otherwise indicated, from 2 to 15 carbon atoms preferably 1 to 10 carbon atoms, more preferably 1 to 6 carbon atoms, and having at least 1 and preferably from 1 to 6 sites of acetylene (triple bond) unsaturation. Examples include alkynylene groups such as ethynylene ($—C≡C—$), propargylene ($—CH_2—C≡C—$), and the like.

The term "heteroalkylene," as used herein by itself or party of another group means alkylene, as defined above, wherein 1 to 5 of the carbon atoms indicated is replaced by a heteroatom chosen from N, O, or S (e.g., amino, oxy, thio, aminomethylene ($—NHCH_2—$), oxymethylene ($—OCH_2—$), etc.). Examples include alkyleneoxy, alkyleneamino, and alkylenethio. Preferably, the oxygen, nitrogen, and sulfur atoms contained therein do not form bonds with other heteroatoms. Suitable groups include ethyleneoxy, propyleneoxy, butyleneoxy, pentyleneoxy, heptyleneoxy, ethyleneamino, propyleneamino, butyleneamino, pentyleneamino, hexyleneamino, heptyleneamino, and octyleneamino. Further examples include $—CH_2CH_2—S—CH_2CH_2—$ and $—CH_2—S—CH_2CH_2—NH—CH_2—$. In one embodiment of heteroalkylene groups, heteroatoms can also occupy either but not both of the chain termini.

The term "heteroalkenylene," as used herein by itself or part of another group, means alkenylene, as defined above, wherein 1 to 5 of the carbon atoms indicated is replaced by a heteroatom chosen from N, O, or S. Examples include alkenyleneoxy, alkenyleneamino, and alkenylenethio. Preferably, the oxygen, nitrogen, and sulfur atoms contained therein do not form bonds with other heteroatoms. Suitable groups include ethenyleneoxy, propenyleneoxy, butyenleneoxy, pentenyleneoxy, hexenyleneoxy, ethenyleneamino, propenyleneamino, butyenleneamino, pentenyleneamino, and hexenyleneamino. In one embodiment of heteroalkenylene groups, heteroatoms can also occupy either, but not both, of the chain termini. Additionally, in another embodiment, the heteroatom does not form part of the vinyl bond.

The term "heteroalkynylene," as used herein by itself or as part of another group, means alkynylene, as defined above, wherein 1 to 5 of the carbon atoms indicated is replaced by a heteroatom chosen from N, O, or S. Examples include alkynyleneoxy, alkynyleneamino, and alkynylenethio. Preferably, the oxygen, nitrogen, and sulfur atoms contained therein do not form bonds with other heteroatoms. In one embodiment of heteroalkynylene groups, heteroatoms can occupy either, but not both, of the chain termini. Additionally, the heteroatom does not form part of the vinyl bond.

The term "cycloalkylene," as used herein by itself or as part of another group, refers to a non-aromatic alicyclic divalent hydrocarbon radical having from 3 to 15 carbon atoms, preferably 3 to 10 carbon atoms. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, and the like. Further examples include divalent groups which also contain an alkylene group such as methylenecyclopropylene (i.e., —$CH_2$-cyclopropylene-), ethylenecyclopropylene (i.e., —$CH_2CH_2$-cyclopropylene-), and methylenecyclohexylene (i.e., —$CH_2$-cyclohexylene-).

The term "cycloalkenylene," as used herein by itself or as part of another group, refers to a substituted alicyclic divalent hydrocarbon radical having from 3 to 15 carbon atoms, preferably 3 to 10, and at least one carbon-carbon double bond. Examples of "cycloalkenylene" as used herein include, but are not limited to, 4,5-cyclopentene-1,3-diyl, 3,4-cyclohexene-1,1-diyl, and the like. Cycloalkenylene additionally refers to a divalent hydrocarbon radical as defined for cycloalkylene and having at least one single bond replaced with a double bond. The double bond may be contained in the ring structure. Alternatively, when possible, the double bond may be located on an acyclic portion of the cycloalkeneylene moiety.

The term "cycloheteroalkylene," as used herein by itself or as part of another group, refers to a cycloalkylene group as described above, wherein 1 to 5 of the carbon atoms indicated is replaced by a heteroatom chosen from N, O, or S. In one embodiment, the oxygen, nitrogen, and sulfur atoms contained therein do not form bonds with other heteroatoms. Suitable examples include the diradicals of piperidine, piperazine, morpholine, and pyrrolidine. Other suitable examples include methylenepiperidyl, ethylenepiperidyl, methylenepiperazinyl, ethylenepiperazinyl, and methylenemorpholinyl.

The term "cycloheteroalkenylene," as used herein by itself or as part of another group, refers to a cycloalkenylene group as described above, wherein 1 to 5 of the carbon atoms indicated is replaced by a heteroatom chosen from N, O, or S. In one embodiment, the oxygen, nitrogen, and sulfur atoms contained therein do not form bonds with other heteroatoms.

The term "alkoxy," as used herein by itself or as part of another group, refers to any of the above alkyl groups linked to an oxygen atom. Typical examples are methoxy, ethoxy, isopropyloxy, sec-butyloxy, and t-butyloxy.

The term "alkenyloxy," as used herein by itself or as part of another group, refers to any of the above alkenyl groups linked to an oxygen atom. Typical examples include ethenyloxy, propenyloxy, butenyloxy, pentenyloxy, and hexenyloxy.

The term "aryl," as used herein by itself or as part of another group, refers to monocyclic or bicyclic aromatic groups containing from 6 to 14 carbons in the ring portion, preferably 6-10 carbons in the ring portion. Typical examples include phenyl, naphthyl, anthracenyl, or fluorenyl.

The term "aralkyl" or "arylalkyl," as employed herein by itself or as part of another group, refers to $C_{1-6}$ alkyl groups as defined above having an aryl substituent, such as benzyl, phenylethyl, or 2-naphthylmethyl.

The term "heteroaryl," as used herein by itself or as part of another group, refers to groups having 5 to 14 ring atoms; 6, 10, or 14 π electrons shared in a cyclic array; and containing carbon atoms and 1, 2, 3, or 4 oxygen, nitrogen, or sulfur atoms. Examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups. Further heteroaryls are described in A. R. Katritzky and C. W. Rees, eds., Comprehensive Heterocyclic Chemistry The Structure, Reactions, Synthesis and Use of Heterocyclic Compounds, Vol. 1-8, Pergamon Press, NY (1984).

The term "alkylenedioxy," as used herein by itself or as part of another group, refers for a ring and is especially $C_{1-4}$ alkylenedioxy. Alkylenedioxy groups may optionally be substituted with halogen (especially fluorine). Typical examples include methylenedioxy (—$OCH_2O$—) or difluoromethylenedioxy (—$OCF_2O$—).

The term "halogen" or "halo," as used herein by itself or as part of another group, refers to chlorine, bromine, fluorine or iodine.

The term "monoalkylamine" or "monoalkylamino," as used herein by itself or as part of another group, refers to the group $NH_2$ wherein one hydrogen has been replaced by an alkyl group, as defined above.

The term "dialkylamine" or "dialkylamino," as used herein by itself or as part of another group refers to the group, $NH_2$ wherein both hydrogens have been replaced by alkyl groups, as defined above.

The term "hydroxyalkyl," as used herein by itself or as part of another group, refers to any of the above alkyl groups wherein one or more hydrogens thereof are substituted by one or more hydroxyl moieties.

The term "acylamino," as used herein refers to a moiety of the formula —$NR^aC(O)R^b$, wherein $R^a$ and $R^b$ are independently hydrogen or alkyl groups is defined above.

The term "haloalkyl," as used herein by itself or as part of another group, refers to any of the above alkyl groups wherein one or more hydrogens thereof are substituted by one or more halo moieties. Typical examples include fluoromethyl, trifluoromethyl, trichloroethyl, and trifluoroethyl.

The term "haloalkenyl," as used herein by itself or as part of another group, refers to any of the above alkenyl groups wherein one or more hydrogens thereof are substituted by one or more halo moieties. Typical examples include fluoroethenyl, difluoroethenyl, and trichloroethenyl.

The term "carboxyalkyl," as used herein by itself or as part of another group, refers to any of the above alkyl groups wherein one or more hydrogens thereof are substituted by one or more carboxylic acid moieties.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or alkyl, or together with the nitrogen to which they are bound, form a saturated or unsaturated 5-, 6-, or 7-membered ring.

The term "oxy" means an oxygen (O) atom.

The term "thio" means a sulfur (S) atom.

Generally and unless defined otherwise, the phrase "optionally substituted" used herein refers to a group or groups being optionally substituted with one or more substituents independently selected from the group consisting of amino, hydroxy, nitro, halogen, cyano, thiol, $C_{1-6}$ alkyl, $C_{2-6}$ alkenyl, $C_{2-6}$ alkynyl, $C_{3-6}$ cycloalkyl, $C_{3-6}$ cycloalkenyl, $C_{3-6}$ cycloheteroalkyl, $C_{3-6}$ cycloheteroalkenyl, $C_{6-10}$ aryl, 5-10 membered heteroaryl, $C_{1-6}$ alkoxy, $C_{3-6}$ alkenyloxy, $C_{1-6}$ alkylthio, $C_{1-6}$ alkylenedioxy, $C_{1-6}$ alkoxy($C_{1-6}$)alkyl, $C_{6-10}$ aryl($C_{1-6}$)alkyl, $C_{6-10}$ aryl($C_{2-6}$)alkenyl, $C_{6-10}$ aryl($C_{1-6}$) alkoxy, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$) alkylamino, $C_{2-6}$ alkylcarbonylamino, $C_{2-6}$ alkoxycarbonylamino, $C_{2-6}$ alkoxycarbonyl, carboxy, ($C_{1-6}$) alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl) amino, bis($C_{2-10}$ carboxyalkyl)amino, aminocarbonyl, $C_{6-14}$ aryl($C_{1-6}$)alkoxycarbonyl, $C_{2-6}$ alkynylcarbonyl, $C_{1-6}$ alkylsulfonyl, $C_{2-6}$ alkynylsulfonyl, $C_{6-10}$ arylsulfonyl, $C_{6-10}$ aryl ($C_{1-6}$)alkylsulfonyl, $C_{1-6}$ alkylsulfinyl, $C_{1-6}$ alkylsulfonamido, $C_{6-10}$ arylsulfonamido, $C_{6-10}$ aryl($C_{1-6}$) alkylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

When the phrase "optionally substituted" is used with reference to an alkyl, alkenyl, or alkynyl group, the phrase "optionally substituted" herein refers to said group or groups being optionally substituted with one or more substituents independently selected from the group consisting of amino, hydroxy, nitro, halogen, cyano, thiol, $C_{3-6}$ cycloalkyl, $C_{3-6}$ cycloalkenyl, $C_{3-6}$ cycloheteralkyl, $C_{3-6}$ cycloheteroalkenyl, $C_{6-10}$ aryl, 5-10 membered heteroaryl, $C_{1-6}$ alkoxy, $C_{3-6}$ alkenyloxy, $C_{1-6}$ alkylthio, $C_{1-6}$ alkylenedioxy, $C_{1-6}$ alkoxy ($C_{1-6}$)alkyl, $C_{6-10}$ aryl($C_{1-6}$)alkyl, $C_{6-10}$ aryl($C_{2-6}$)alkenyl, $C_{6-10}$ aryl($C_{1-6}$)alkoxy, $C_{1-6}$ aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$ alkoxycarbonyl, carboxy, ($C_{1-6}$) alkoxy($C_{2-6}$)alkoxy, mono($C_{1-4}$)alkylamino($C_{2-6}$)alkoxy, di($C_{1-4}$)alkylamino($C_{2-6}$)alkoxy $C_{2-10}$ mono(carboxyalkyl) amino, bis($C_{2-10}$ carboxyalkyl)amino, $C_{6-14}$ aryl($C_{1-6}$) alkoxycarbonyl, $C_{2-6}$ alkynylcarbonyl, $C_{1-6}$ alkylsulfonyl, $C_{2-6}$ alkynylsulfonyl, $C_{6-10}$ arylsulfonyl, $C_{6-10}$ aryl($C_{1-6}$) alkylsulfonyl, $C_{1-6}$ alkylsulfinyl, $C_{1-6}$ alkylsulfonamido, $C_{6-10}$ arylsulfonamido, $C_{6-10}$ aryl($C_{1-6}$) alkylsulfonamido, $C_{1-6}$ alkyliminoamino, formyliminoamino, $C_{2-6}$ carboxyalkoxy, $C_{2-6}$ carboxyalkyl, and carboxy($C_{1-6}$)alkylamino.

Although detailed definitions have not been provided for every term used above, each term is understood by one of ordinary skill in the art.

As defined above in certain embodiments, the linkers $L^1$ and $L^2$ may be a linker containing 1-10 carbon and/or heteroatoms and which is optionally substituted. This is understood to mean that the linkers may contain any combination of carbon atoms and heteroatoms, such that the sum of number of carbon and heteroatoms, excluding any optional substituents, equals an integer from 1 to 10. Thus, in accordance with the invention, suitable linkers may include, but not necessarily limited to: a linker containing 1 carbon atom (e.g., $CH_2$); a linker containing one heteroatom (e.g., O); a linker containing five carbon atoms (e.g., $CH_2CH_2CH_2CH_2CH_2$); a linker containing 3 carbon atoms and 2 heteroatoms (e.g., $OCH_2CH_2NHCH_2$); a linker containing 10 carbon atoms; or a linker containing nine carbon atoms and 1 heteroatom.

The term "inhibitor" refers to a molecule that alters partially or impairs the functions and/or properties of TRPM5. "Inhibitors" include peptides, proteins or fragments thereof, peptidomimetics, organic compounds and antibodies. In certain embodiments of the present invention, the inhibitor may completely block the function of TRPM5. In other embodiments, the inhibitor may block, or inhibit, a percentage of activity of TRPM5, as indicated in, e.g., $IC_{50}$ values.

The term "diabetes" refers to one metabolic disorder in which there is impaired glucose utilization inducing hyperglycemia. An overview of the pathogenesis and morphology of diabetes and its late complications is available to practitioners of the art, for instance, in Robins' Pathologic Basis of Disease ($5^{th}$ Ed. pp. 910-922).

The term "effective amount" of a TRPM5 inhibitor refers to an amount that inhibits or imparts an inhibitory effect on a TRPM5 receptor. Such an amount is sufficient by itself or in combination with other TRPM5 inhibitors to impart a TRPM5 inhibitory effect to a cell or to a whole organism to which it is administered. In some embodiments, an effective amount is one that does not cause excessive toxicity, irritation, allergic response, or other possible complications commensurate with a reasonable benefit/risk ratio.

The term "insulin resistance syndrome" (IRS) refers to the cluster of manifestations which include insulin resistance; hyperinsulinemia; non insulin dependent diabetes mellitus (NIDDM); arterial hypertension; central (visceral) obesity; and dyslipidemia. In addition to the major late-stage complications of NIDDM (diabetic angiopathy, atherosclerosis, diabetic nephropathy, diabetic neuropathy, and diabetic ocular complications such as retinopathy, cataract formation and glaucoma), many other conditions are linked to NIDDM, including dyslipidemia glucocorticoid induced insulin resistance, dyslipidemia, polycysitic ovarian syndrome, obesity, hyperglycemia, hyperlipidemia, hypercholerteremia, hypertriglyceridemia, hyperinsulinemia, and hypertension. Brief definitions of these conditions are available in any medical dictionary, for instance, Stedman's Medical Dictionary.

As mentioned above, the above described compounds may be used to stimulate insulin release. Such activity may be in vitro or in vivo. The amount of the TRPM5 inhibitor, such as a compound of Formula I, or any of the specific subgroups, subclasses, or specific compounds described above, used to stimulate insulin release may not necessarily be the same when used in vivo compared to in vitro. Factors such as pharmacokinetics and pharmacodynamics of the particular compound may require that a larger or smaller amount of the TRPM5 inhibitor, such as a compound of Formula I, or any of the specific subgroups, subclasses, or specific compounds described above, be used when increasing insulin release in vivo.

The invention includes a method of treating diabetes mellitus in an animal, preferably a mammal, in need thereof comprising administering to the subject an effective amount of a TRPM5 inhibitor, such as a compound according to Formula I, or any of the specific subgroups, subclasses, or specific compounds described above, or a pharmaceutically acceptable salt thereof. The method also includes a method of preventing diabetes mellitus in an animal, preferably a human or other mammal, in need thereof comprising administering to a subject an insulin secretion enhancing amount of a TRPM5 inhibitor, such as a compound according to Formula I, or any of the specific subgroups, subclasses, or specific compounds described above, or a pharmaceutically acceptable salt thereof.

The invention also includes a method for treating insulin resistance syndrome in an animal, preferably a human or other mammal, in need thereof, comprising administering the subject an effective amount of a TRPM5 inhibitor, such as a compound of Formula I or any of the specific subgroups, subclasses, or specific compounds described above, or a pharmaceutically acceptable salt thereof. The invention also includes a method for treating or preventing insulin resistance in a mammal comprising administering to said mammal an effective amount of a TRPM5 inhibitor, such as a compound of Formula I, or any of the specific subgroups, subclasses, or a pharmaceutically acceptable salt thereof.

The invention includes a method of treating hyperglycemia in an animal, preferably a human or other mammal, in need thereof comprising administering to the subject an effective amount of a TRPM5 inhibitor, such as a compound according to Formula I, or any of the specific subgroups, subclasses, or specific compounds described above, or a pharmaceutically acceptable salt thereof. The method also includes a method of preventing hyperglycemia in an animal, preferably in a human or other mammal, comprising administering to a subject an insulin secretion enhancing amount of a TRPM5 inhibitor, such as a compound according to Formula I, or any of the specific subgroups, subclasses, or specific compounds described above, or a pharmaceutically acceptable salt thereof.

The invention is also directed to a method of enhancing GLP-1 release from a cell, comprising administering an effective amount of a TRPM5 inhibitor, such as a compound according to Formula I, or any of the specific subgroups, subclasses, or specific compounds described above, or a pharmaceutically acceptable salt thereof. As discussed above, GLP-1 stimulates insulin synthesis and secretion from beta cells of the islets of Langerhans after food intake, thereby lowering blood glucose levels. GLP-1 is a 37-amino acid peptide and a product of proglucagon. A subsequent endogenous cleavage between cleavage between the sixth and seventh position produces the biologically active GLP-1 (7-37) peptide. GLP-1 is secreted from the L-type enteroendocrine cells in the luminal surface of the gut upon glucose intake. GLP-1 is also released in response to other stimuli. GLP-1 acts through a G-protein-coupled cell-surface receptor, specifically GLP-1R, and is regulated by T1R taste receptors and gustducin. See Kokrashvili et al., AChemS XXIX Abstract, 246 (2007). Studies have shown that α-gustducin couples sweet receptor T1R3 in sugar- and sweetener-stimulated secretion of GLP-1 from the L-type enteroendocrine cells. See Jang et al. *Proc. Natl. Acad. Sci. USA,* 104(38): 15069-15074 (2007).

GLP-1 possesses several physiological functions: 1) it stimulates insulin synthesis from the pancreatic islet cells in a glucose-dependent manner, thereby lowering blood glucose levels; 2) it decreases glucagon secretion from the pancreas; 3) it increases beta cell mass and insulin gene expression; 4) it inhibits gastric secretion and emptying; 5) it dose-dependently inhibits food intake by increasing satiety; and 6) it promotes weight loss. Several roles of GLP-1 are described by U.S. Pat. No. 6,583,118, U.S. Pat. No. 7,211,557; U.S. Patent Appl. Pub. No. 2005/0244810; Deacon, *Regulatory Peptides* 128:117-124 (2005); Turton et al., *Nature,* 379:69-72 (1996).

Some research has been done to identify non-natural peptide and small-molecule agonists for the GLP-1 receptor. Such compounds would be useful for treating type 2 diabetes, among other uses. These compounds mimic the effect of GLP-1 in that they potentiate glucose-induced insulin release from islet cells. For example, exenatide is a synthetic version of exendin-4, a naturally occurring peptide originally isolated from Gila monster saliva. Exenatide is now approved by the U.S. Food and Drug Administration for adjunctive therapy to improve glycemic control in patients with type 2 diabetes mellitus who are taking metformin, a sulfonylurea, or a combination of metformin and a sulfonylurea but have not achieved adequate glycemic control. Other potential agents that mimic the effect of GLP-1 are being developed. See, e.g., Knudsen et al., Small-molecule agonists for the glucagon-like peptide 1 receptor, *Proc. Natl. Acad. Sci. USA* 104(3): 937-942 (2007).

Thus, another aspect of the present invention is a method of stimulating release of GLP-1 by administration of a TRPM5 inhibitor. The prior art has not suggested that TRPM5 inhibitors, such as those exemplified herein, can be used to enhance the release of GLP-1, thereby increasing the beneficial effects of GLP-1. Thus, in certain embodiments, the present invention provides a method of enhancing the release of GLP-1 from intestinal cells, such as small intestine cells, with the subsequent effect of enhancing the release of insulin from pancreatic cells.

The TRPM5 inhibitor, such as a compound according to Formula I or any of the specific examples, can be administered to a cell or to a whole organism to obtain the enhanced GLP-1 release. Additionally, the TRPM5 inhibitor can be administered by itself or together with an agent known to cause the release of GLP-1 secretion, such as glucose. By way of example, the TRPM5 used in the invention can be a TRPM5 inhibitor that has an $IC_{50}$ of about 1 micromolar or less, preferably of about 100 nanomolar or less. In some embodiments, the TRPM5 inhibitor used in the method inhibits the TRPM5 receptor by at least 75%, preferably 90%, at a concentration of 5 micromolar or less.

As used herein, "GLP-1" or glucagon-like peptide-1 (GLP-1), is a gastrointestinal protein hormone which enhances insulin secretion by administration of nutrient, such as glucose, carbohydrate, fat, proteins, or mixed amino acids. The physiological roles of GLP-1 and the various proposed mechanisms of GLP-1 release after nutrient ingestion are described, for instance, by Kreymann et al., *Lancet* 2:1300-1304 (1987) and by Deacon, *Regulatory Peptides* 128: 117-124 (2005). Unless otherwise stated, "GLP-1" means GLP-1 (7-37). By custom in the art, the amino-terminus of GLP-1 (7-37) has been assigned number 7 and the carboxy-terminus, number 37. The amino acid sequence of GLP-1 (7-37) is well-known in the art, but is presented as follows: $NH_2$-His-Als-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-COOH.

In certain embodiments, the TRPM5 inhibitor causes in increase of GLP-1 release of about 5% to about 50%, or from about 10% to about 70%, or from about 25% to about 100%. In other embodiments, the TRPM5 inhibitor increases the amount of GLP-1 released from the intestinal cells by about 25%, 50%, 75%, or 100%.

Preferably, the method of increasing GLP-1 release is used on a mammal, such as a human or other primate. In other instances, the subject of the method can be a pet, such as a dog or cat.

Detection of GLP-1 release can be performed based on methods known to one of ordinary skill in the art, including those described herein. See, e.g., F. Reinmann, et al., *Diabetes,* 55(Supp. 2): S78-S-85 (2006).

The invention also includes a method of decreasing gastric secretion and emptying in an animal, preferably a human or other mammal, in need thereof comprising administering to the subject an effective amount of a TRPM5 inhibitor, such as a compound according to Formula I, or any of the specific subgroups, subclasses, or specific compounds described above, or a pharmaceutically acceptable salt thereof.

The invention further includes a method of inhibiting food intake in an animal, preferably a human or other mammal, in need thereof comprising administering to the subject an effective amount of a TRPM5 inhibitor, such as a compound according to Formula I, or any of the specific subgroups, subclasses, or specific compounds described above, or a pharmaceutically acceptable salt thereof. GLP-1 is known to play a significant role in the regulation of the physiological response to feeding. GLP-1 is processed from proglucagon and is released into the blood from the endocrine L-cells mainly located in the distal small intestine and colon in response to ingestion of a meal. GLP-1 acts through a G protein-coupled cell surface receptor (GLP-1R) and enhances nutrient-induced insulin synthesis and release. GLP-1 stimulates insulin secretion (insulinotropic action) and cAMP formation. GLP-1 (7-36) amide stimulates insulin releaser lowers glucagon secretion, and inhibits gastric secretion and emptying. These gastrointestinal effects of GLP-1 are not found in vagotomized subjects, pointing to a centrally-mediated effect. GLP-1 binds with high affinity to isolated rat adipocytes, activating cAMP production (Valverde et al., 1993) and stimulating lipogenesis or lipolysis. GLP-1 stimulates glycogen synthesis, glucose oxidation, and lactate formation in rat skeletal muscle. Thus, based on the inventors observations, the TRPM5 inhibitors described herein can be used to inhibit food intake because the TRPM5 inhibitors increase GLP-1 release.

The invention further includes a method of decreasing glucagon secretion in an animal, preferably a human or other mammal, in need thereof comprising administering to the subject an effective amount of a TRPM5 inhibitor, such as a compound according to Formula I, or any of the specific subgroups, subclasses, or specific compounds described above, or a pharmaceutically acceptable salt thereof.

Glucagon is a hormone consisting of a straight-chain polypeptide of 29 amino acid residues, extracted from pancreatic alpha cells. Its physiological roles, such as elevating blood glucose concentration and activating hepatic phosphorylase, are available to practioners of the art, for instance, in Stedman's Medical Dictionary, $26^{th}$ Ed. (1990) at 729.

The invention further includes a method of enhancing insulin sensitivity in an animal, preferably a human or other mammal, in need thereof comprising administering to the subject an effective amount of a TRPM5 inhibitor, such as a compound according to Formula I, or any of the specific subgroups, subclasses, or specific compounds described above, or a pharmaceutically acceptable salt thereof.

The invention further includes a method of increasing beta cell mass of the islets of Langerhans and insulin gene expression in an animal, preferably a human or other mammal, in need thereof, comprising administering to the subject an effective amount of a TRPM5 inhibitor, such as a compound according to Formula I, or any of the specific subgroups, subclasses, or specific compounds described above, or a pharmaceutically acceptable salt thereof.

The invention includes a method of treating or preventing obesity in an animal, preferably a human or other mammal, in need thereof comprising administering to the subject an effective amount of a TRPM5 inhibitor, such as a compound according to Formula I, or any of the specific subgroups, subclasses, or specific compounds described above, or a pharmaceutically acceptable salt thereof.

As used here, "obesity" refers to an abnormal increase of fat in the subcutaneous connective tissues. Stedman's Medical Dictionary, $26^{th}$ Ed. (1990) at 1235.

In each of the embodiments of methods described above, the subject of the method, unless otherwise limited to, may be any animal which is need of the particular treatment or effect of the method. Such animals include but are not limited to a cow, horse, sheep, pig, chicken, turkey, quail, cat, dog, mouse, rat, rabbit, monkey, or guinea pig insulin secreting cell. In other embodiments, the animal is a livestock animal, a domesticated animal, or an animal kept as a pet. In particular embodiments, the subject of the claimed method is a human.

In general, however, a suitable dose will be in the range of from about 0.005 to about 100 mg/kg, e.g., from about 0.1 to about 75 mg/kg of body weight per day, such as 0.03 to about 50 mg per kilogram body weight of the recipient per day, preferably in the range of 0.06 to 90 mg/kg/day, most preferably in the range of 0.15 to 60 mg/kg/day. In other embodiments, the suitable dosage will be about 0.1 mg/day to about 2000 mg/day, administered as a single dosage or multiple doses throughout the day.

The compound may conveniently be administered in unit dosage form; for example, containing 0.05 to 1000 mg, conveniently 0.1 to 750 mg, most conveniently, 0.5 to 500 mg of active ingredient per unit dosage form.

The TRPM5 inhibitor, such as a compound according to Formula I, or any of the specific subgroups, subclasses, or specific compounds described above, can be typically present in a dosage form in an amount ranging from about 0.1% to about 100% by weight, preferably about 1% to about 80% by weight. The present invention also contemplates an amount of about 1% to about 50%, preferably about 5% to about 20%, about 8%, 15%, or 18%, by weight, of the dosage form.

Ideally, the TRPM5 inhibitor, such as a compound of Formula I should be administered to achieve peak plasma concentrations of the active compound of from about 0.005 to about 75 µM, preferably, about 0.01 to 50 µM, most preferably, about 0.02 to about 30 µM. This may be achieved, for example, by the intravenous injection of a 0.0005 to 5% solution of the active ingredient, optionally in saline, or orally administered as a bolus containing about 0.01-1 mg of the active ingredient. Desirable blood levels may be maintained by continuous infusion to provide about 0.0001-5 mg/kg/hr or by intermittent infusions containing about 0.004-15 mg/kg of the active ingredient(s).

The method may be performed such that the insulin secretion, GLP-1 secretion, or insulin sensitivity being enhanced by the TRPM5 inhibitor, such as a compound of Formula I is enhanced by at least about 10%, 20%, 30%, 40%, 50%, 60%, 70%, 80%, 90%, or 95%, or from about 60% to about 99%, or alternatively from about 20% to about 50%. Thus, in a more specific embodiment, the method comprises administering a dosage form comprising one or more TRPM5 inhibitors, such as compounds according to Formula I, wherein the one or more compounds according to Formula I are present in an amount sufficient to enhance insulin secretion, GLP-1 secretion, or insulin sensitivity by at least about 10%, 20%, 30%, 40%, 50%, 60%, 70%, 80%, 90%, or 95%, or from about 60% to about 99%, or alternatively from about 30% to about 70%. Of course, in other embodiments, the insulin secretion, GLP-1 secretion, or insulin sensitivity may be enhanced to differing extents.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

In another embodiment, the above described compounds may be used to enhance insulin or GLP-1 secretion from a cell or enhance insulin sensitivity of a cell. Such enhancement may be in vitro or in vivo. The amount of the TRPM5 inhibitor, such as a compound of Formula I, or any of the specific subgroups, subclasses, or specific compounds described above, used to enhance insulin secretion, insulin sensitivity, or GLP-1 secretion may not necessarily be the same when used in vivo compared to in vitro. Factors such as pharmacokinetics and pharmacodynamics of the particular compound may require that a larger or smaller amount of the TRPM5 inhibitor, such as a compound of Formula I, or any of the specific subgroups, subclasses, or specific compounds described above, be used when pancreatic cell in vivo. Accordingly, one aspect of the present invention is a method of enhancing insulin release and GLP-1 secretion from a cell or enhancing insulin sensitivity of a cell, comprising contacting the cell with a TRPM5 inhibitor, such as a compound according to Formula I, or any of the specific subgroups, subclasses, or specific compounds described above.

In one embodiment of this aspect of the present invention, the method comprises contacting a cell, preferably a pancreatic cell, with a TRPM5 inhibitor, such as a compound of Formula I, or any of the specific subgroups, subclasses, or specific compounds described above, wherein said cell secretes insulin.

In one embodiment of this aspect of the present invention, the method comprises contacting a cell, preferably an L-type enteroendocrine cell, with a TRPM5 inhibitor, such as a compound of Formula I, or any of the specific subgroups, subclasses, or specific compounds described above, wherein said cell secretes GLP-1.

The present invention is also directed to a method of enhancing insulin and GLP-1 release from a cell or enhancing insulin sensitivity of a cell, comprising contacting said cell with a TRPM5 inhibitor, such as a compound of Formula I, or any of the specific subclasses and specific compounds listed above, and enhancing the insulin secretion, GLP-1 secretion, or insulin sensitivity of the cell by at least about 10%, 20%, 30%, 40%, 50%, 60%, 70%, 80%, 90%, or 95%, or from about 50% to about 99%. In another embodiment, the method comprises contacting said cell with TRPM5 inhibitor, such as a compound of Formula I, or any of the specific subclasses and specific compounds listed above, and enhancing the insulin secretion, GLP-1 secretion, or insulin sensitivity of the cell by about 10% to about 50%. In another embodiment, the present invention is directed to a method of enhancing insulin secretion or GLP-1 secretion from a cell or enhancing insulin sensitivity of a cell, comprising contacting said cell with a TRPM5 inhibitor, such as a compound of Formula I, or any of the specific subclasses and specific compounds listed above, and enhancing the insulin secretion, GLP-1 secretion, or insulin sensitivity by at least about 10%, 20%, 30%, 40%, 50%, 60%, 70%, 80%, 90%, or 95%, or from about 50% to about 99%, or alternatively from about 10% to about 50%, and wherein said cell is a naturally occurring cell. In another embodiment, the present invention is directed to a method of enhancing insulin secretion or GLP-1 secretion from a cell, or enhancing insulin sensitivity of a cell, comprising contacting said cell with a TRPM5 inhibitor, such as a compound of Formula I, or any of the specific subclasses or specific compounds listed above, and enhancing the insulin secretion, GLP-1 secretion, or insulin sensitivity by at least about 10%, 20%, 30%, 40%, 50%, 60%, 70%, 80%, 90%, or 95%, or from about 50% to about 99%, or alternatively from about 10% to about 50%, and wherein said cell is a naturally occurring human insulin secreting cell or GLP-1 secreting cell.

Any amount of the TRPM5 inhibitor, such as a compound of Formula I that provides the desired degree of enhancement can be used. For example, a single dose or two to four divided daily doses, provided on a basis of about 0.001 to 100 mg per kilogram of body weight per day, preferably about 0.01 to about 25 mg/kg of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As used herein, the term "enhancing" and grammatical variants thereof refers to increasing with the amount of or the degree of. For example, enhancing insulin release or GLP-1 release from a cell means increasing the amount of insulin or GLP-1 that is released by the cell. Similarly, enhancing insulin sensitivity of a cell means increasing the degree of insulin sensitivity of a cell. Enhancing includes but is not necessarily limited to modulating, modifying, activating, and the like.

Compositions

The present invention is also directed to various compositions useful for treating diabetes mellitus, insulin resistance syndrome, hyperglycemia, and obesity comprising a TRPM5 inhibitor, such as a compound of Formula I or a physiologically acceptable salt thereof.

The present invention is also directed to various compositions useful for increasing beta cell mass of the islets of Langerhans and insulin gene expression, decreasing gastric secretion and emptying and glucagon secretion, and inhibiting food intake, comprising a TRPM5 inhibitor, such as a compound of Formula I or a physiologically acceptable salt thereof.

In one aspect, the present invention is directed to a pharmaceutical composition comprising a TRPM5 inhibitor, such as a compound of Formula I, as defined above, including any of the specific embodiments, subclasses, or species described above, and one or more pharmaceutically acceptable carriers. Preferred compositions of the present invention are pharmaceutical compositions comprising a compound selected from one or more embodiments listed above, and one or more pharmaceutically acceptable excipients.

The pharmaceutical compositions of the present invention can be in any form suitable to achieve their intended purpose. Preferably, however, the composition is one which can be administered buccally or orally. Alternatively, the pharmaceutical composition may be an oral or nasal spray.

The pharmaceutical compositions of the invention can be in any form suitable for administration to any animal that can experience the beneficial effects of one or more TRPM5 inhibitors, such as compounds according to Formula I, or any of the specific subgroups, subclasses, or specific compounds described above. Foremost among such animals are humans, although the invention is not intended to be so limited. Other suitable animals include canines, felines, dogs, cats, livestock, horses, cattle, sheep, and the like. A veterinary composition, as used herein, refers to a pharmaceutical composition that suitable for non-human animals. Such veterinary compositions are known in the art.

The pharmaceutical preparations of the present invention can be manufactured using known methods, for example, by means of conventional mixing, granulating, dragée-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Pharmaceutical excipients are well known in the art. Suitable excipients include fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethylstarch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragée cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agaragar, and tragacanth, and mixtures thereof.

In a further embodiment, the invention is directed to a chewable tablet comprising a medically effective amount of a TRPM5 inhibitor, such as one or more compounds according to Formula I, and one or more biologically active agents. Chewable tablets are known in the art. See, e.g., U.S. Pat. Nos. 4,684,534 and 6,060,078, each of which is incorporated by reference in its entirety.

In another embodiment, the present invention is directed to an orally disintegrating composition wherein said orally disintegrating composition further comprises TRPM5 inhibitor, such as one or more compounds according to Formula I, or any of the specific subgroups, subclasses, or specific compounds described above. Orally disintegrating tablets are known in the art. See, e.g., U.S. Pat. Nos. 6,368,625 and 6,316,029, each of which is hereby incorporated by reference in its entirety.

In another embodiment, the present invention is further directed to a nasal composition further comprising a medically effective amount of TRPM5 inhibitor, such as one or more compounds according to Formula I, or any of the specific subgroups, subclasses, or specific compounds described above. Nasal sprays are known in the art. See, e.g., U.S. Pat. No. 6,187,332. By way of a nonlimiting example, a nasal spray composition according to the present invention comprises water (such as 95-98 weight percent), a citrate (such as 0.02 M citrate anion to 0.06 M citrate anion), a compound according to Formula I, and optionally phosphate (such as 0.03 M phosphate to 0.09 M phosphate).

In another embodiment, the present invention is directed to a solid dosage form comprising a water and/or saliva activated effervescent granule, such as one having a controllable rate of effervescence, and a TRPM5 inhibitor, such as a compound according to Formula I, or any of the specific subgroups, subclasses, or specific compounds described above. Effervescent pharmaceutical compositions are known in the art. See, e.g., U.S. Pat. No. 6,649,186, which is incorporated by reference in its entirety.

In another embodiment, the present invention is directed to a film-shaped or wafer-shaped pharmaceutical composition that comprises a TRPM5 inhibitor, such as a compound according to Formula I, or any of the specific subgroups, subclasses, or specific compounds described above, and is capable of disintegrating. Such a film-shaped or wafer-shaped pharmaceutical composition can be configured, for example, as quickly disintegrating administration forms, e.g., administration forms disintegrating within a period of 1 second up to 3 minutes, or as slowly disintegrating administration forms, e.g., administration forms disintegrating within a period of 3 to 15 minutes.

The indicated disintegration times can be set to the abovementioned ranges by using, for example, matrix-forming polymers which have different disintegrating, or solubility, characteristics. Thus, by mixing the corresponding polymer components, the disintegration time can be adjusted. In addition, disintegrants are known which "draw" water into the matrix and cause the matrix to burst open from within. As a consequence, certain embodiments of the invention include such disintegrants for the purpose of adjusting the disintegration time.

Suitable are polymers for use in the film-shaped or wafer-shaped pharmaceutical composition include cellulose derivatives, polyvinyl alcohol (e.g. MOWIOL™), polyacrylates, polyvinyl pyrrolidone, cellulose ethers, such as ethyl cellulose, as well as polyvinyl alcohol, polyurethane, polymethacrylates, polymethyl methacrylates and derivatives and copolymerisates of the aforementioned polymers.

In certain embodiments, the total thickness of the film-shaped or wafer-shaped pharmaceutical composition according to the invention is preferably 5 µm up to 10 mm, preferably 30 µm to 2 mm, and with particular preference 0.1 mm to 1 mm. The pharmaceutical preparations may round, oval, elliptic, triangular, quadrangular or polygonal shape, but they may also have any rounded shape.

In another embodiment, the present invention is directed to a composition comprising a pharmaceutically active amount of a TRPM5 inhibitor, such as a compound according to Formula I, or any of the specific subgroups, subclasses, or specific compounds described above contained in a coating that surrounds a gum base formulation. Preferably, the coating comprises at least 50% by weight of the entire product. As the center is chewed, the medicament or agent is released into the saliva. For example, U.S. Pat. No. 6,773,716, which is incorporated herein by reference in its entirety, discloses a suitable medicament or agent contained in a coating that surrounds a gum base formulation. One or more compounds according to Formula I, or any of the specific subgroups, subclasses, or specific compounds described above, can be used in preparing the coating. The compound according to Formula I, or any of the specific subgroups, subclasses, or specific compounds described above, may be present in varying amounts, such as about 30% 50%, 75%, or 90%. In another embodiment, the compound according to Formula I may be present in about 30% to about 99%. In other embodiments, the compound according to Formula I is present in about 1% to about 30%.

In a further embodiment, the invention is directed to a pharmaceutical composition suitable for aerosol administration, comprising medically effective amount of a TRPM5 inhibitor, such as a compound according to Formula I, or any of the specific subgroups, subclasses, or specific compounds described above, and a suitable carrier. Aerosol compositions are known in the art. See, e.g., U.S. Pat. No. 5,011,678, which is hereby incorporated by reference in its entirety. As a non-limiting example, an aerosol composition according to the present invention may comprise TRPM5 inhibitor, such as one or more compounds according to Formula I, or any of the specific subgroups, subclasses, or specific compounds described above and a biocompatible propellant, such as a (hydro/fluoro)carbon propellant.

In a further embodiment, the invention is directed to a transdermal drug delivery composition, comprising medically effective amount of a TRPM5 inhibitor, such as a compound according to Formula I, or any of the specific subgroups, subclasses, or specific compounds described above. Transdermal drug delivery compositions, such as devices, are designed to deliver a therapeutically effective amount of drug across the skin of a patient. Devices known to the art include reservoir type devices involving membranes that control the rate of drug release to the skin and devices involving a dispersion of the drug in a matrix. Transdermal drug delivery compositions, such as transdermal patches, are known in the art.

In certain embodiments, the pharmaceutical compositions of the invention comprise from about 0.001 mg to about 1000 mg of a TRPM5 inhibitor, such as a compound of Formula I, or any of the specific subgroups, subclasses, or specific compounds described above. In another embodiment, the compositions of the invention comprise from about 0.01 mg to about 10 mg of a TRPM5 inhibitor, such as a compound of Formula I, or any of the specific subgroups, subclasses, or specific compounds described above.

The activity of a TRPM5 inhibitor, such as a compound according to Formula I, or any of the specific subgroups, subclasses, or specific compounds described above can be determined by testing said compound using a number of methods known in the art. For example, one can evaluate the ability of a compound to enhance insulin secretion, GLP-1 secretion, or insulin sensitivity by using an in vivo assay. This in vivo assay identifies the amount of insulin released by pancreatic cells or GLP-1 release by the L-type enteroendocrine cells in the presence of a TRPM5 inhibitor, such as a compound of Formula I.

The activity of a TRPM5 inhibitor, such as a compound according to Formula I, or any of the specific subgroups, subclasses, or specific compounds described above, can also be determined by means of the assay described in Example 23.

Methods of Preparation of Compounds

TRPM5 inhibitors can be identified using the assays and methods disclosed herein. Additionally, the assay disclosed in U.S. Published Patent Application No. 20050019830, hereby incorporated by reference in its entirety, can be used to identify compounds that are inhibitors of TRPM5. Such compounds can be prepared use techniques known to one of skill in the art.

A compound according to Formula I can be synthesized according to methods outlined in the following descriptions. The compounds for use in the present invention can be synthesized using procedures known in the art.

The following general schemes illustrate synthetic methods used to prepare compounds of the present invention. In one process, a compound of Formula I can be prepared by condensing a suitable acylated hydrazide with a suitable ketone or aldehyde in a suitable organic solvent, such as ethanol, 2-propanol, tetrahydrofuran, toluene, etc., and mixtures thereof, as shown in Scheme 1 (wherein $R^1$, $R^2$, $R^3$, $R^4$, $L^1$, and $L^2$ are defined as above). The presence of a water quenching agent such as molecular sieves or dry potassium carbonate may be useful in the process. An acid or a base catalysis may be used to facilitate the condensation. Acid catalysts include, but are not limited to, p-toluenesulfonic acid, methylsulfonic acid, phosphoric acid, and sulfuric acid. Base catalysts include, but are not limited to, triethylamine, diisopropylethylamine, pyridine, N-methylmorpholine, sodium carbonate, potassium carbonate, and sodium carbonate.

Scheme 1.

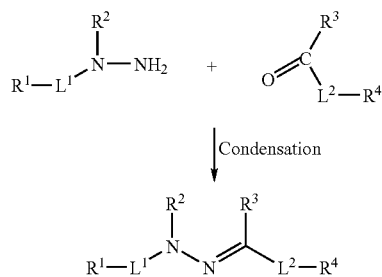

In an alternative process, certain compounds according to Formula I, wherein $R^2$ is H, can be prepared as shown in Scheme 2 (wherein $R^1$, $R^2$, $R^3$, $R^4$, $L^1$, and $L^2$ are defined as above). According to this process, a suitable carboxylic acid is treated with a hydrazone of a suitable aldehyde or ketone to provide a compound according to Formula I. Carbonyldiimidazole and triethylamine can be employed as condensing agents in this reaction, although other suitable condensing agents may be used as well.

Scheme 2.

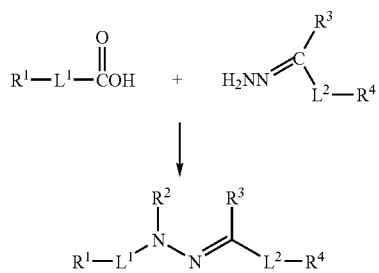

As a further example, the compounds of Formula I, wherein $R^1$ and $R^2$ are aryl groups, can be prepared by condensing an acylated hydrazide (such as compound 1) with an aldehyde (such as compound 2) in a suitable organic solvent, such as ethanol, 2-propanol, tetrahydrofuran, toluene, etc., and mixtures thereof, and in the presence of a water quenching agent such as molecular sieves or dry potassium carbonate (Scheme 1). An acid or a base catalysis may be used to facilitate the condensation. Acid catalysts include, but are not limited to, p-toluenesulfonic acid, methylsulfonic acid, phosphoric acid, and sulfuric acid. Base catalysts include, but are not limited to, triethylamine, diisopropylethylamine, pyridine, N-methylmorpholine, sodium carbonate, potassium carbonate, and sodium carbonate. An example of this process is shown in Scheme 3.

Scheme 3

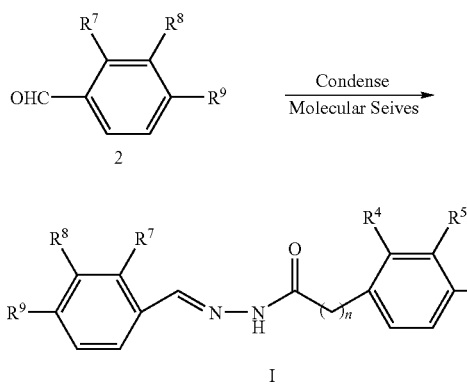

The variation of this method would include treating a suitable carboxylic acid (such as compound 3) with a hydrazone of a suitable aldehyde (such as compound 4) to provide compound I. The carbonyldiimidazole and triethylamine are usually employed as condensing agents in this reaction. An example of this process is shown in Scheme 4.

Scheme 4

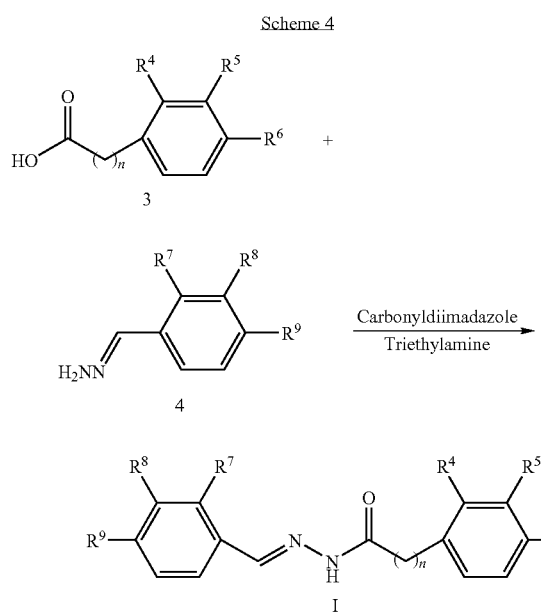

The reaction can also be carried out neat (e.g., without a solvent). After the reaction is complete, the product can be isolated by crystallization from solvents such as ethanol, dichloromethane, ethyl acetate, and toluene etc.

Similarly other compounds of this invention can be obtained from commercial sources and prepared by those skilled in the art. Starting materials are commercially available or they can be prepared by ordinary persons trained in the art. For example, compound 1 shown above can be prepared by reacting a carboxylic acid (such as compound 3) with a protected hydrazine (such as compound 5) in the presence of carbonyldiimidazole/triethyl amine to provide a protected acid hydrazide (such as compound 6). After the reaction is complete, the protecting group from the acid hydrazide (such as compound 6) can be removed under standard conditions (such as acidic conditions, e.g., trifluoroacetic acid) to provide a compound of formula I. An example of this process is shown in Scheme 5.

Scheme 5

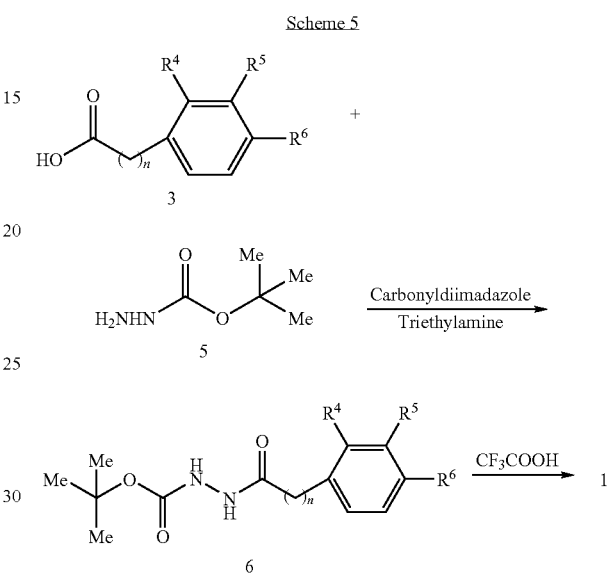

Other compounds of this invention can be prepared by slight variation of the methods described herein. These methods and others are described in the literature, such as Wyrzykiewicz and Prukala, *Polish J. Chem.* 72:694-702 (1998); and Elderfield and Wood, *J. Org. Chem.* 27:2463-2465 (1962), each of which is incorporated by reference in its entirety.

Additional compounds of Formula I (wherein $L^2$ is N=N) may be prepared by reacting a diazonium salt with a hydrazone. The reaction conditions used for this condensation are known to those skilled in the art of organic synthesis (for example, see *Synthesis*, 577-581 (1995); Chemical and Pharmaceutical Bulletin 42(11): 2363-2364 (1994); Tetrahedron 38(12):1793-1796 (1982)). The starting materials may be obtained commercially or may be prepared by commonly used organic reaction conditions.

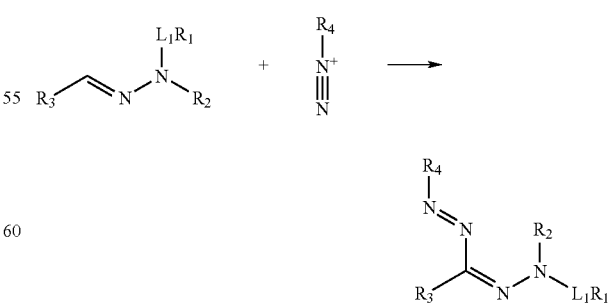

Further compounds of Formula I wherein $L^2$ is absent, $R^3$ and $R^4$ are cyano and $R^2$ is H, may be prepared by condensation of malononitrile with a diazonium salt. This reaction and conditions are known to those skilled in the art of organic synthesis (see, e.g., Archiv. der Pharmazie 337(3):140-147 (2004); Monatshefte fuer Chemie 130(11):1409-1418 (1999)).

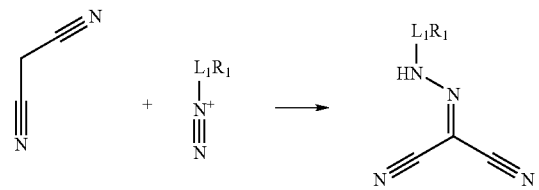

Additional compounds of Formula I in which $L^1$-$R^1$ is

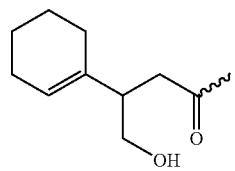

can be prepared by treating lactone A (see Zhurnal Organischeskoi Khimii 17(3):481-486 (1981)) with hydrazine in an alcoholic (e.g., methanol, ethanol, isopropanol) or other solvent:

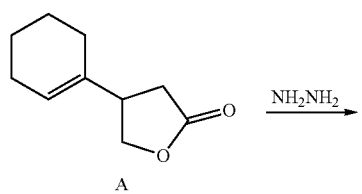

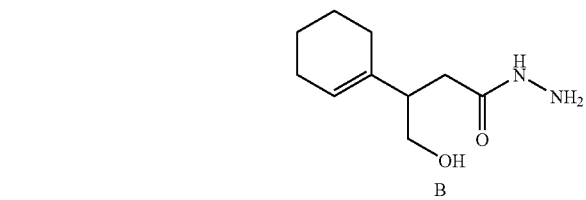

to provide acylhydrazone B which can be used as described herein.

Additional compounds of Formula I in which $L^1$-$R^1$ is

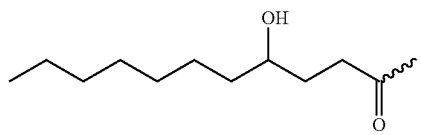

can be prepared from keto acid C (see Org. Syn. Coll. Vol. 9, 530). Ketoacid C is esterified with diazomethane, trimethylsilyldiazomethane or other reagent combination and the resultant ester is reduced with a selective reducing agent such as sodium borohydride in methanol or ethanol to provide intermediate D and/or its lactone. Intermediate D (or its lactone) is treated with an excess of hydrazine in an alcoholic (e.g., methanol, ethanol, isopropanol) or other solvent to provide intermediate E. This intermediate may be used as described herein for the preparation of compounds of Formula I.

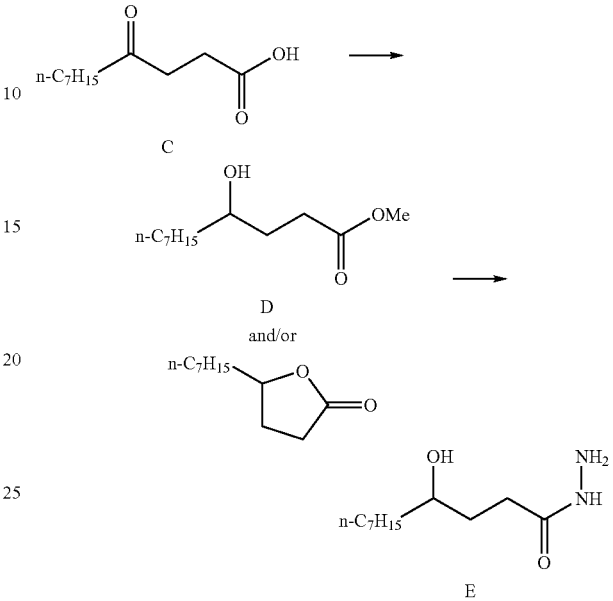

Additional compounds of Formula I in which $L^1$ is absent and $R^1$ is

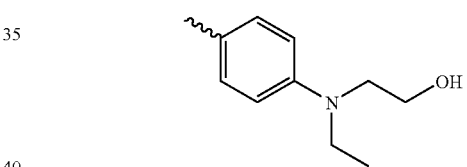

may be prepared from intermediate G. Intermediate G is prepared by reduction of the commercially available diazonium salt F with tin chloride (see, e.g., Journal of Heterocyclic Chemistry 24(4):1041-3 (1987)) or the like.

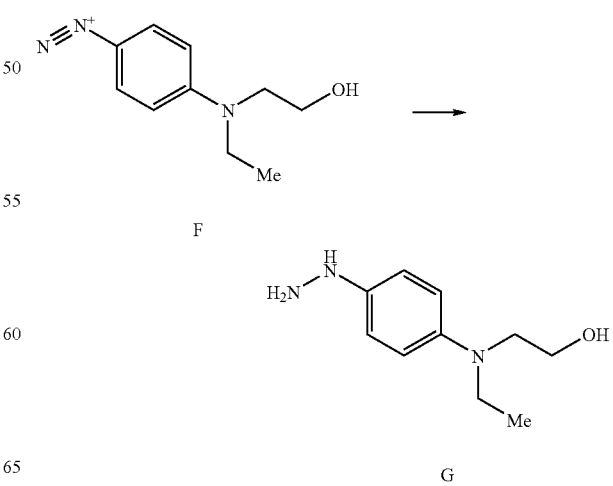

Additional compounds of Formula I in which L¹-R¹ is

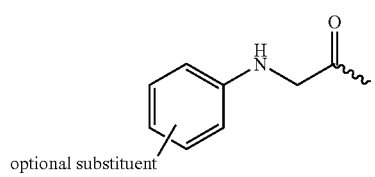

may be prepared from intermediate K. Intermediate K is prepared as shown in the scheme below. An aniline (H) is treated with a base such as potassium carbonate, another carbonate base, or a stronger base such as sodium hexamethyldisilazide or sodium hydride; and ethyl bromoacetate to provide J. Intermediate J is treated with an excess of hydrazine in an alcoholic or other solvent to provide K which is used as describe herein.

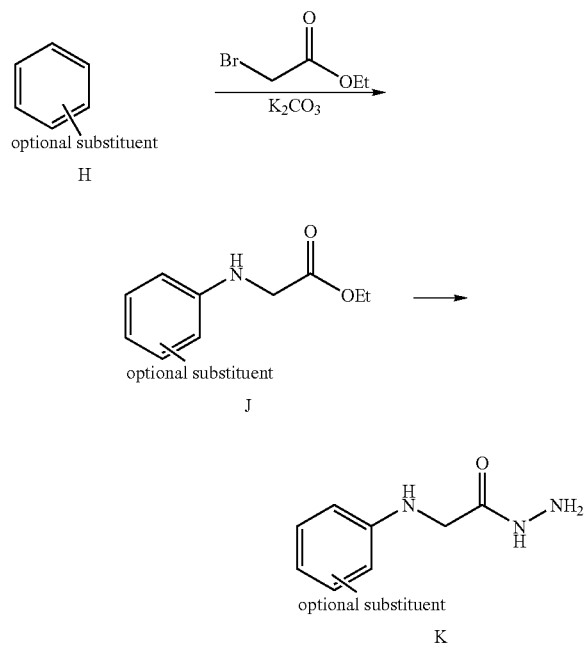

Additional compounds of Formula I in which L¹ is absent and R¹ is

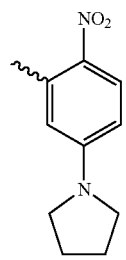

may be prepared from intermediate M. Intermediate M is obtained by treating the commercially available halide L with pyrrolidine as described in JCS Perkin 1, 2216-2221 (1976).

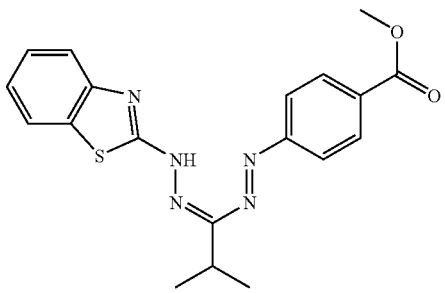

Of course, other methods and procedures known in the art may be used to prepare certain compounds of Formula I.

The following examples are illustrative, but not limiting, of the method, compounds, and compositions of the present invention. Each of the compounds listed below may be obtained from commercially available catalog companies, such as Aldrich RarechemLib, Aldrich Sigma, AlsInEx, Biotech Corp., Brandon/Berlex, Calbiochem, ChemBridge, Comgenex West, Foks H, G. & J. Research, IBS, ICN Biochemicals, Institute for Chemotherapy, Kodak, Lederle Labs, Ligand-CGX, Maybridge PRI, Menai Organics, Menai/Neurocrine, MicroSource, MPA Chemists, Mybrgd/ONYX, PRI-Peakdale, RADIAN, Receptor Research, RGI, Rhone-Poulenc, SPECS/BioSPECS/SYNTHESIA, T. Glinka, Tripos Modem, VWR, Zaleska, Zelinksy/Berlex, Aeros, and Chemica. The compounds were purified using conventional purification procedures, such as HPLC. The identity of the compound was confirmed using HPLC and mass spectrometry. As is known in the art and noted above, the hydrazone moiety can exist in either the E or the Z conformation. Thus, while a particular stereochemistry may be indicated for particular compounds described herein, it is understood that the invention includes all stereoisomers, and in particular all E and Z isomers. Other suitable modifications and adaptations of the variety of conditions and parameters normally encountered and obvious to those skilled in the art are within the spirit and scope of the invention.

EXAMPLES

Example 1

Methyl 4-((E)-((Z)-1-(2-(benzo[d]thiazol-2-yl)hydrazono)-2-methylpropyl)diazenyl)benzoate Molecular Formula: $C_{19}H_{19}N_5O_2S$; Molecular Weight: 381.5 (calculated).

Example 2

(E)-2-(4-Bromo-2-((2-(quinolin-8-yl)hydrazono)methyl)phenoxy)acetic Acid

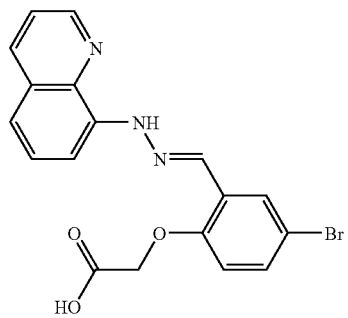

Molecular Formula: $C_{18}H_{14}BrN_3O_3$; Molecular Weight: 400 (calculated).

Example 3

(E)-N'-(3,4-Dimethoxybenzylidene)-2-(naphthalene-1-yl)acetohydrazide

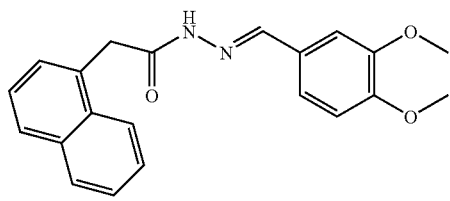

Molecular Formula: $C_{21}H_{20}N_2O_3$; Molecular Weight: 348 (calculated), 348 (found).

Example 4

(E)-N'-(3,4-Dimethoxybenzylidene)-2-phenylcyclopropanecarbohydrazide

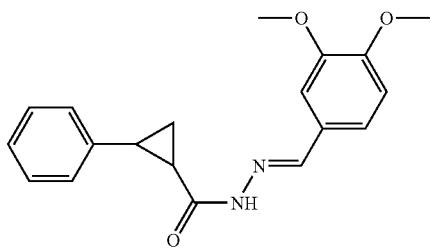

Molecular Formula: $C_{19}H_{20}N_2O_3$; Molecular Weight: 324 (calculated), 324 (found).

The enantiomers (R,R, R,S, S,S, and S,R) of Example 4 were separated by supercritical fluid chromatography using 20% methanol (flow rate 5 mL/min, 100 bar, 35° C.) on a 4.6×250 mm Diacel ODH column. HPLC chromatograph of separation is shown in FIG. 15.

Example 5

(E)-3-Cyclohexenyl-4-hydroxy-N'-(4-methoxybenzylidene)butanehydrazide

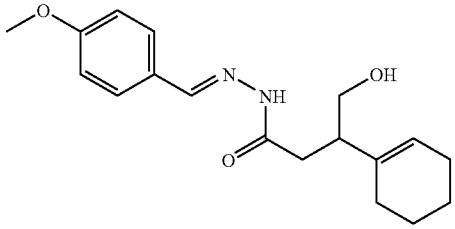

Molecular Formula: $C_{18}H_{24}N_2O_3$; Molecular Weight: 316.40 (calculated).

Example 6

(E)-N'-(3,4-Dimethoxybenzylidene)-4-hydroxyhexanehydrazide

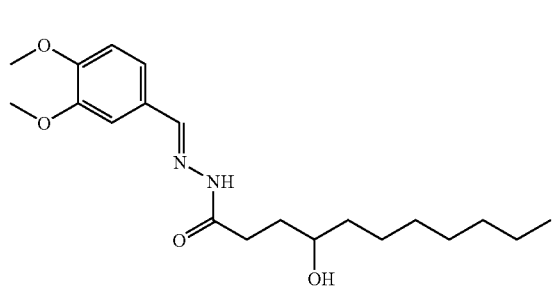

Molecular Formula: $C_{20}H_{30}N_2O_4$; Molecular Weight: 364.5 (calculated), 364 (found).

Example 7

2-((Z)-2-(Phenyl-((E)-phenyldiazenyl)-methylene)hydrazinyl)benzoic acid

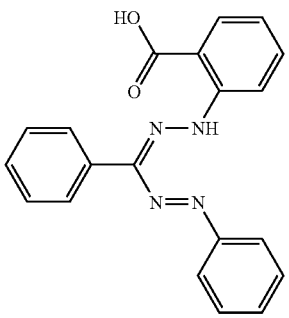

Molecular Formula: $C_{20}H_{16}N_4O_2$; Molecular Weight: 344.7 (calculated).

Example 8

(E)-N'-(3,4-Dimethoxybenzylidene)-2-(m-tolyloxy)acetohydrazide

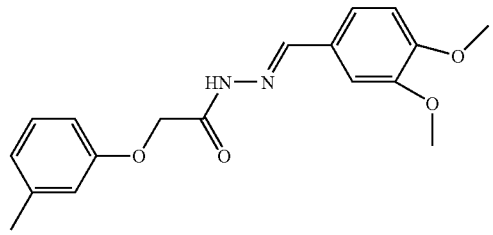

Molecular Formula: $C_{18}H_{20}N_2O_4$; Molecular Weight: 328 (calculated), 328 (found).

Example 9

(E)-N'-(4-(Allyloxy)-3-methoxybenzylidene)-2-(3-bromobenzylthio)acetohydrazide

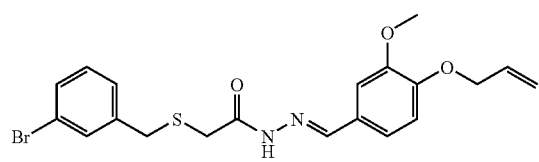

Molecular Formula: $C_{20}H_{21}BrN_2O_3S$; Molecular Weight: 449 (calculated), 447.9 (found).

Example 10

(E)-N'-(4-Isopropylbenzylidene)bicyclo[4.1.0]heptane-7-carbohydrazide

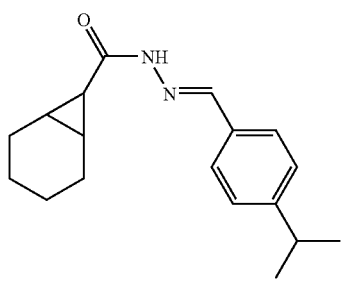

Molecular Formula: $C_{18}H_{24}N_2O$; Molecular Weight: 284 (calculated), 284 (found).

Example 11

(Z)-1,3,3-Trimethyl-2-((E)-2-(2-(4-nitrophenyl)hydrazono)ethylidene)indoline

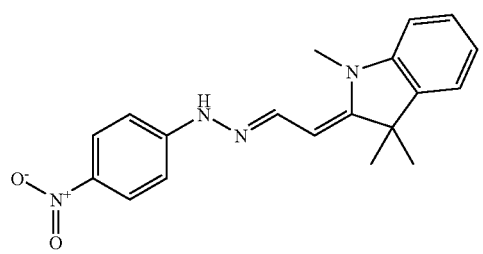

Molecular Formula: $C_{19}H_{20}N_4O_2$; Molecular Weight: 336 (calculated), 336 (found).

Example 12

(E)-N'-(4-(Diethylamino)-2-hydroxybenzylidene)-2-phenylcyclopropanecarbohydrazide

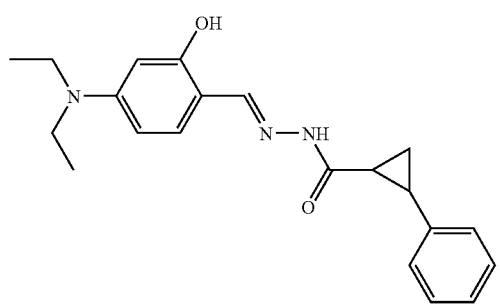

Molecular Formula: $C_{21}H_{25}N_3O_2$; Molecular Weight: 351 (calculated), 351 (found).

Example 13

(4-(Trifluoromethylthio)phenyl)carbonohydrazonoyldicyanide

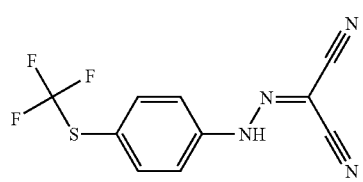

Molecular Formula: $C_{10}H_5F_3N_4S$; Molecular Weight: 270.24 (calculated).

Example 14

N-((E)-3-((Z)-2-(1,5-Dimethyl-2-oxoindolin-3-ylidene)hydrazinyl)-3-oxo-1-phenylprop-1-en-2-yl)benzamide

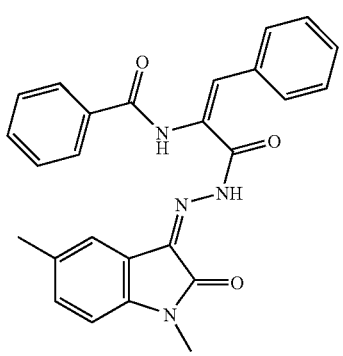

Molecular Formula: $C_{26}H_{22}N_4O_3$; Molecular Weight: 438.5 (calculated).

Example 15

(Z)-2-(2-((1-Butyl-1H-indol-3-yl)methylene)hydrazinyl)benzoic acid

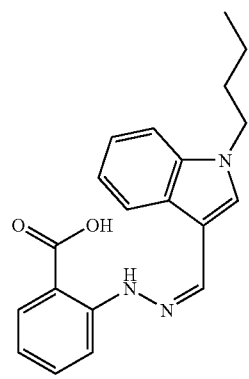

Molecular Formula: $C_{20}H_{21}N_3O_2$; Molecular Weight: 335.4 (calculated).

Example 16

(E)-4-((2-Benzyl-2-phenylhydrazono)methyl)pyridine

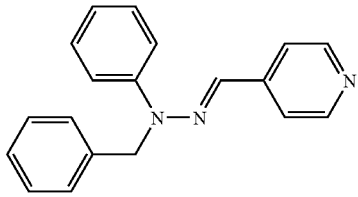

Molecular Formula: $C_{19}H_{17}N_3$; Molecular Weight: 287 (calculated), 287.2 (found).

Example 17

(Z)-N'-((1H-Pyrrol-2-yl)methylene)tricyclo[3.3.1.1^{3,7}]decane-3-carbohydrazide

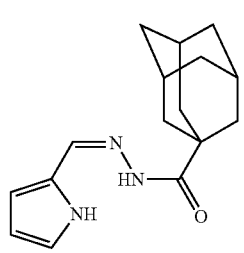

Molecular Formula: $C_{16}H_{21}N_3O$; Molecular Weight: 271 (calculated).

Example 18

(Z)-1-(2-(4-(Ethyl-(2-hydroxyethyl)-amino)phenyl)hydrazono)naphthalen-2(1H)-one

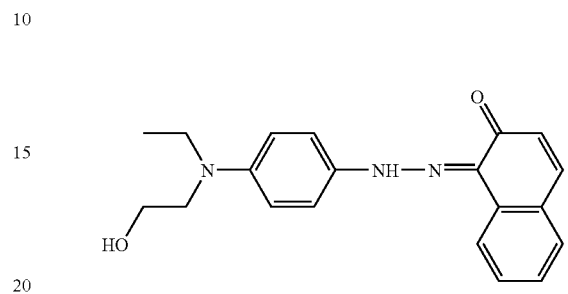

Molecular Formula: $C_{20}H_{21}N_3O_2$; Molecular Weight: 335 (calculated), 333.2 (found).

Example 19

(E)-4-((2-(5-Chloro-3-(trifluoromethyl)pyridin-2-yl)-2-2-methylhydrazono)methyl)benzene-1,3-diol

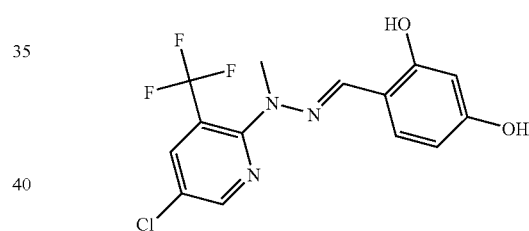

Molecular Formula: $C_{14}H_{11}ClF_3N_3O$; Molecular Weight: 345.7 (calculated), 344.9 (found).

Example 20

(E)-2-(3,4-Dimethylphenylamino)-N'-(4-morpholino-3-nitrobenzylidene)acetohydrazide

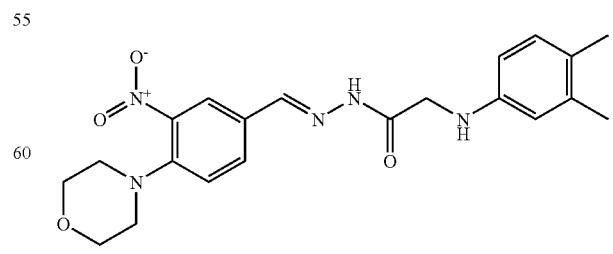

Molecular Formula: $C_{21}H_{25}N_5O_4$; Molecular Weight: 411.4 (calculated), 411.3 (found).

Example 21

(Z)-3-(2-Nitro-5-(pyrrolidin-1-yl)phenyl)hydrazono)quinuclidine

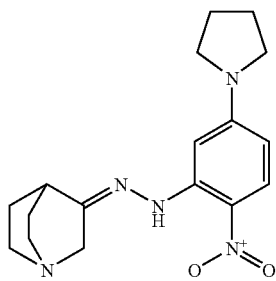

Molecular Formula: $C_{17}H_{23}N_5O_2$; Molecular Weight: 329.4 (calculated).

Example 22

(E)-2-((2-(1H-benzo[d]imidazol-2-yl)hydrazono)methyl)-5-(diethylamino)phenol

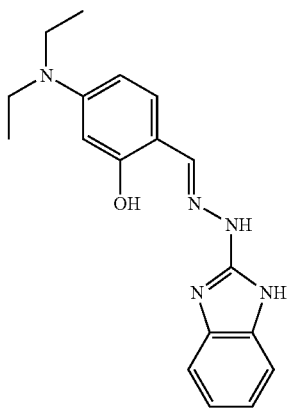

Molecular Formula: $C_{18}H_{21}N_5O$; Molecular Weight: 323.4 (calculated).

Example 23

3-Carbazol-9-ylpropionic acid (3,4-dimethoxybenzylidene)hydrazide

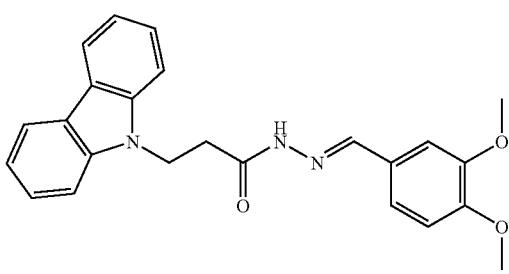

Molecular Formula: $C_{24}H_{23}N_3O_3$.

Example 24

(4,8-Dimethylquinolin-2-ylsulfanyl)acetic acid (3,4-dimethoxybenzylidene)hydrazide

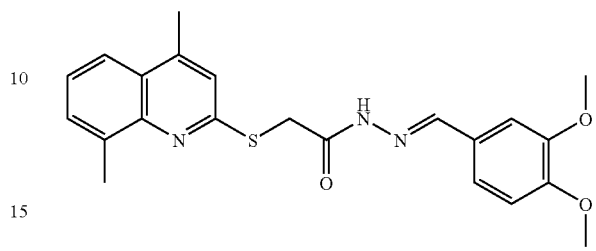

Molecular Formula: $C_{22}H_{22}N_3O_3$.

Example 25

Assay for Determining Insulin Release Enhancement by TRPM5 Inhibitors

Beta-TC-6 cells are an insulin-secreting cell line derived from transgenic mice expressing the large T-antigen of simian virus 40 (SV40) in pancreatic beta-cells as described by Poitout et al., *Diabetes,* 44:306-313 (1995). The cell line was obtained from ATCC cell bank CAT# CRL-11506 and grown in Dulbecco's Modified Eagle's Medium (DMEM) with 15% fetal bovine serum (FBS), 4 mM glutamine, 4.5 mM glucose 1500 mg/L sodium bicarbonate and 1× penn/strep antibiotic mix in a 37° C. incubator with 5% $CO_2$. Cultures were routinely split 1:2 twice a week with the aid of trypsin.

On the day before the assay $0.1 \times 10^6$ Beta-TC-6 cells were plated into each well of 96 well plates, and the cells cultured overnight in growth media.

On the next day, growth media was removed from the plate and the monolayers rinsed with phosphate buffered saline (PBS) and pre-incubated 30 mins at 37° C. in Krebs-Ringer Bicarbonate Buffer (KRBB) consisting of 118.5 mM NaCl, 2.54 mM $CaCl_2$, 1.19 mM $KH_2PO_4$, 4.74 mM KCl, 25 mM $NaHCO_3$, 1.19 mM $MgSO_4$, 10 mM HEPES buffer and 0.1% bovine serum albumin at pH 7.4. This buffer was removed and replaced with 100 μL of the same buffer containing various insulin release modulators: including various concentrations of glucose up to 12 mM and compounds up to 100 μM. Compounds stock solutions, e.g. 10-20 mM, were diluted in DMSO. Final DMSO concentrations in incubation buffer were 0.5% or less. Vehicle controls were included. Static incubations were then performed for 2 h at 37° C. The entire incubation volume was collected after the 2 h incubation for insulin assay.

ELISA Protocol for insulin determinations. The following protocol was used for doing ELISA using the Rat/Mouse Insulin ELISA Kit from Linco Research, Inc., CAT#EZRMI-13K and Amplex® Red Hydrogen Peroxide/Peroxidase Assay Kit, CAT#A22188, and Amplex® Red reagent (10-acetyl-3,7-dihydroxyphenoxazine) CAT#A12222.

All reagents were Pre-warmed to room temperature before setting up experiment.

1. Dilute the 10× washing buffer into 1× washing buffer. 50 mL+450 mL de-ionized water. Do 1:10 dilution to the cell culture supernatant (Beta-TC-6 cell incubation).

2. Use one column (8 wells) wells for standard samples and QC1 and QC2, typically 0 and 5 ng/mL of insulin. On some plates full standard curves for insulin obtained as shown below.

3. Cover the unused wells well. Wash each well 3 times with 300 μL of 1× washing buffer each time. (2 minutes each washing step on the shaker.) Decant Wash Buffer and remove the residual amount from all wells by inverting the plate and tapping it smartly onto absorbent towels several times. Do not let wells dry before proceeding to the next step.

4. Add 20 μL Assay Buffer into that blank well and 10 μL into those wells for standards and samples.

5. Add 10 μL rat insulin standards and samples to the appropriate wells.

6. Add 80 μL Detection Antibody to all wells. Cover the plate and incubate at room temperature for 2 hours.

7. Tear off the plate cover and decant solutions from the plate. Tap to remove residual solutions in well.

8. Wash well 3 times with diluted wash buffer 300 μL per well per wash (2 minutes each washing step on the shaker). Tap to remove residual solutions as before.

9. Add 100 μL Enzyme Solution to each well. Cover plate with sealer and incubate with moderate shaking at room temperature for 30 min on the microtiter plate shaker.

10. Remove sealer, decant solutions from the plate and tap plate to remove the residual fluid.

11. Wash wells 6 times with diluted Wash Buffer, 300 μL per well per wash. Decant and tap after each wash to remove residual buffer.

12. Prepare 5 mL working solution of 100 μL Amolex Red reagent containing 2.0 mM $H_2O_2$. 4.45 mL of 1× Reaction buffer+50 μL 10 mM Amplex Reagent+500 μL 20 mM $H_2O_2$.

13. Add 100 μL of the Amplex Red reagent/$H_2O_2$ to each well.

14. Incubate the reactions. Incubate at room temperature for 30 minutes, protected from light (using foil to wrap the plate). Then measure the fluorescence at 590 nm (the excitation range is 530-560 nm) at multiple time points in a Molecular Devices FlexStation.

The above procedure or minor variations thereof are used to determine the insulin-secreting enhancement of the TRPM5 inhibitors.

Example 26

Electrophysiology Studies for Cells Containing TRPM5

Whole-cell recordings of TRP channel currents were obtained from acutely trypsinized beta TC-6 cells and TRPM5-expressing HEK cells. The bath solution was Hank's Balanced Salt Solution, composed of (mM); 1.2 $CaCl_2$, 0.5 $MgCl_2$-$6H_2O$, 0.4 $MgSO_4$·$7H_2O$, 5.3 KCl, 0.4 $KH_2PO_4$, 137.9 NaCl, 0.3 $Na_2HPO_4$·$7H_2O$, and 5.5 D-Glucose, with 20 mM HEPES (Invitrogen), pH 7.4 (NaOH). The internal pipette solution contained, in mM: 135 glutamic acid, 8 NaCl, 9 $CaCl_2$, 10 HEPES and 10 EGTA, pH 7.2 (CsOH) (Sigma). Calculated concentration of free calcium in internal solution was 1.5 μM (http://www.stanford.edu/~cpatton/webmaxc/webmaxcS.htm). Recording pipettes were pulled using a Flaming/Brown Micropipette Puller (Sutter Instruments), from fire-polished borosilicate glass, to approximately 2 MΩ.

Voltage clamp recordings were obtained in whole cell mode using MultiClamp 700B amplifier and Digidata 1322A converter running on Clampex 9.2 software (Axon Instruments). Recordings were performed at room temperature. The recording protocol consisted of a ramp from −80 mV potential to +80 mV, followed by a step to −80 mV. Peak current was measured at three different voltages: −80 mV, after ramping to +80 mV, then following a return to −80 mV. Series resistance was automatically compensated immediately after the break-in, and the resulting capacitance measurements were used for current density calculations. Data were sampled at 5 kHz and filtered at 1 kHz.

Compounds were prepared as DMSO stocks. On the day of experiment they were dissolved in bath solution to 0.1% final DMSO concentrations. Rapid solution exchange (~100 ms) was achieved with the use of multi-barrel applicator (SF-72, Warner).

Example 27

Presence of mTRPM5 in Mouse Beta TC6 Cells

Beta TC-6 cells were grown and then spun down and using RNeasy Mini Kit (Cat #: 74104) from Qiagen RNA preps were made. The preps were DNased the second time with Invitrogen DNase I (Cat #: 18068-015). 1st strand cDNA synthesis were prepared using Invitrogen Superscript First-Strand Synthesis System for RT-PCR (Cat #: 12731-019). Both RT(+) and RT (−) cDNAs were made to check for the possibility of genomic contamination.

Using Platinum Taq DNA Polymerase from Invitrogen (Cat #: 10966-018) and forward and reverse primers specific for mtrpM5 both the RT(+) and RT(−) cDNAs were PCRed. The right size band was seen for the RT(+) product and there was no genomic contamination as can be seen from the absence of a band for the RT(−) cDNA. Results are shown in FIG. 14.

Example 28

Activity of Selected Compounds

Selected compounds of the invention were tested for their ability to increase insulin secretion. The results are shown in the following table. The compounds were tested at a concentration of 10 μM. The data indicate the percent enhancement of insulin secretion produced by the test compound compared to glucose-dependent insulin production. Also provided in the table is the activity of tolbutamide, which was tested at 30 μM.

| Example No. | Percent Enhancement of Insulin Secretion (10 μM) | $IC_{50}$ TRPM5 (μM) |
|---|---|---|
| 3 | 250 | 0.6 |
| 4 | 111 | 0.6 |
| 8 | 39 | 3 |
| 23 | 208 | 0.5 |
| 24 | 207 | 0.4 |
| Tolbutamide (30 μM) | 228 | — |

Example 29

Assay for Determining GLP-1 Release by TRPM5 Inhibitor Using GLUTag Cells

Mouse GLUTag cells are a native intestinal cell line which expresses TRPM5. The cell line was obtained from Dr. Daniel J. Drucker in the Division of Endocrinology, Department of Medicine, at University of Toronto, and grown in Invitrogen Dulbecco's Modified Eagle's Medium (DMEM) high glucose (Cat #: 11995) with 10% fetal bovine serum (FBS) and 1× penn/strep antibiotic mix in a 37° C. incubator with 5% $CO_2$.

All reagents and media were pre-warmed to room temperature prior to the beginning of the experiment. Substrate diluent and the light-sensitive Substrate were thawed out right before use.

Seeding of Cell Plate

BD 96-well Matrigel-coated plates (Fisher, Cat #: 08-774-166) with GLUTag cells were rehydrated using 100 μL of plating media (Invitrogen's (Cat #: 31985) OPTI-Modified Eagle's Medium (MEM) with 10% FBS and 1× penn/strep antibiotic mix) and incubated for 30 minutes in a 37° C. incubator with 5% $CO_2$. GLUTag cells were then trypsinized and counted. A cell dilution with seeding density of $7.5 \times 10^5$ cells/ml of GLUTag cells was created. The rehydration media was aspirated from the Matrigel coated plate. 100 mL of cell dilution were plated into each well of the plate. The plates were then incubated overnight in a 37° C. incubator with 5% $CO_2$.

The following protocol utilized the Millipore GLP-1 ELISA Kit (Cat. #: EGLP-35K) to analyze GLP-1 secretion from GLUTag cells in the presence of TRPM5 inhibitors/enhancers and glucose.

ELISA Assay Day 1

Stock solutions and dilution plates of TRPM5 inhibitors or enhancers were prepared. 1% of bovine serum albumin (BSA) was added to Krebb's Ringer Bicarbonate Buffer (KRBB) right before use. KRBB consists of 118.5 mM NaCl, 2.54 mM $CaCl_2.2H_2O$, 1.19 mM $KH_2PO4$, 4.74 mM KCl, 25 mM $NaHCO_3$, 1.19 mM $MgSO4.7H_2O$, and 10 mM HEPES buffer at pH 7.4. The cell plates were incubated with 100 μL of KRBB for 30 minutes. The KRBB buffer was then aspirated. This incubation step was repeated once. The KRBB buffer was aspirated and replaced with 150 μL of the same buffer containing various concentration of TRPM5 inhibitors or enhancers and glucose, i.e. 12.5 mM glucose and 1.5 μM TRPM5 inhibitors. KRBB buffer without the TRPM5 inhibitors/enhancers and glucose were also tested in triplicates. Static incubations of treated cells were then performed for 2 h in a 37° C. incubator with 5% $CO_2$.

During the last 30 minutes of the two-hour incubation, 96-well ELISA plates were prepared as follows. GLP-1 (Active) ELISA Plates coated with anti-GLP-1 monoclonal antibody were washed three times with 300 μL/well of Wash Buffer (1:10 dilution of Wash Buffer concentrate (10 mM PBS buffer containing Tween 20 and sodium azide). Assay Buffer in the amount of 200 μL (0.05 M PBS at pH 6.8, containing protease inhibitors, with Tween 20, 0.08% sodium azide and 1% BSA) was then added to the non-specific binding wells A10-A12. Assay Buffer in the amount of 100 μL was added to the GLP-1 standard wells. A combination of Assay Buffer (98 μL) and dipeptidyl peptidase IV (DPP-IV) inhibitor (Linco Cat#DPP4) (2 μL) in a total amount of 100 μL was added to all of the cell sample wells. GLP-1 amide ELISA standards (GLP-1 (7-36 amide) in Assay Buffer: 2, 5, 10, 20, 50, and 100 μM) in the amount of 100 μL were added in ascending order in duplicate to the appropriate wells. Samples in the amount of 100 μL were then added to the remaining wells from cell plates. ELISA Plates were shaken gently for proper mixing.

The ELISA plates were then covered with an adhesive seal and incubated overnight (20 to 24 hours) at 4° C.

Liquid from the ELISA plates was then decanted, and excess fluid was tapped out on absorbent towels. ELISA Plates were washed 5 times with 300 μL of Wash Buffer per well with 5-minute incubation at room temperature in Wash Buffer with the fourth wash. Excess buffer was tapped out on absorbent towels after the fifth wash. Detection Conjugate (Anti GLP-1 Alkaline Phosphate Conjugate) in the amount of 200 μL was then immediately added in each well, followed by a 2-hour incubation period at room temperature. The Detection Conjugate was then decanted, and each well was then washed 3 times with 300 μL of Wash Buffer. Excess fluid was tapped out on paper towels. Diluted Substrate in 200 μL was added in each well and incubated at least 20 minutes at room temperature in the dark. The light sensitive Substrate MUP (Methyl Umbelliferyl Phosphate) was supplied in 10 mg in the Millipore's GLP-1 ELISA Kit and hydrated in 1 mL deionized water just before use. A 1:200 dilution was made in Substrate Diluent (e.g., 100 μL hydrated substrate in 20 mL substrate diluent). Dilution was made fresh each time just before use. After 20 minutes, plates were read at 355 nm/460 nm. When there was sufficient signal-to-noise ratio within the lowest point on standard curve (i.e. 2 μM) and the highest standard point (i.e., 100 μM) within the maximum relative fluorescence unit (RFU) read-out of plate reader, no additional incubation period was required. Otherwise, additional incubation time was required.

When the signal was sufficient, Stop Solution in the amount of 50 μL was added to each well in the same order that the Substrate was added, followed by a 5-minute incubation period in the dark at room temperature to arrest phosphatase activity. ELISA Plates were then read on a fluorescence plate reader with an excitation/emission wavelength of 355 nm/460 nm. Results are shown in FIGS. 16-19.

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method of treating type 2 diabetes in a mammal, comprising administering to a subject in need of said treatment an effective amount of one or more compounds of Formula I:

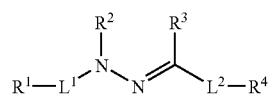

I or a physiologically acceptable salt thereof, wherein
$R^1$ is $C_{6-14}$ aryl, 5-14 membered heteroaryl, $C_{3-14}$ cycloalkyl, $C_{3-14}$ cycloalkenyl, 3-14 membered cycloheteroalkyl, 3-14 membered cycloheteroalkenyl, or $C_{1-6}$ alkyl, each of which is optionally substituted;
$R^2$ is H, $C_{1-6}$ alkyl, or $C_{6-10}$ aryl;
$R^3$ is H, $C_{1-6}$ alkyl, $C_{6-10}$ aryl, or cyano;
$R^4$ is $C_{6-14}$ aryl, 5-14 membered heteroaryl, $C_{3-14}$ cycloalkyl, $C_{3-14}$ cycloalkenyl, 3-14 membered cycloheteroalkyl, or 3-14 membered cycloheteroalkenyl, each of which is optionally substituted, or is cyano;
$L^1$ is absent, or is a linker containing 1-10 carbon atoms substituted with oxo at one carbon atom, a linker containing 2-10 carbon and heteroatoms, or a linker containing 1-10 heteroatoms, any of which is optionally substituted; and
$L^2$ is absent, or is a linker containing 1-10 heteroatoms and which is optionally substituted;

provided that when L¹ is absent, then L² is —N═N—, or when L' is —C(O)—, then R¹ is $C_{3-14}$ cycloalkyl;

wherein said compound is administered in an amount sufficient to treat type 2 diabetes.

2. A method of treating type 2 diabetes in a mammal, comprising administering to a subject in need of said treatment an effective amount of one or more compounds selected from the group consisting of methyl 4-((E)-((Z)-1-(2-(benzo[d]thiazol-2-yl)hydrazono)-2-methyl-propyl)-diazenyl)benzoate;

(E)-2-(4-bromo-2-((2-(quinolin-8-yl)hydrazono)methyl) phenoxy)acetic acid;

(E)-N'-(3,4-dimethoxybenzylidene)-2-(naphthalene-1-yl) acetohydrazide;

(E)-N'-(3,4-dimethoxybenzylidene)-2-phenylcyclopropane-carbohydrazide;

(E)-3-cyclohexenyl-4-hydroxy-N'-(4-methoxybenzylidene)-butanehydrazide;

(E)-N'-(3,4-dimethoxybenzylidene)-4-hydroxyhexanehydrazide;

2-((Z)-2-(phenyl-((E)-phenyldiazenyl)methylene)hydrazinyl)benzoic acid;

(E)-N'-(3,4-dimethoxybenzylidene)-2-(m-tolyloxy)acetohydrazide;

(E)-N'-(4-(allyloxy)-3-methoxybenzylidene)-2-(3-bromobenzylthio)-acetohydrazide;

(E)-N'-(4-isopropylbenzylidene)bicyclo[4.1.0]heptane-7-carbohydrazide;

(Z)-1,3,3-trimethyl-2-((E)-2-(2-(4-nitrophenyl)hydrazono)-ethylidene)indoline;

(E)-N'-(4-(diethylamino)-2-hydroxybenzylidene)-2-phenylcyclopropanecarbohydrazide;

(4-(trifluoromethylthio)phenyl)carbonohydrazonoyldicyanide;

N-((E)-3-((Z)-2-(1,5-dimethyl-2-oxoindolin-3-ylidene) hydrazinyl)-3-oxo-1-phenylprop-1-en-2-yl)benzamide;

(Z)-2-(2-((1-butyl-1H-indol-3-yl)methylene)hydrazinyl) benzoic acid;

(E)-4-((2-benzyl-2-phenylhydrazono)methyl)pyridine;

(Z)-N'-((1H-Pyrrol-2-yl)methylene)tricyclo[3.3.1.1³,⁷] decane-3-carbohydrazide;

(Z)-1-(2-(4-(ethyl(2-hydroxyethyl)amino)phenyl)hydrazono)-naphthalen-2-(1H)-one;

(E)-4-((2-(5-chloro-3-(trifluoromethyl)pyridin-2-yl)-2-2-methyl-hydrazono)methyl)benzene-1,3-diol;

(E)-2-(3,4-dimethylphenylamino)-N'-(4-morpholino-3-nitro-benzylidene)acetohydrazide;

(Z)-3-(2-nitro-5-(pyrrolidin-1-yl)phenyl)hydrazono)quinuclidine;

(E)-2-((2-(1H-benzo[d]imidazol-2-yl)hydrazono)methyl)-5-(diethylamino)phenol;

3-carbazol-9-ylpropionic acid (3,4-dimethoxybenzylidene)hydrazide; and (4,8-dimethylquinolin-2-ylsulfanyl)acetic acid (3,4-dimethoxybenzylidene)hydrazide.

3. The method according to claim 1, wherein said subject is human.

4. The method according to claim 1, wherein R¹ is optionally substituted $C_{6-10}$ aryl, optionally substituted 5-14 membered heteroaryl, optionally substituted $C_{3-10}$ cycloalkyl, optionally substituted $C_{3-10}$ cycloalkenyl, optionally substituted 3-10 membered cycloheteroalkyl, optionally substituted 3-10 membered cycloheteroalkenyl, or optionally substituted $C_{1-6}$ alkyl.

5. The method according to claim 1, wherein R² is H.

6. The method according to claim 1, wherein R⁴ is optionally substituted $C_{6-10}$ aryl, optionally substituted 5-10 membered heteroaryl, optionally substituted $C_{3-10}$ cycloalkyl, optionally substituted $C_{3-10}$ cycloalkenyl, optionally substituted 3-10 membered cycloheteroalkyl, or optionally substituted 3-10 membered cycloheteroalkenyl.

7. The method according to claim 1, wherein R¹ is unsubstituted phenyl, phenyl or naphthyl, each of which is substituted 1, 2, or 3 substituents independently selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$ alkylenedioxy, $C_{1-6}$ alkoxy($C_{1-6}$)alkyl, $C_{1-6}$aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy($C_{2-6}$)alkoxy, $C_{2-6}$ carboxyalkoxy, and $C_{2-6}$ carboxyalkyl, a nitrogen-containing heteroaryl, or selected from the group consisting of pyridyl, pyrimidinyl, imidazolyl, tetrazolyl, furanyl, thienyl, indolyl, azaindolyl, quinolinyl, pyrrolyl, benzimidazolyl, and benzothiazolyl, each of which is optionally substituted.

8. The method according to claim 1, wherein R⁴ is unsubstituted phenyl, phenyl or naphthyl, each of which is substituted 1, 2, or 3 substituents independently selected from the group consisting of amino, hydroxy, nitro, halogen, cyano, thiol, $C_{1-6}$ alkyl, $C_{2-6}$ alkenyl, $C_{1-6}$ haloalkyl, $C_{1-6}$ alkoxy, $C_{3-6}$ alkenyloxy, $C_{1-6}$alkylenedioxy, $C_{1-6}$ alkoxy($C_{1-6}$)alkyl, $C_{1-6}$aminoalkyl, $C_{1-6}$ aminoalkoxy, $C_{1-6}$ hydroxyalkyl, $C_{2-6}$ hydroxyalkoxy, mono($C_{1-4}$)alkylamino, di($C_{1-4}$)alkylamino, $C_{2-6}$ alkylcarbonylamino, $C_{2-6}$ alkoxycarbonylamino, $C_{2-6}$alkoxycarbonyl, carboxy, ($C_{1-6}$)alkoxy($C_{2-6}$)alkoxy, $C_{2-6}$ carboxyalkoxy, and $C_{2-6}$ carboxyalkyl, a nitrogen-containing heteroaryl, or selected from the group consisting of pyridyl, pyrimidinyl, imidazolyl, tetrazolyl, furanyl, thienyl, indolyl, azaindolyl, quinolinyl, pyrrolyl, benzimidazolyl, and benzothiazolyl, each of which is optionally substituted.

9. The method according to claim 1, wherein
(a) R¹ is optionally substituted $C_{6-10}$ aryl; R² is H or $C_{1-6}$ alkyl; R³ is H or $C_{1-6}$ alkyl; and R⁴ is optionally substituted $C_{6-10}$ aryl;
(b) R¹ is optionally substituted 5-10 membered heteroaryl; R² is H or $C_{1-6}$ alkyl; R³ is H or $C_{1-6}$ alkyl; and R⁴ is optionally substituted $C_{6-10}$ aryl;
(c) R¹ is optionally substituted $C_{6-10}$ aryl; R² is H or $C_{1-6}$ alkyl; R³ is H or $C_{1-6}$ alkyl; and R⁴ is optionally substituted 5-10 membered heteroaryl;
(d) R¹ is optionally substituted 5-10 membered heteroaryl; R² is H or $C_{1-6}$ alkyl; R³ is H or $C_{1-6}$ alkyl; and R⁴ is optionally substituted 5-10 membered heteroaryl;
(e) R¹ is optionally substituted $C_{6-10}$ aryl; R² is H or $C_{1-6}$ alkyl; R³ is H or $C_{1-6}$ alkyl; and R⁴ is optionally substituted $C_{3-10}$ cycloalkyl;
(f) R¹ is optionally substituted 5-10 membered heteroaryl; R² is H or $C_{1-6}$ alkyl; R³ is H or $C_{1-6}$ alkyl; and R⁴ and L² together form —N═N-aryl;
(g) R¹ is heteroaryl; R² is H; R⁴ is heteroaryl; L¹ is absent; and L² is N═N;
(h) R¹ is aryl; R² is H; R³ is H; R⁴ is aryl or heteroaryl; L¹ is as defined in claim 1; and L² is absent; or
(i) R¹ is cycloalkenyl; R² is H; R³ is H; R⁴ is aryl or heteroaryl; L¹ is as defined in claim 1; and L² is absent.

10. The method according to claim 1, wherein R² is $C_{1-6}$ alkyl.

11. The method according to claim 1, wherein R² is $C_{1-10}$ aryl.

12. The method according to claim 1, wherein R³ is H.

13. The method according to claim 1, wherein R³ is $C_{1-6}$ alkyl.

14. The method according to claim 1, wherein $R^3$ is $C_{6-10}$ aryl.

15. The method according to claim 1, wherein $R^3$ is cyano.

16. The method according to claim 1, wherein $L^1$ is absent and $L^2$ is —N=N—.

17. The method according to claim 1, wherein $L^1$ is a linker containing 1-10 carbon atoms substituted with oxo at one carbon atom, which is further optionally substituted, provided that when $L^1$ is —C(O)—, then $R^1$ is $C_{3-14}$ cycloalkyl.

18. The method according to claim 17, wherein $L^1$ is a linker selected from the group consisting of

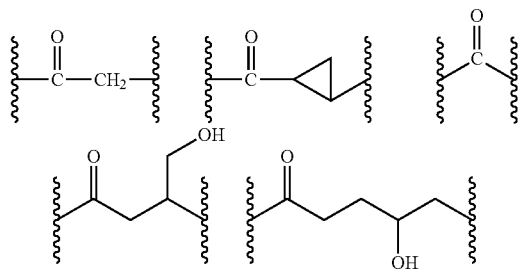

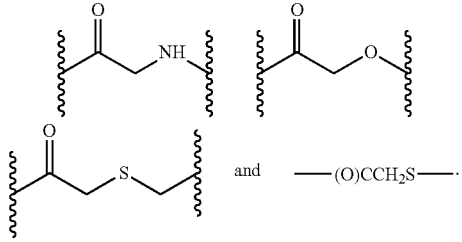

and —(O)CCH$_2$S—.

19. The method according to claim 18, wherein $L^1$ is a linker selected from the group consisting of -cyclopropyl-C(O)—, —CH$_2$C(O)—, —CH(CH$_2$OH)CH$_2$C(O)—, —CH$_2$CH(OH)CH$_2$CH$_2$C(O)—, —OCH$_2$C(O)—, —CH$_2$SCH$_2$C(O)—, —NHCH$_2$C(O)—, —CH$_2$CH$_2$C(O)—, and —SCH$_2$C(O)—.

20. The method according to claim 1, wherein $L^1$ is a linker containing 1-10 heteroatoms, which is optionally substituted.

21. The method according to claim 20, wherein $L^1$ is —O—, —S—, —NH—, or —N=N—.

22. The method according to claim 1, wherein $L^2$ is absent.

* * * * *